(12) United States Patent
Wilson et al.

(10) Patent No.: US 11,911,061 B2
(45) Date of Patent: Feb. 27, 2024

(54) SYSTEMS AND METHODS FOR ENDOLUMINAL VALVE CREATION

(71) Applicant: INTERVENE, INC., South San Francisco, CA (US)

(72) Inventors: Fletcher T. Wilson, San Francisco, CA (US); Mariel Fabro, South San Francisco, CA (US); Zachary J. Malchano, South San Francisco, CA (US)

(73) Assignee: INTERVENE, INC., South San Francisco, CA (US)

( * ) Notice: Subject to any disclaimer, the term of this patent is extended or adjusted under 35 U.S.C. 154(b) by 495 days.

(21) Appl. No.: 17/098,091

(22) Filed: Nov. 13, 2020

(65) Prior Publication Data
US 2021/0204971 A1 Jul. 8, 2021

Related U.S. Application Data

(63) Continuation of application No. 15/921,470, filed on Mar. 14, 2018, now Pat. No. 10,874,413, which is a
(Continued)

(51) Int. Cl.
*A61B 17/32* (2006.01)
*A61B 17/08* (2006.01)
(Continued)

(52) U.S. Cl.
CPC ............ *A61B 17/320016* (2013.01); *A61B 17/00491* (2013.01); *A61B 17/064* (2013.01);
(Continued)

(58) Field of Classification Search
CPC ...... A61B 18/1492; A61B 2017/00557; A61B 17/3478; A61B 2018/0022;
(Continued)

(56) References Cited

U.S. PATENT DOCUMENTS 3,704,711 A  12/1972 Park
4,794,931 A  1/1989 Yock
(Continued)

FOREIGN PATENT DOCUMENTS

CA  1281381 C  3/1991
CA  2678971 A1  8/2008
(Continued)

OTHER PUBLICATIONS

Corcos, I., "A new autologous venous valve by intimal flap: One Cases report." Note Di Tecnica, Minerva Cardioangiol, 2003, 51, 10 pages.
(Continued)

*Primary Examiner* — Katherine M Shi
(74) *Attorney, Agent, or Firm* — Perkins Coie LLP

(57) ABSTRACT

Systems and methods for creating autologous monocuspid and bicuspid valves can include a catheter having a single expandable element or a double expandable element. Once the leaflets of the valve are created, various techniques can be used to fix the leaflets to the vessel wall or to each other, including clips, tissue anchors, adhesives, and heat.

17 Claims, 52 Drawing Sheets

Related U.S. Application Data continuation of application No. 14/759,797, filed as application No. PCT/US2014/011169 on Jan. 10, 2014, now Pat. No. 9,955,990.

(60) Provisional application No. 61/821,726, filed on May 10, 2013, provisional application No. 61/751,218, filed on Jan. 10, 2013.

(51) Int. Cl.

| | | |
|---|---|---|
| *A61B 17/064* | (2006.01) | |
| *A61B 17/068* | (2006.01) | |
| *A61B 17/10* | (2006.01) | |
| *A61B 17/3203* | (2006.01) | |
| *A61B 17/00* | (2006.01) | |
| *A61F 2/24* | (2006.01) | |
| *A61B 17/22* | (2006.01) | |
| *A61B 17/29* | (2006.01) | |
| *A61B 17/34* | (2006.01) | |
| *A61B 17/06* | (2006.01) | |

(52) U.S. Cl.
CPC .......... *A61B 17/068* (2013.01); *A61B 17/083* (2013.01); *A61B 17/10* (2013.01); *A61B 17/3203* (2013.01); *A61F 2/2475* (2013.01); *A61B 17/32037* (2013.01); *A61B 2017/00504* (2013.01); *A61B 2017/00557* (2013.01); *A61B 2017/00783* (2013.01); *A61B 2017/061* (2013.01); *A61B 2017/0645* (2013.01); *A61B 2017/0649* (2013.01); *A61B 2017/22061* (2013.01); *A61B 2017/22071* (2013.01); *A61B 2017/22072* (2013.01); *A61B 2017/2937* (2013.01); *A61B 2017/320048* (2013.01); *A61B 2017/320052* (2013.01); *A61B 2017/3445* (2013.01)

(58) Field of Classification Search
CPC .. A61B 2017/00243; A61B 17/320016; A61B 17/064; A61B 17/068; A61B 17/083; A61B 17/10; A61M 25/10; A61M 25/104; A61M 2025/1043; A61M 2025/1086; A61M 25/0082; A61M 25/0084; A61M 2025/0095; A61M 2025/0096; A61M 2025/0087

See application file for complete search history.

(56) References Cited

U.S. PATENT DOCUMENTS

| | | |
|---|---|---|
| 4,898,574 A | 2/1990 | Uchiyama et al. |
| 4,932,962 A | 6/1990 | Yoon et al. |
| 5,112,339 A | 5/1992 | Zelman et al. |
| 5,190,046 A | 3/1993 | Shturman et al. |
| 5,372,601 A | 12/1994 | Lary |
| 5,443,443 A | 8/1995 | Shiber |
| 5,464,395 A | 11/1995 | Faxon et al. |
| 5,601,588 A | 2/1997 | Tonomura et al. |
| 5,606,975 A | 3/1997 | Liang et al. |
| 5,695,507 A | 12/1997 | Auth et al. |
| 5,738,901 A | 4/1998 | Wang et al. |
| 5,795,322 A | 8/1998 | Boudewijn |
| 5,810,847 A | 9/1998 | Laufer et al. |
| 5,836,945 A | 11/1998 | Perkins |
| 5,882,340 A | 3/1999 | Yoon |
| 5,989,276 A | 11/1999 | Houser et al. |
| 6,190,353 B1 | 2/2001 | Makower |
| 6,302,870 B1 * | 10/2001 | Jacobsen ............ A61B 17/22 604/170.03 |
| 6,375,635 B1 | 4/2002 | Moutafis et al. |
| 6,379,319 B1 | 4/2002 | Garibotto et al. |
| 6,344,027 B1 | 5/2002 | Goll |
| 6,458,098 B1 | 10/2002 | Kanesaka |
| 6,475,226 B1 | 11/2002 | Belef et al. |
| 6,506,178 B1 | 1/2003 | Schubart et al. |
| 6,514,217 B1 | 2/2003 | Selmon et al. |
| 6,524,251 B2 | 2/2003 | Rabiner et al. |
| 6,676,665 B2 | 1/2004 | Foley et al. |
| 6,685,648 B2 | 2/2004 | Flaherty et al. |
| 6,692,466 B1 | 2/2004 | Chow |
| 6,702,744 B2 | 3/2004 | Mandrusov |
| 6,726,677 B1 | 4/2004 | Flaherty et al. |
| 6,758,836 B2 | 7/2004 | Zawacki |
| 6,902,576 B2 | 6/2005 | Drasler et al. |
| 7,008,411 B1 | 3/2006 | Mandrusov et al. |
| 7,056,325 B1 | 6/2006 | Makower et al. |
| 7,150,738 B2 | 12/2006 | Ray |
| 7,179,249 B2 | 2/2007 | Steward et al. |
| 7,273,469 B1 | 9/2007 | Chan et al. |
| 7,357,795 B2 | 4/2008 | Kaji et al. |
| 7,517,352 B2 | 4/2009 | Evans |
| 7,775,968 B2 | 8/2010 | Mathis |
| 7,780,592 B2 | 8/2010 | Tronnes |
| 7,918,870 B2 | 4/2011 | Kugler et al. |
| 7,927,305 B2 | 4/2011 | Yribarren et al. |
| 7,938,819 B2 | 5/2011 | Kugler et al. |
| 7,955,346 B2 | 6/2011 | Mauch et al. |
| 8,025,655 B2 | 9/2011 | Kugler et al. |
| 8,083,726 B1 | 12/2011 | Wang |
| 8,083,727 B2 | 12/2011 | Kugler et al. |
| 8,100,860 B2 | 1/2012 | Von Oepen et al. |
| 8,114,123 B2 | 2/2012 | Brenzel et al. |
| 8,177,748 B1 | 5/2012 | Beyerlein |
| 8,177,802 B2 | 5/2012 | Mauch et al. |
| 8,267,947 B2 | 9/2012 | Pantages et al. |
| 8,323,261 B2 | 12/2012 | Kugler |
| 8,460,316 B2 | 6/2013 | Wilson et al. |
| 8,636,712 B2 | 1/2014 | Kugler et al. |
| 8,753,366 B2 | 6/2014 | Makower et al. |
| 9,320,504 B2 | 4/2016 | Wilson et al. |
| 9,381,034 B2 | 7/2016 | Kawwei |
| 9,545,289 B2 | 1/2017 | Wilson et al. |
| 9,814,538 B2 | 11/2017 | Kugler et al. |
| 9,827,005 B2 | 11/2017 | Wilson et al. |
| 9,949,752 B2 | 4/2018 | Wilson et al. |
| 9,955,990 B2 | 5/2018 | Wilson et al. |
| 10,105,157 B2 | 10/2018 | Wilson et al. |
| 10,188,419 B2 | 1/2019 | Wilson et al. |
| 10,231,613 B2 | 3/2019 | Wilson et al. |
| 10,292,807 B2 | 5/2019 | Wilson et al. |
| 10,603,018 B2 | 3/2020 | Wilson et al. |
| 10,646,247 B2 | 5/2020 | Wilson et al. |
| 10,874,413 B2 | 12/2020 | Wilson et al. |
| 2001/0041899 A1 | 11/2001 | Foster |
| 2002/0029052 A1 | 3/2002 | Evans et al. |
| 2002/0072706 A1 | 6/2002 | Hiblar et al. |
| 2002/0091362 A1 | 7/2002 | Maginot |
| 2002/0103459 A1 | 8/2002 | Sparks et al. |
| 2002/0148475 A1 | 10/2002 | Johnson et al. |
| 2003/0125663 A1 | 7/2003 | Coleman et al. |
| 2003/0144670 A1 | 7/2003 | Pavcnik et al. |
| 2004/0167558 A1 | 8/2004 | Igo et al. |
| 2004/0215339 A1 | 10/2004 | Drasler et al. |
| 2005/0014995 A1 | 1/2005 | Amundson et al. |
| 2005/0075665 A1 | 4/2005 | Brenzel et al. |
| 2005/0165466 A1 | 7/2005 | Morris et al. |
| 2005/0273159 A1 | 12/2005 | Opie |
| 2006/0094929 A1 | 5/2006 | Tronnes |
| 2006/0136045 A1 | 6/2006 | Flagle et al. |
| 2006/0156875 A1 | 7/2006 | McRury et al. |
| 2006/0178646 A1 | 8/2006 | Harris et al. |
| 2006/0184187 A1 | 8/2006 | Surti |
| 2006/0235449 A1 | 10/2006 | Schubart et al. |
| 2006/0271090 A1 | 11/2006 | Shaked et al. |
| 2007/0005093 A1 | 1/2007 | Cox et al. |
| 2007/0093780 A1 | 4/2007 | Kugler |
| 2007/0093781 A1 | 4/2007 | Kugler et al. |
| 2007/0129628 A1 | 6/2007 | Hirsh |
| 2007/0208368 A1 | 9/2007 | Katoh et al. |
| 2008/0033467 A1 | 2/2008 | Miyamoto et al. |

(56) References Cited

U.S. PATENT DOCUMENTS

| | | |
|---|---|---|
| 2008/0103480 A1 | 5/2008 | Bosel et al. |
| 2008/0228171 A1 | 9/2008 | Kugler et al. |
| 2008/0228211 A1 | 9/2008 | Gonon |
| 2008/0243065 A1 | 10/2008 | Rottenberg et al. |
| 2008/0255595 A1 | 10/2008 | Buchbinder et al. |
| 2009/0005793 A1 | 1/2009 | Pantages et al. |
| 2009/0112059 A1 | 4/2009 | Nobis |
| 2009/0149739 A9 | 6/2009 | Maschke |
| 2009/0182192 A1 | 7/2009 | Shiono et al. |
| 2009/0209910 A1 | 8/2009 | Kugler et al. |
| 2009/0254051 A1 | 10/2009 | Von Oepen et al. |
| 2009/0270799 A1 | 10/2009 | Seto et al. |
| 2010/0076476 A1 | 3/2010 | To et al. |
| 2010/0152843 A1 | 6/2010 | Mauch et al. |
| 2010/0256599 A1 | 10/2010 | Kassab et al. |
| 2011/0264127 A1 | 10/2011 | Mauch et al. |
| 2011/0264128 A1 | 10/2011 | Mauch et al. |
| 2012/0289987 A1 | 11/2012 | Wilson et al. |
| 2013/0066346 A1 | 3/2013 | Pigott et al. |
| 2013/0103070 A1 | 4/2013 | Kugler et al. |
| 2013/0116715 A1 | 5/2013 | Weber |
| 2013/0172883 A1 | 7/2013 | Lopes et al. |
| 2013/0216114 A1 | 8/2013 | Courtney et al. |
| 2013/0317534 A1 | 11/2013 | Zhou et al. |
| 2015/0057566 A1 | 2/2015 | Vetter et al. |
| 2015/0112188 A1 | 4/2015 | Stigall et al. |
| 2016/0081656 A1 | 3/2016 | Abraham |
| 2018/0289441 A1 | 10/2018 | Wilson et al. |
| 2018/0333166 A1 | 11/2018 | Wilson et al. |
| 2018/0361118 A1 | 12/2018 | Cully et al. |
| 2019/0314620 A1 | 10/2019 | Chang et al. |
| 2020/0275975 A1 | 9/2020 | Chen |
| 2020/0337726 A1 | 10/2020 | Wilson et al. |

FOREIGN PATENT DOCUMENTS

| | | |
|---|---|---|
| CN | 1907243 A | 2/2007 |
| CN | 1957861 A | 5/2007 |
| JP | 2002514111 A | 5/2002 |
| JP | 2003033357 A | 2/2003 |
| JP | 2003267160 A | 9/2003 |
| JP | 2009165822 A | 7/2009 |
| JP | 2009183516 A | 8/2009 |
| RU | 1012108751 C1 | 4/1998 |
| RU | 2160057 C2 | 10/2000 |
| WO | 1999000059 A1 | 1/1999 |
| WO | 2007005535 A1 | 1/2007 |
| WO | 2008063621 A2 | 5/2008 |
| WO | 2010074853 A1 | 7/2010 |
| WO | 1512011106735 A1 | 9/2011 |
| WO | 2012030587 A1 | 3/2012 |
| WO | 2012145444 A2 | 10/2012 |
| WO | 2013119849 A1 | 8/2013 |
| WO | 2013159066 A1 | 10/2013 |
| WO | 2014110460 A1 | 7/2014 |
| WO | 2016025733 A1 | 2/2016 |
| WO | 2017210656 A1 | 12/2017 |

OTHER PUBLICATIONS

Lugli, M., et al., Neovalve construction in the deep venous incompetence. J. Vasc. Surg., Jan. 2009, 49(1), 156-62.
Maleti, O., "Neovalve construction in postthrobotic syndrome," J. Vasc. Surg., vol. 34, No. 4, 6 pages.
International Search Report for International Appl. No. PCT/US2014/011169, dated May 22, 2014, 2 pages.
Non-Final Office Action dated Jul. 14, 2017; U.S. Appl. No. 14/759,797, 9 pages.
Non-Final Office Action dated Jan. 22, 2020; U.S. Appl. No. 15/921,470, 10 pages.

* cited by examiner

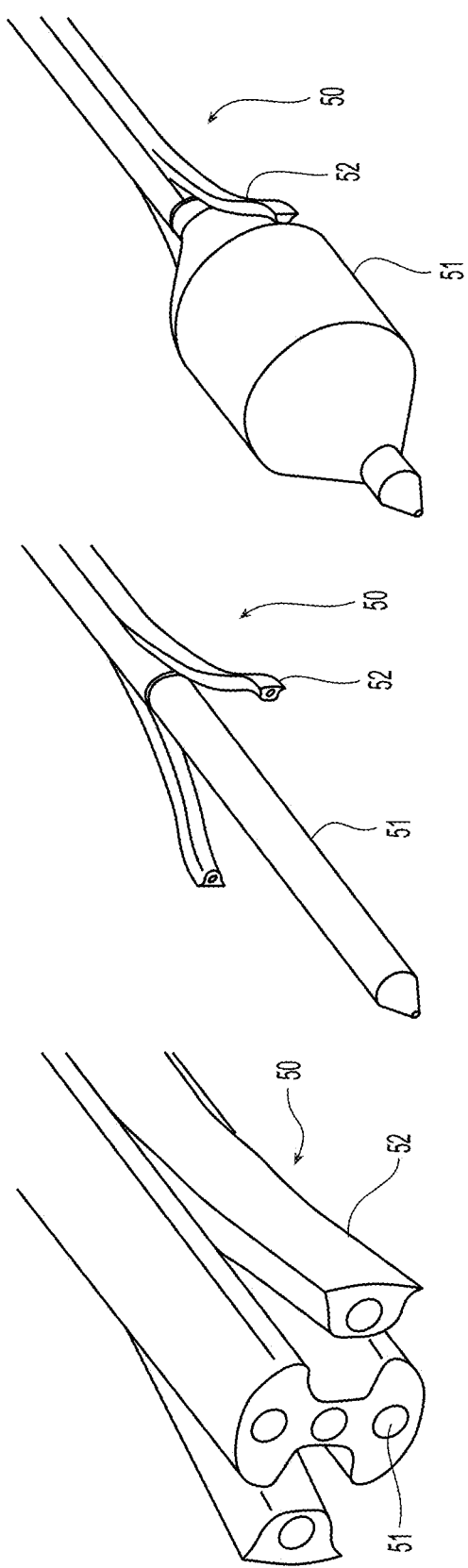
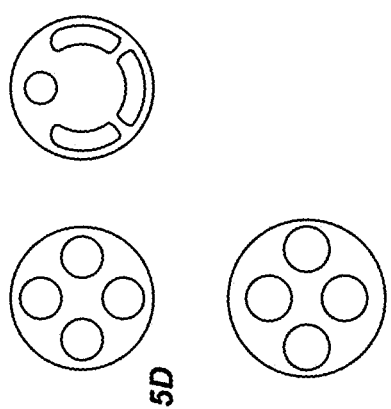
Fig. 5A  Fig. 5B  Fig. 5C
Fig. 5D  Fig. 5E  Fig. 5F

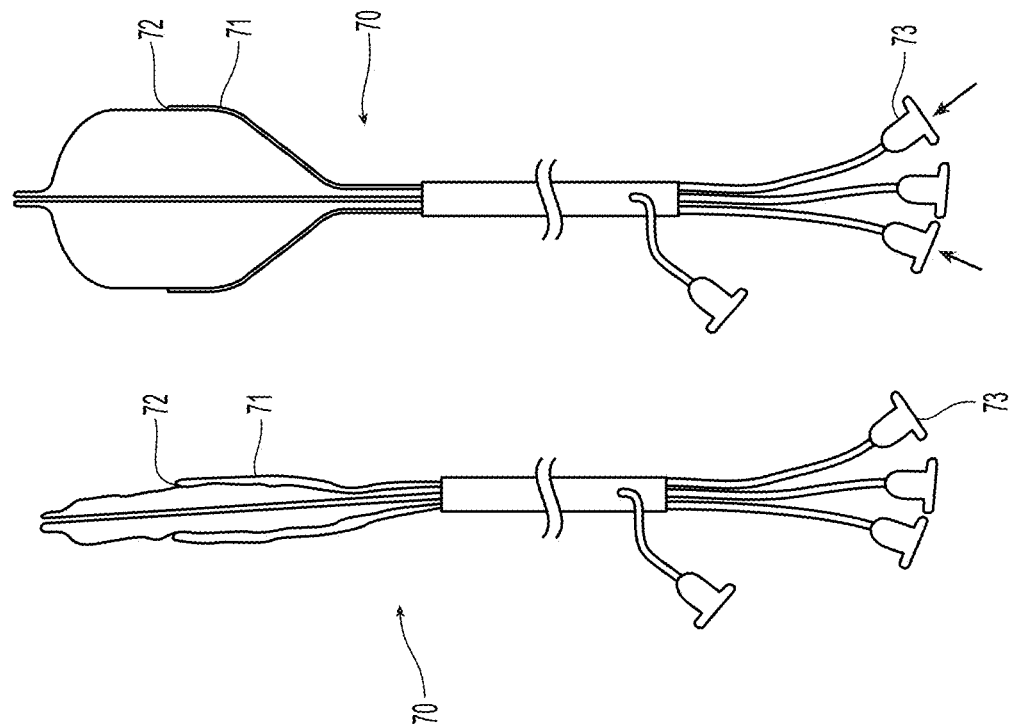

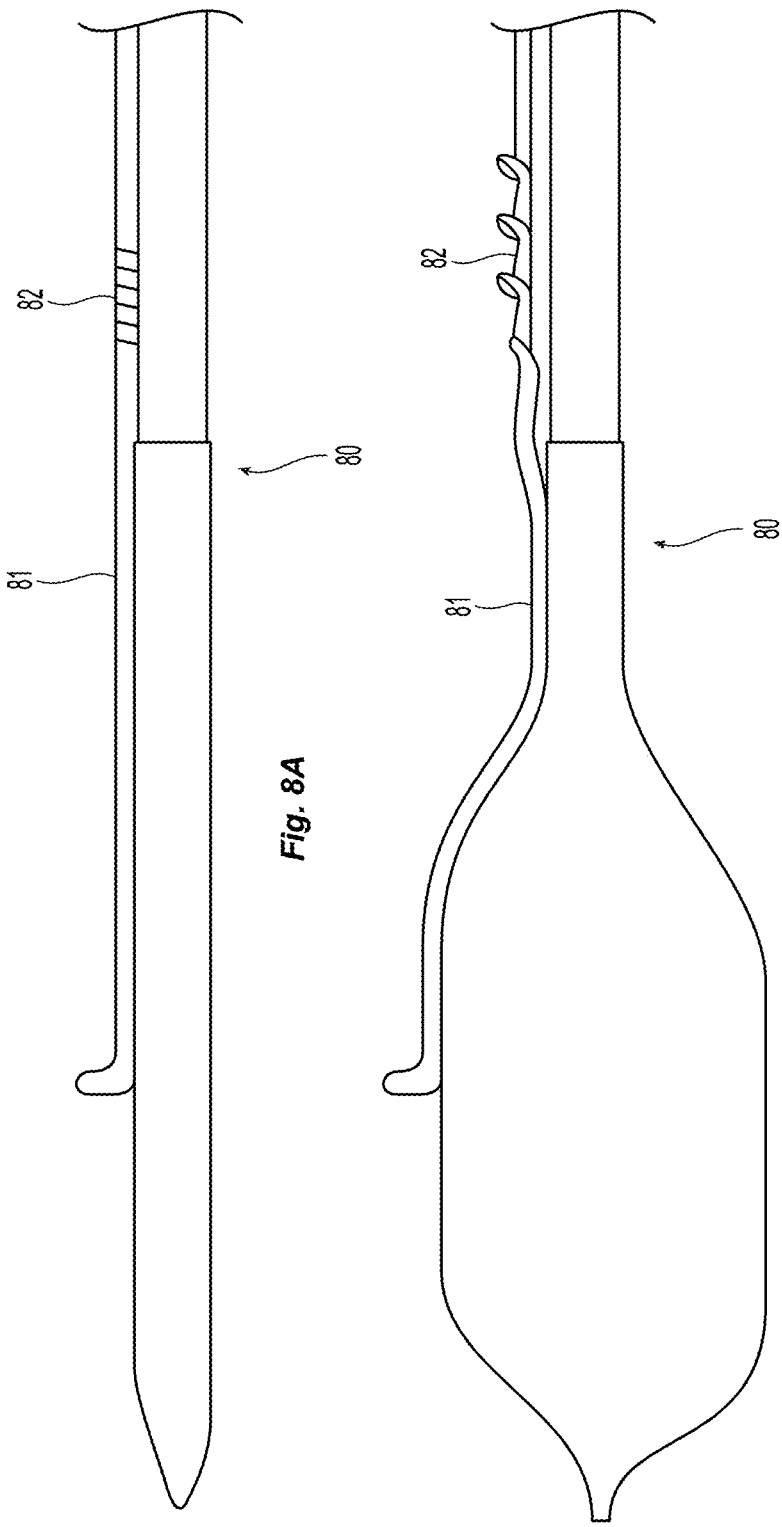

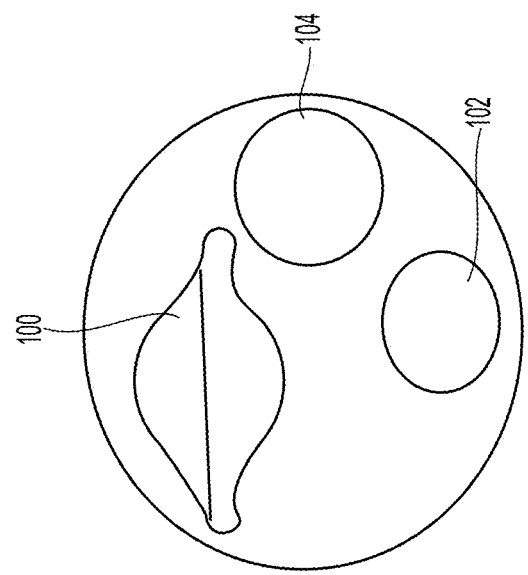
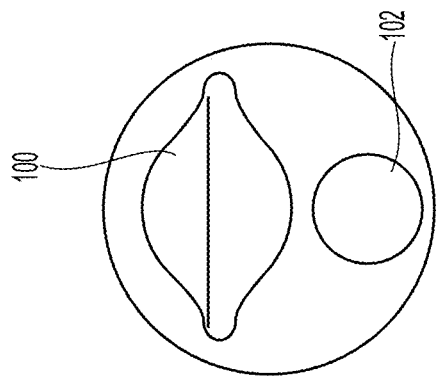
Fig. 10B
Fig. 10A

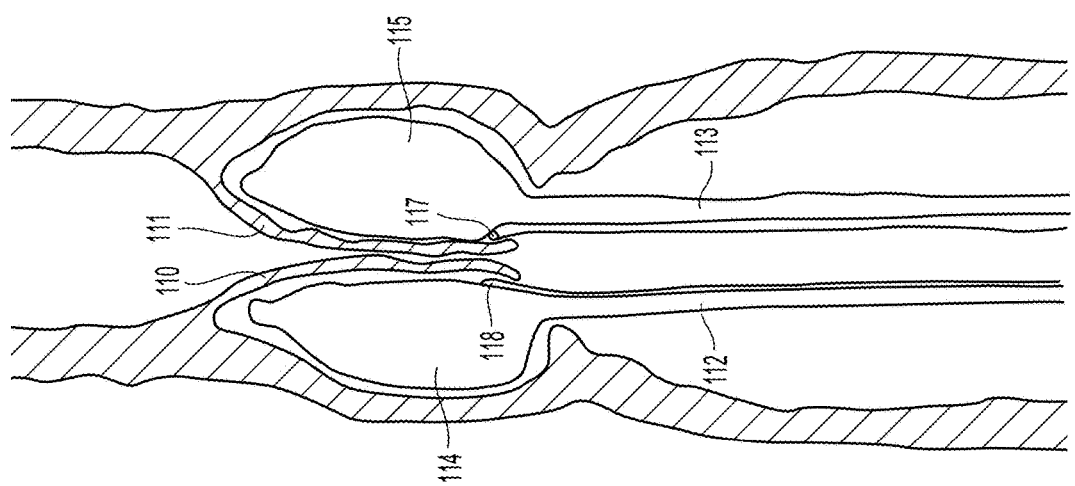
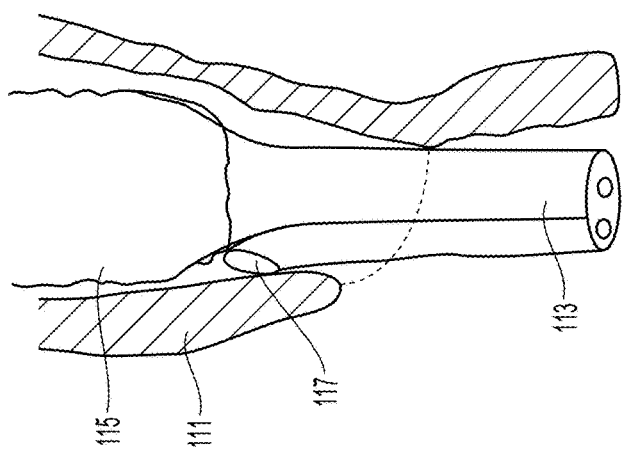
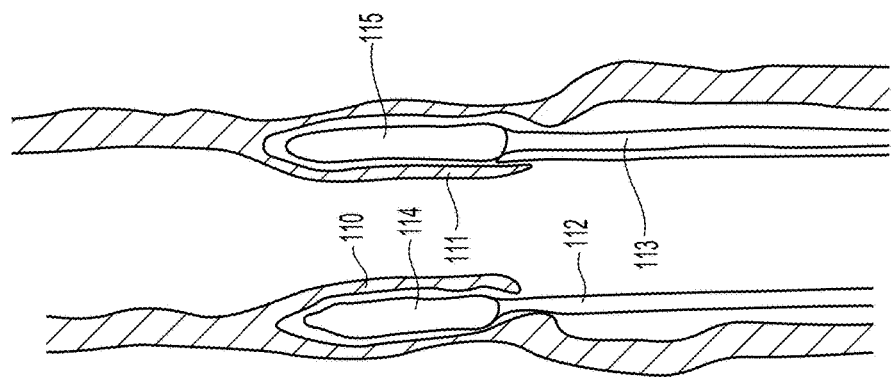
Fig. 11C
Fig. 11B
Fig. 11A

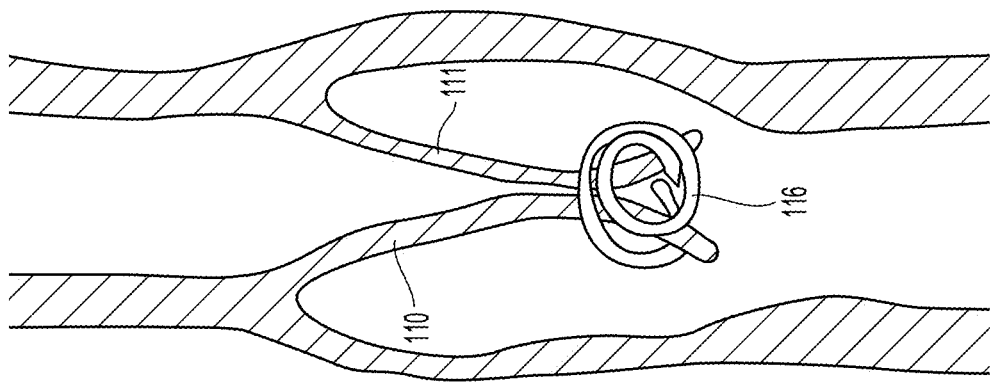
*Fig. 11F*
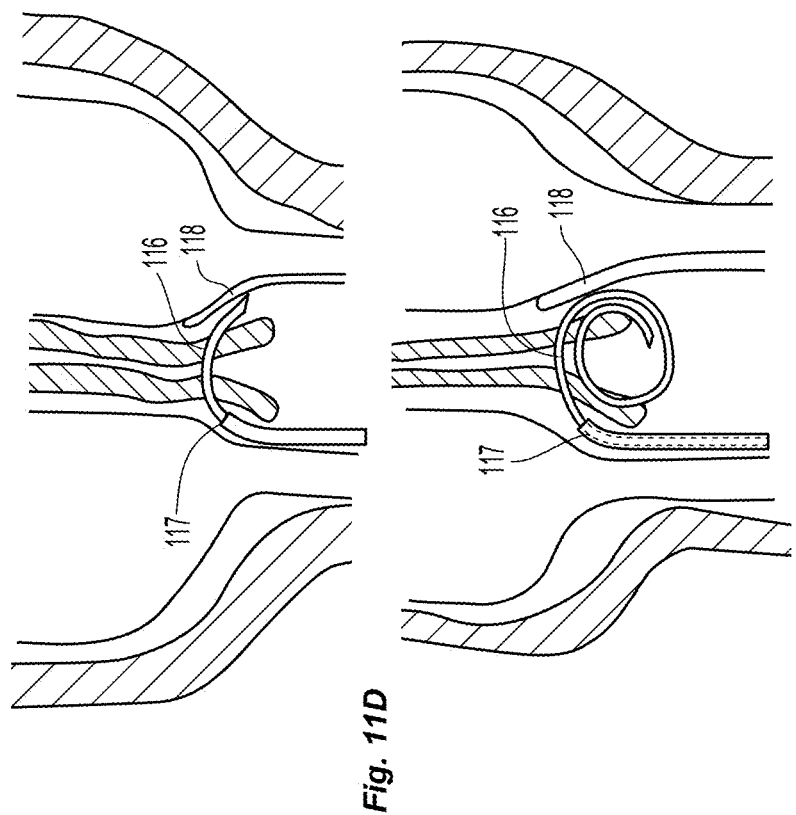
*Fig. 11D*  *Fig. 11E*

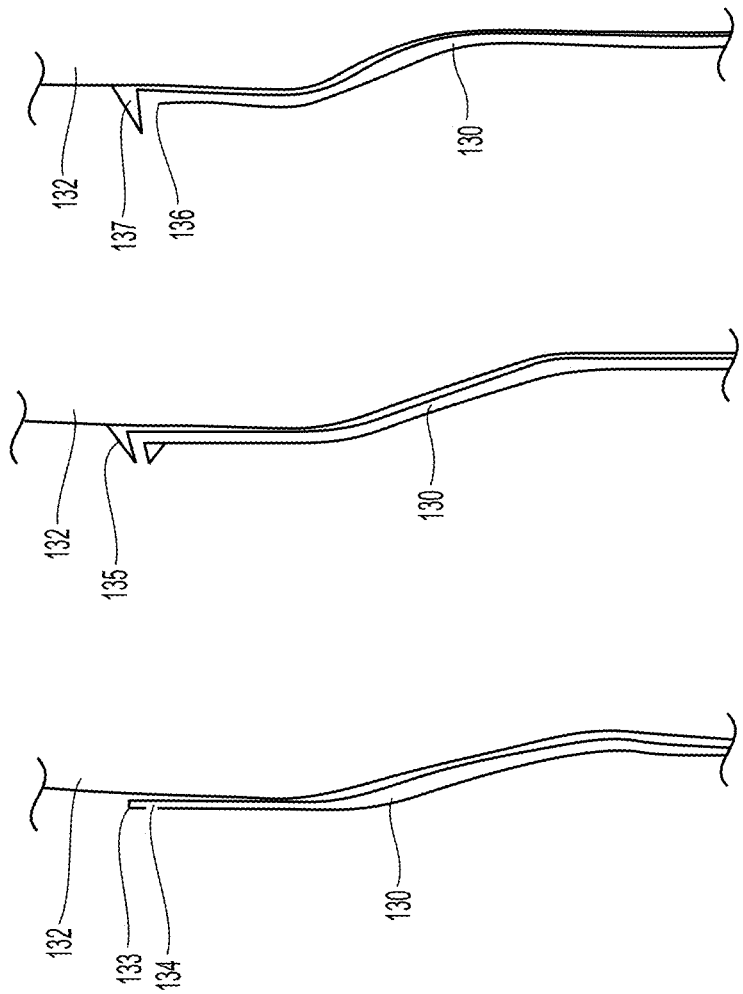

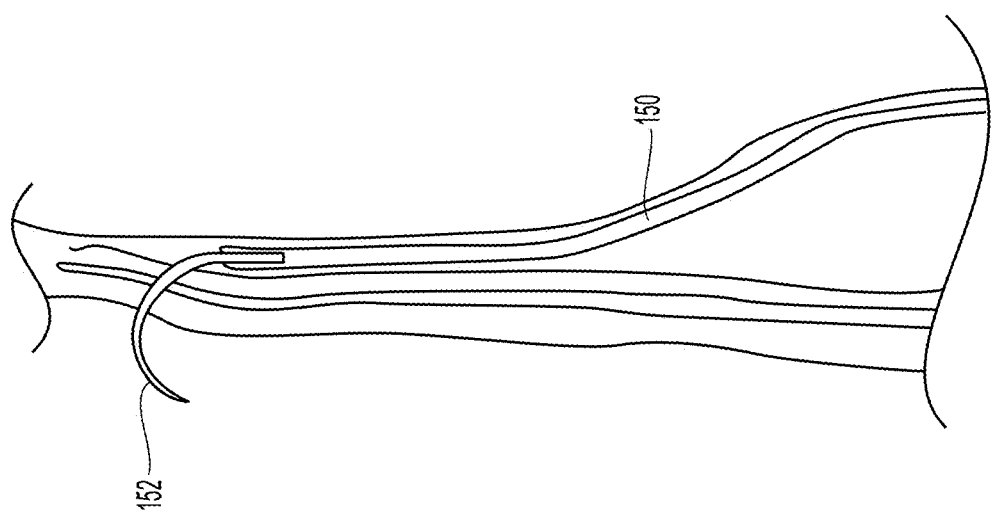

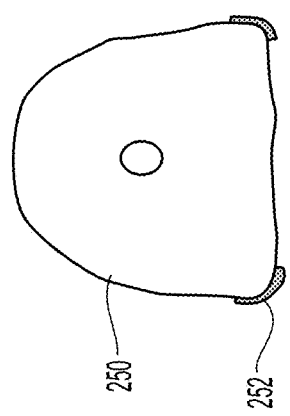
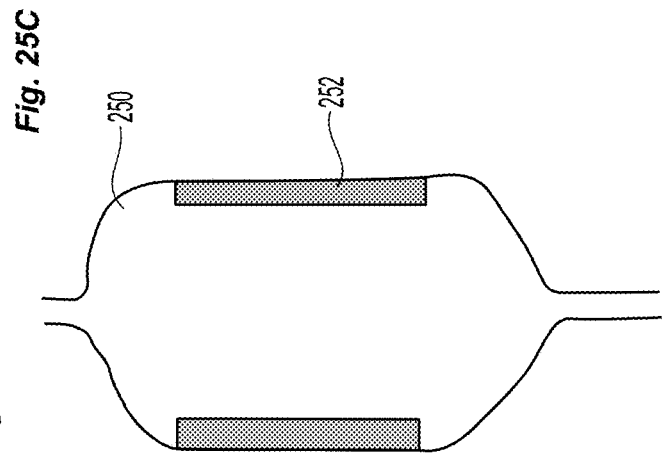

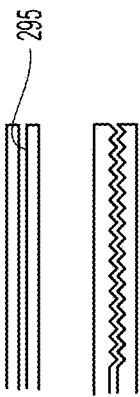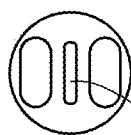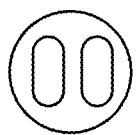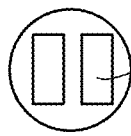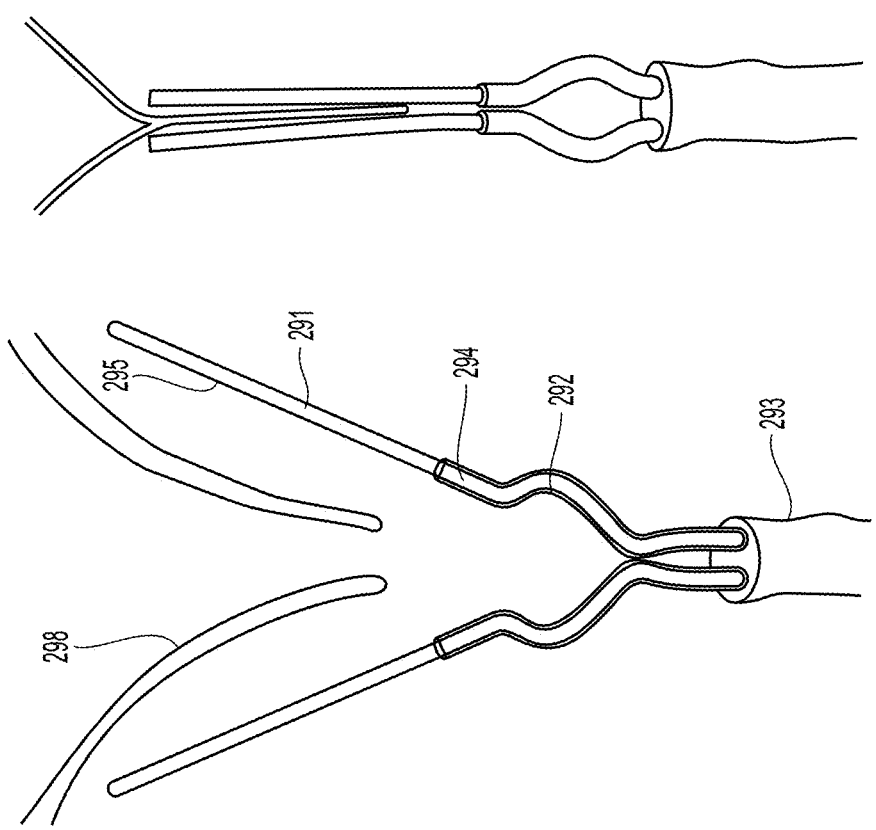

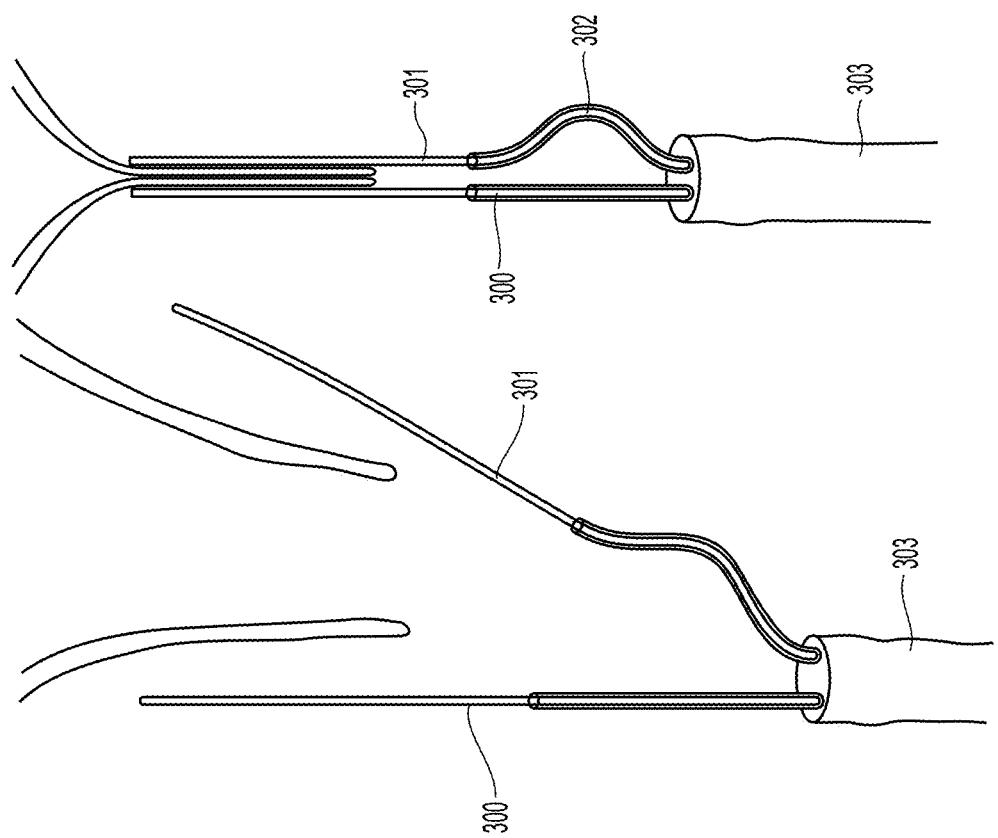

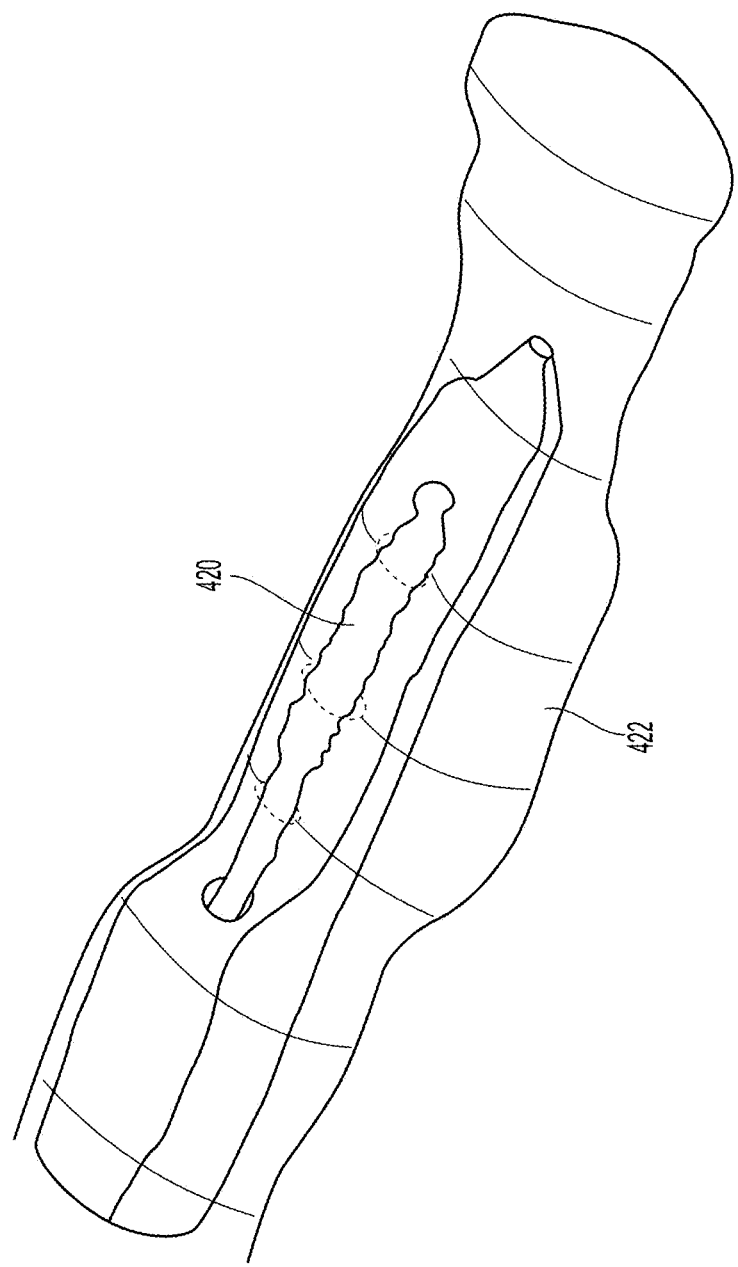

SYSTEMS AND METHODS FOR ENDOLUMINAL VALVE CREATION

CROSS REFERENCE TO RELATED APPLICATIONS

This application is a continuation of U.S. patent application Ser. No. 15/921,470, filed Mar. 14, 2018, now U.S. Pat. No. 10,874,413, which is a continuation of U.S. patent application Ser. No. 14/759,797, filed Jul. 8, 2015, now U.S. Pat. No. 9,955,990, which is a 35 U.S. C. 371 U.S. National Phase application of International Application No. PCT/US2014/011169, filed Jan. 10, 2014, entitled "SYSTEMS AND METHODS FOR ENDOLUMINAL VALVE CREATION," which claims priority to U.S. Provisional Application No. 61/751,218, filed Jan. 10, 2013, and U.S. Provisional Application No. 61/821,726, filed May 10, 2013, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present application pertains generally to medical systems and methods for fixation of an autologous tissue valves within a mammalian body.

BACKGROUND

Venous reflux is a medical condition affecting the circulation of blood, such as in the lower extremities or neck. The valves in the vessel that normally force blood back towards the heart cannot function properly. As a result, blood flows backwards, causing unwanted clinical problems such as ulceration or even multiple sclerosis when chronic cerebrospinal venous insufficiency is present. Applicant of the subject application determines that new systems and methods for treating venous reflux would be desirable.

SUMMARY OF THE DISCLOSURE

The present invention relates generally to medical systems and methods for fixation of an autologous tissue valves within a mammalian body.

In some embodiments, a system for fixing a first valve leaflet to a second valve leaflet is provided. The system can include a first leaflet engaging member having a proximal end and a distal end, an inner facing surface, and a deploying feature offset from the distal end of the first leaflet engaging member at a first predetermined distance, the first predetermined distance less than the length of the first valve leaflet; a second leaflet engaging member having a proximal end and a distal end, an inner facing surface that faces the inner facing surface of the first leaflet engaging member, and a receiving feature offset from the distal end of the second leaflet engaging member at a second predetermined distance, the second predetermined distance less than the length of the second valve leaflet; and a fixation element releasably disposed within the deploying feature.

In some embodiments, the first leaflet engaging member and the second leaflet engaging member are both expandable.

In some embodiments, the deploying feature is proximate and aligned with the receiving feature when the first leaflet engaging member and the second leaflet engaging member are both in an expanded configuration.

In some embodiments, the system further includes a catheter having a first lumen with a first distal port and a second lumen with a second distal port, wherein the first leaflet engaging member is slidably disposed within the first lumen and the second leaflet engaging member is slidably disposed within the second lumen.

In some embodiments, the system further includes a catheter having a lumen with a distal port, wherein the first leaflet engaging member and the second leaflet engaging member are slidably disposed within the lumen.

In some embodiments, the first leaflet engaging member and the second leaflet engaging member are articulatable with respect to each other.

In some embodiments, at least one of the first leaflet engaging member and the second leaflet engaging member is outwardly biased.

In some embodiments, the first leaflet engaging member and the second leaflet engaging member are in an open configuration when the first leaflet engaging member and the second leaflet engaging member are fully extended from the catheter.

In some embodiments, the first leaflet engaging member and the second leaflet engaging member are in a closed configuration when the first leaflet engaging member and the second leaflet engaging member are partially extended from the catheter, wherein the deploying feature is proximate and aligned with the receiving feature in the closed configuration.

In some embodiments, a system for creation of an autologous bicuspid valve is provided. The system can include a catheter having a fluid delivery lumen, a visualization lumen, an inflation lumen in fluid communication with a wall apposition balloon positioned on one side of the distal end of the catheter, and a tool lumen having a distal port and a longitudinal slot extending proximally from distal port; a visualization device slidably disposed within the visualization lumen; a first valve creation tool disposed within the tool lumen; and a second valve creation tool disposed within the tool lumen.

In some embodiments, the first valve creation tool is configured to be ejected into the slot when the second valve creation tool is extended past the distal port of the tool lumen.

In some embodiments, the system further includes a spring mechanism for ejecting the first valve creation tool into the slot.

In some embodiments, the proximal portion of the tool lumen in oval or oblong in cross-section.

In some embodiments, the distal portion of the tool lumen is circular in cross-section.

In some embodiments, the first valve creation tool comprises a retractable retractable stiffening mechanism.

In some embodiments, the retractable stiffening mechanism is a sheath or a wire.

In some embodiments, the first valve creation tool and the second valve creation tool both comprise expandable balloons.

In some embodiments, a method of creating two valve leaflets in a vessel is provided. The method can include inserting a catheter having a tool lumen into a lumen defined by a vessel wall; extending a first valve creation tool from the distal port and into a first location in the vessel wall, the first valve creation tool extending into but not through the vessel wall; rotating a distal portion of the catheter about a longitudinal axis of the catheter; extending a second valve creation tool from the distal port and into a second location in the vessel wall, the second valve creation tool extending into but not through the vessel wall; expanding the first valve creation tool within the vessel wall to create a first valve leaflet; and expanding the second valve creation tool within the vessel wall to create a second valve leaflet.

In some embodiments, the tool lumen comprises a distal port and a longitudinal slot extending proximally from the distal port.

In some embodiments, the method further includes ejecting the first valve creation tool through the longitudinal slot.

In some embodiments, the distal port is located on a first side of the catheter and an expandable element is located on a second side of the catheter opposite the first side.

In some embodiments, the method further includes expanding the expandable element before the step of extending the first valve creation tool from the distal port.

In some embodiments, the method further includes collapsing the expandable element before the step of rotating the distal portion of the catheter about the longitudinal axis of the catheter; and expanding the expandable element after the step of rotating the distal portion of the catheter about the longitudinal axis of the catheter.

In some embodiments, the method further includes collapsing the expandable element before the steps of expanding the first valve creation tool and expanding the second valve creation tool.

In some embodiments, the method further includes maintaining the relative longitudinal position of the catheter within the vessel while rotating a distal portion of the catheter about the longitudinal axis of the catheter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5a-5f illustrate an embodiment of a multi-lumen extrusion that is used for both the main balloon shaft and the delivery channels of a balloon catheter with delivery channels;

FIGS. 7a-7b illustrate another embodiments of a balloon with delivery channels where only the distal ends of the channels are fixed to the balloon;

FIGS. 8a-8b illustrate another embodiment of a balloon with delivery channels where the delivery channels have a longitudinally distensible section;

FIGS. 10a-10b illustrate embodiments of two catheter extrusion cross-sections;

FIGS. 11a-11f illustrate an embodiment of a device and method for the fixation of bicuspid valve leaflets;

FIGS. 13a-13c illustrate various embodiments of a delivery channel;

FIG. 15 illustrates an embodiment of a puncture element;

FIGS. 25a-25d illustrate an embodiment of a balloon having electrodes;

FIGS. 29a-34b illustrate various embodiments of a clamping mechanism;

FIGS. 36a-39c illustrate various embodiments of a double leaflet creation element catheter;

FIGS. 41a-42b illustrate an embodiment of a device with a flat and curved balloon.

DETAILED DESCRIPTION

Creation of and Geometry Monocuspid and Bicuspid Flaps:

A method for creating an autologous valve with a method for geometric fixation is described, along with several physical embodiments to achieve the described method. A device is inserted accurately into a vessel wall to a precise depth, such that the device does not extend through the full thickness of the vessel wall. An expanding mechanism is then used to separate from the vessel wall a thin flap. The space between the flap and the remaining portion of the vessel wall comprises a pocket, which can serve as a valve sinus.

Monocuspid

Figure 1B:
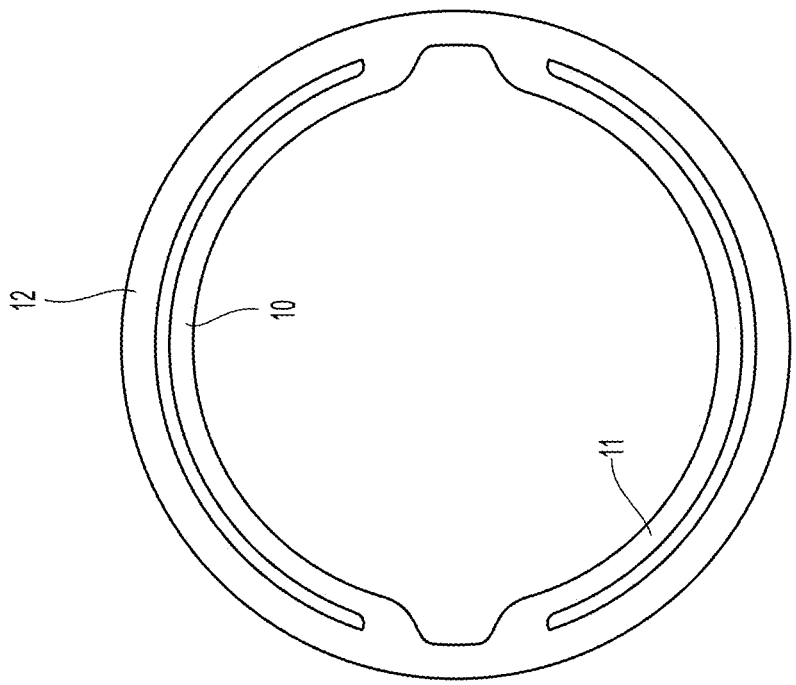
FIG. 1b depicts a bicuspid autologous valve geometry.
Figure 1A:
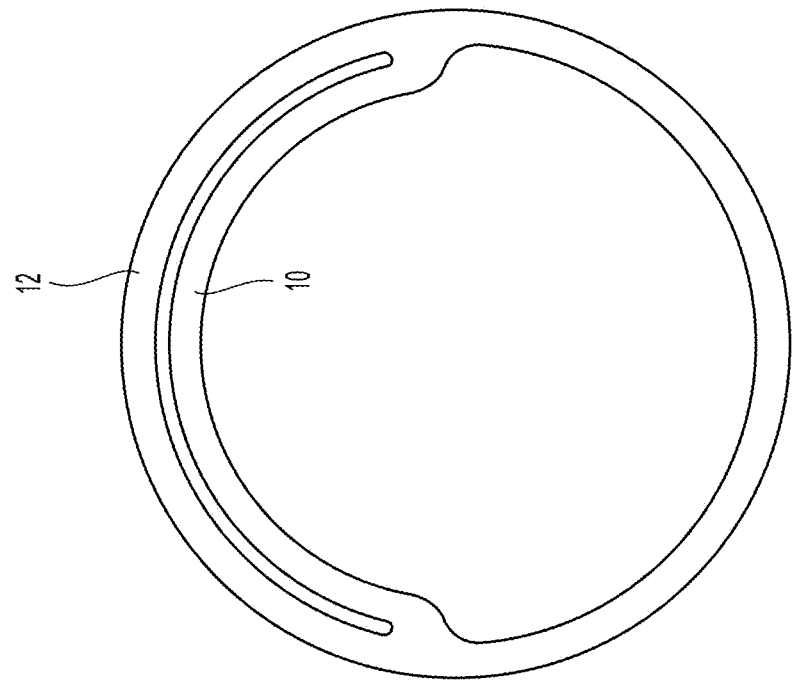
FIG. 1a depicts a monocuspid autologous valve geometry.

FIG. 1a depicts a monocuspid autologous valve geometry. This comprises a single flap 10 with separation from the vessel wall 12 (both at the mouth of the valve and along the sides of the pocket for most of its length). This separation may continue for at least about 180° of the entire vessel circumference and up to as wide as about 240° to properly create a competent leaflet.

Bicuspid

FIG. 1b depicts a bicuspid autologous valve geometry. This comprises two flaps 10, 11 with separation from the vessel wall 12 (both at the mouth of the valve and along the sides of the pocket for most of their length). This separation may continue for at least about 120° of the entire vessel circumference for each leaflet, and up to as wide as about 180° each to properly create a competent leaflet. In some cases the two leaflets may differ in width, with the total cumulative widths of both leaflets consisting of between 240° and 360° of the entire vessel circumference.

Tricuspid and above:

In some embodiments, it may be beneficial to have more than two valve leaflets. The width and depth of each leaflet would be smaller for each individual leaflet as the number of leaflets at a valve site increases.

Geometry of Fixation:

A device can also be used—either simultaneous with the creation of the autologous flap(s), or following flap creation—to fix the newly created valve flap to a portion of the vessel wall (monocuspid) or to another autologous leaflet (bicuspid) in specific orientations or locations to a) prevent the flap(s) from re-adhering to the portion of the vessel wall from which it/they came, and b) to fix the flap(s) in a semi-open position, so that refluxing blood forces the valve to close. It is very important to note, that the term fixation will henceforth be used to describe a welding of two tissue surfaces or a manipulation of the leaflets in such as way that both criteria listed above are fulfilled (e.g. tissue heating to cause leaflet shrinkage which prevents re-adherence and a fully closed leaflet position).

Figure 2E:
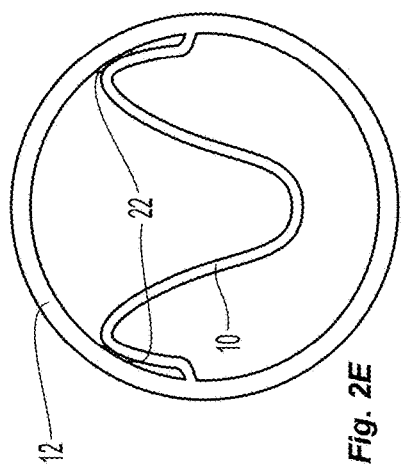
FIGS. 2e-2f illustrate an embodiment of a monocuspid fixation geometry using lines of fixation.
Figure 2F:
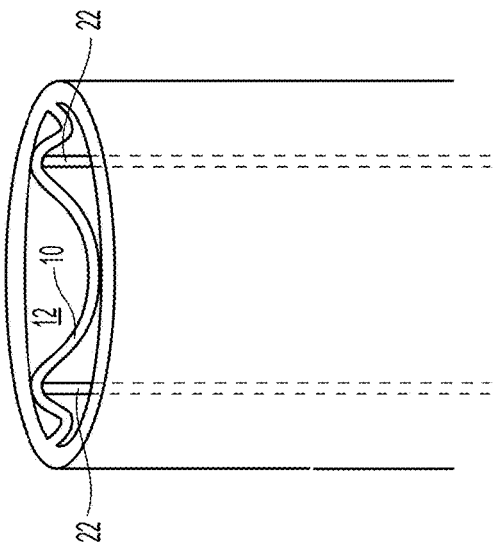
Figure 2C:
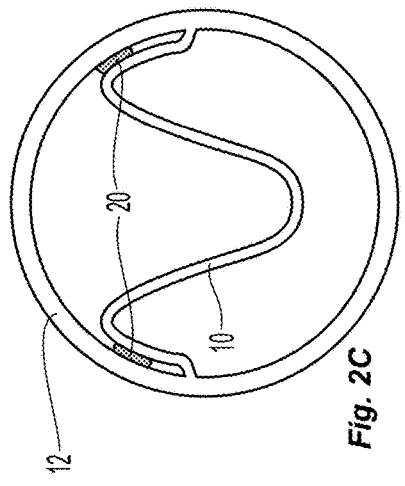
FIGS. 2a-2d illustrate an embodiment of a monocuspid fixation geometry using points of fixation.
Figure 2D:
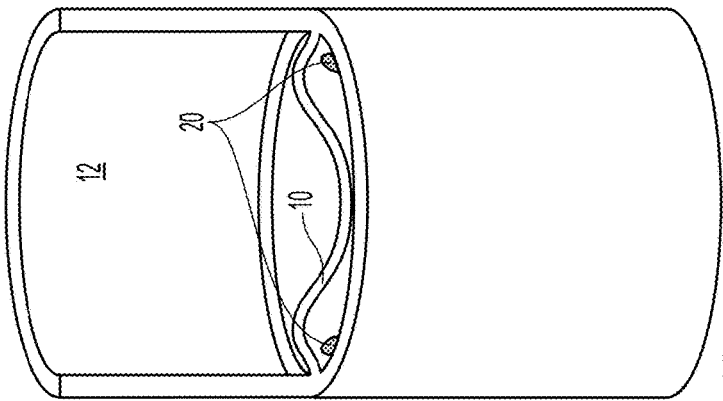
Figure 2A:
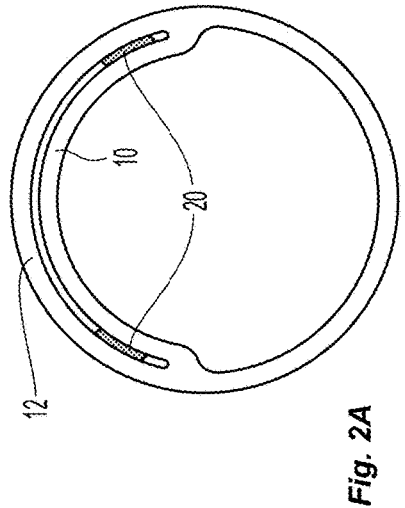
Figure 2B:
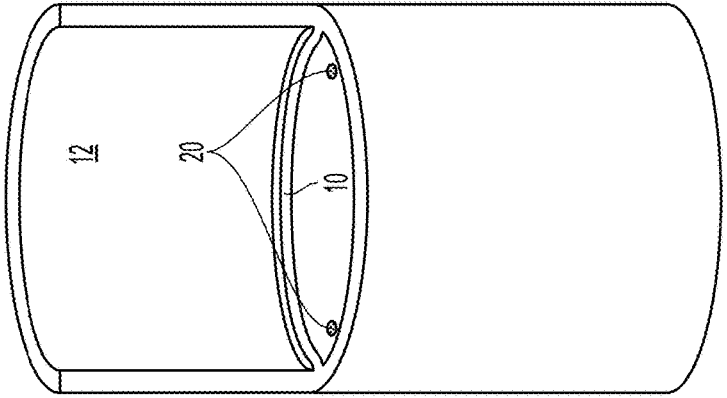

Monocuspid:

One embodiment of a monocuspid fixation geometry is shown in FIGS. 2a-2d, in which the leaflet is fixed in two locations, between about 1 mm and 5 mm from the top of the newly created tissue flap 10, and/or between about 0° and 45° from the edge of the lateral edge of the dissected flap. These depictions show discrete points of fixation 20. FIGS. 2a-2b depict the valve in the closed position, both from above and from an isometric view with a partial cross-sectional view of the vein. FIGS. 2c-2d depict the valve in the open position, both from above and from an isometric view with a partial cross-sectional view of the vein. FIGS. 2e-2f depict vertical lines of fixation 22 that can be used, which span about 0.5 mm to 20 mm (the vertical length of the flap at maximum), but remaining about the same angular distance from the lateral edge of the dissected flap 10 at all longitudinal positions. In other embodiments, the fixation lines may be slightly angled or curved lines of fixation.

Figure 2G:
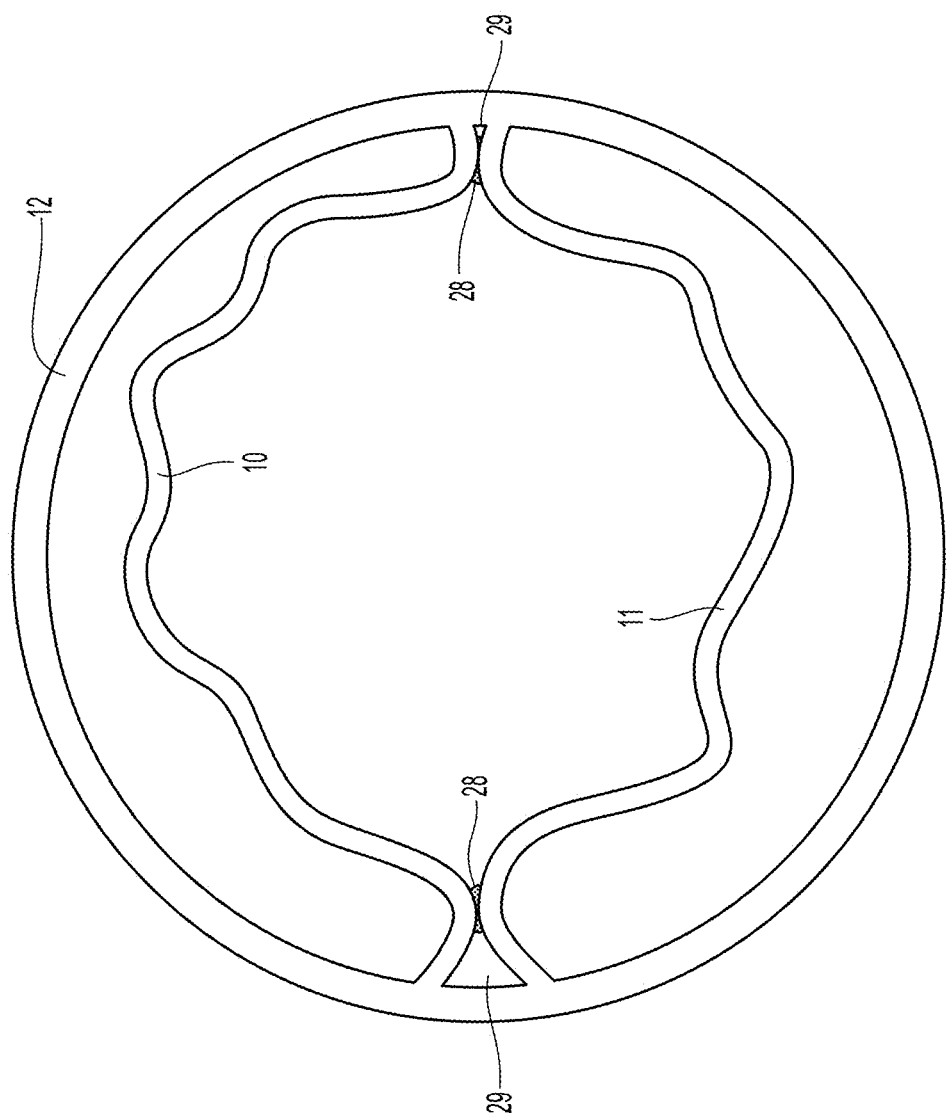
FIG. 2g illustrates an embodiment of a monocuspid fixation geometry.

Bicuspid:

Similarly, fixation can be created at discrete points of fixation 28 between two autologous flaps 10, 11 to form two leaflets as shown in FIG. 2g with the valve in the open position. As can be seen the fixation points are located near the commissures of the leaflets 29 (within about 0 mm-3 mm and/or within about 0° and 45° from the edges of the leaflets). These should also be placed between 1 mm and 5 mm from the top of each leaflet. In the case of bicuspid fixation, vertical lines of fixation can also be used as described above for the monocuspid case. In another embodiment, a single bicuspid fixation point or line may be placed in the middle of the flaps, creating two separate flow lumens as blood pumps through the valve in the open configuration.

In general devices described below for facilitating the fixation of autologous leaflets to vessel walls or to other autologous leaflets, can be used in the monocuspid case or the bicuspid case and should be thought of as interchangeable, regardless of how they are depicted.

Figure 3B:
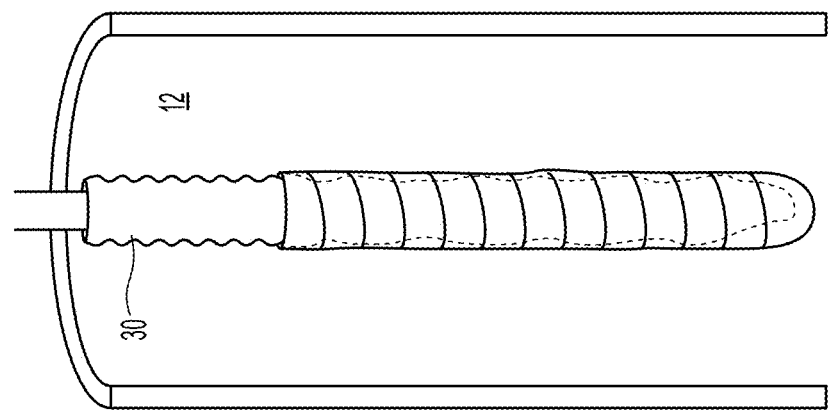
FIGS. 3a-3b illustrate an embodiment of a balloon that is expanded from within a sub-intimal plane of a vessel wall, thus creating a tissue flap.
Figure 3A:
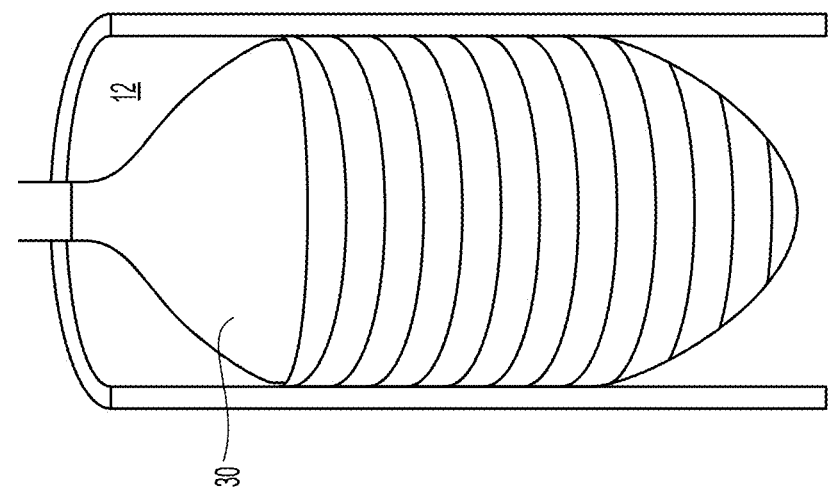

Apparatuses for Delivery of Leaflet Fixation Elements:

Many embodiments of delivery apparatuses described include a balloon 30 that is expanded from within a subintimal plane of a vessel wall 12, thus creating a tissue flap similar to that shown in FIGS. 1a and 1b. FIGS. 3a-3b depict an example of such a balloon 30 before (FIG. 3a) and after expansion (FIG. 3b). For many reasons, it is advantageous if the fixation of the leaflets can be delivered through or along the balloon catheter used for creating the leaflets. One advantage is it reduces the number of steps in the clinical procedure. The valve creation balloon 30 would not need to be removed for the introduction of a separate tool to deliver the fixation element. Additionally, fewer materials can be used, making manufacturing more efficient. Lastly, upon inflation of the valve creation balloon 30, it is possible to determine the location of specific locations on the leaflet, which may be utilized for fixation, with respect to the balloon and balloon catheter. This can be done by controlling the depth of insertion of the balloon into the wall, so that the operator knows that a certain location on the balloon corresponds to a certain distance from the insertion point (which will correspond to distance from the free edge of the valve). Additionally, the balloon can be rotationally oriented prior to entry into the wall (or after entry into the wall) such that a certain point on the balloon corresponds to a certain angular location on the newly created leaflet. Additionally, a balloon with a specific shape such as an ellipse or a square, can allow for self orienting balloons upon inflation, also allowing for one to one correspondence of locations on the balloon to locations on the newly created leaflet. Thus, this type of configuration may make the location of fixation more controllable and precisely determined.

The following embodiments can be configured to supply leaflet fixation in the form of a tissue bonding substance or adhesive, or in the form of a mechanical clip or suture. Or, in the form of RF tissue welding or manipulation.

Figure 4B:
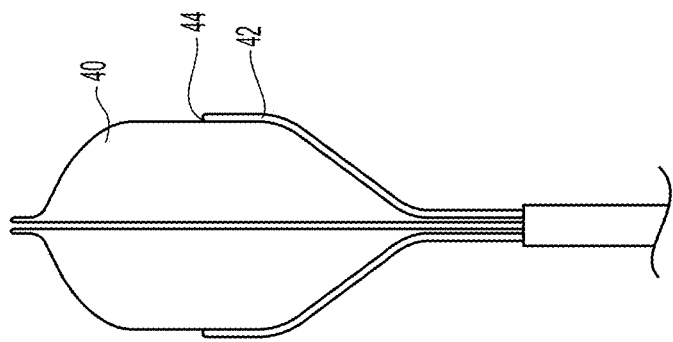
FIGS. 4a-4b illustrate an embodiment of a balloon with delivery channels.
Figure 4A:
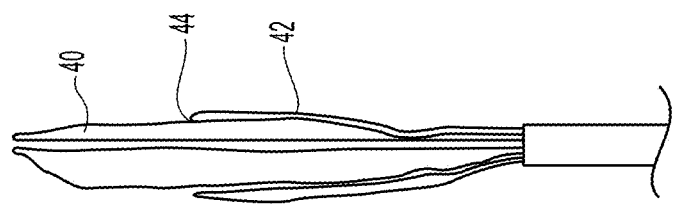

Additionally, the following elements can be configured to provide tissue fixation for the purpose of monocuspid valve fixation or bicuspid valve fixation. In many embodiments, as illustrated in FIGS. 4a-4b, the outer surface of the balloon 40 will contain 1 or more delivery channels 42 with internal lumens, fixed in a way to insure that when the balloon is inflated, the exit port 44 of these lumens are situated in a specific and consistent and predetermined location with respect to the surface of the inflated balloon. These delivery channels can be used to facilitate fixation of the mobilized intimal flap to inner surface of the opposing vessel wall or to another intimal flap.

In some embodiments, one multi-lumen extrusion 50 is used for both the main balloon shaft 51 and the delivery channels 52, as depicted in FIGS. 5a-5f. FIG. 5a depicts a cross-sectional view of the multi-lumen extrusion 50 at a location where the delivery channels 52 have been splayed away from the main circular cross section of the extrusion.

In some embodiments the delivery channels 52 can be biased towards the main catheter body to maintain a low profile during delivery and insertion. As depicted in FIG. 5b, just distal to this location, along the length corresponding to the where the delivery channels 52 have been pried off of the main extrusion, those experienced in techniques of catheter construction will understand that the main extrusion can be re-flowed into a circular form of smaller diameter while maintaining the internal lumens. This surface is adequate for the proximal and distal bonds for the balloon, as shown in FIG. 5c. FIGS. 5d-5f depict some other potential cross-sections of this tubing to be used for this catheter.

Other similar embodiments can be used to achieve the same basic shape and function involving slightly different manufacturing techniques. In one example, delivery channels are completely separate from the main shaft and are constructed from different materials and adhered to the main shaft. In other embodiments, the same material is used, but the channels are only adhered or fused in specific locations.

Figure 6C:
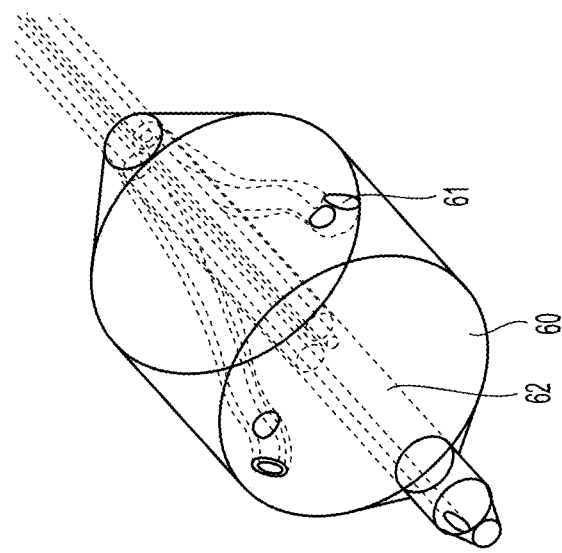
FIGS. 6a-6c illustrate another embodiment of a balloon with delivery channels.
Figure 6B:
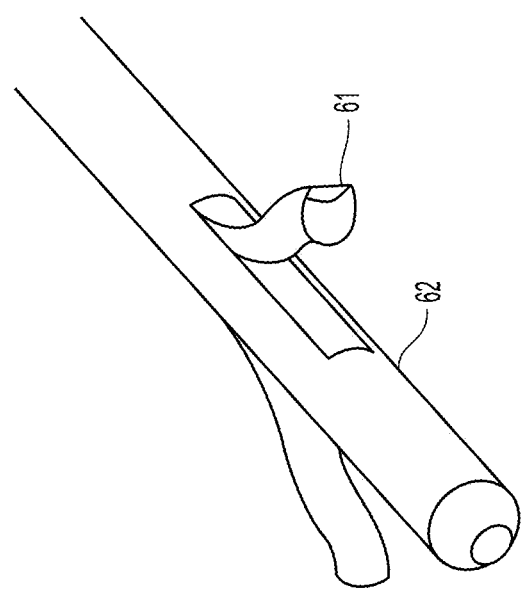
Figure 6A:
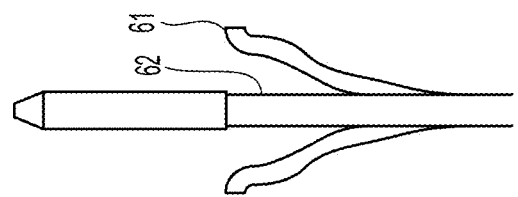

An alternate embodiment is shown in FIGS. 6a-6c, in which the delivery lumens 61 are internal to a balloon 60. As shown in FIGS. 6a, and 6b, the delivery lumens 61 can be constructed from the same extrusion as the main balloon shaft 62. As shown in FIG. 6c, upon adding the balloon 60, the distal sections of the delivery lumen 61 is glued to the surface of the balloon 60 such that they define a distinct boundary from the internal pressure cavity within the balloon 60. In this way, the delivery lumens 61 are completely distinct from the internal cavity of the balloon 60 and are open to the external room pressure.

In some embodiments, two external delivery channels—which are fluidly connected to an input port on the proximal end of the device—are adhered with glue, or another adhesive agent, or welded to the surface of the balloon at their distal section. With this constraint, as the balloon is inflated, the channels are forced to move distally along the length of the device in order for their distal end to move laterally with the inflating balloon. In one such embodiment (FIGS. 7a-7b), the channels 71 are only fixed to the device 70 at the distal end 72, and are free to move along the length of the device 70 such that the proximal ends 73 of these channels 71 physically move forward upon inflation near the back-end of the device 70. FIG. 7a depicts the deflated configuration, while FIG. 7b depicts the inflated configuration.

In another such embodiment (FIGS. 8a-8b), the channels 81 have at least a section of length that is longitudinally distensible 82, so that the proximal portion of the channels can be fixed to the proximal portion of the device 80, and the distal portion of the channels 81 can be bonded to the balloon, and the distensible section 82 is stretched during balloon inflation. Such distensible sections may have spring like configurations (as depicted), or other laser cut-able patterns in the shaft. Such distensible sections may be made from an intrinsically distensible material (a soft plastic or silicon). In a similar embodiment, the entire length of these channels is distensible. In both of these two embodiments, the material may be intrinsically distensible (a soft plastic or silicon) or may have a spring-like or accordion-like geometry that allows for distension at certain sections. FIG. 8a depicts the deflated configuration, while FIG. 8b depicts the inflated configuration.

Figure 9B:
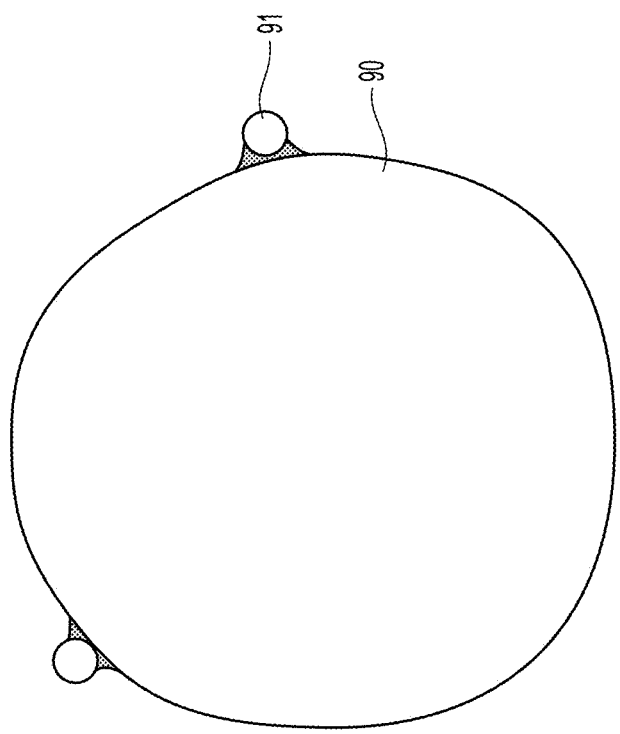
FIGS. 9a-9b illustrate an embodiment of a pleated balloon catheter with delivery channels.
Figure 9A:
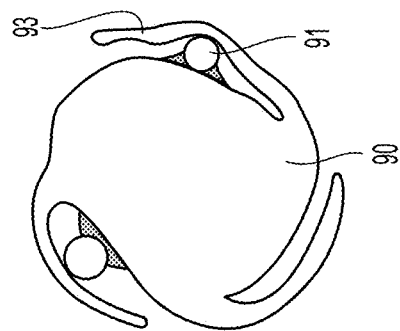

FIGS. 9a-9b depict one example of how these delivery lumens 91 may be adhered to the surface of the balloon 90 in the deflated (FIG. 9a) and in the inflated (FIG. 9b) configuration. As is shown, one or more pleats 93 can used to shield the delivery lumens 91 from getting caught on other structures during navigation, but also help to maintain a low profile and near circular cross section. In some embodiments, the pleats 93 can be arranged in a spiral configuration which can help maintain the low profile.

FIGS. 10a-10b depict two catheter extrusion cross-sections that can be used to create an intimal flap and deliver a tissue fixation device to the correct location on the flap. In FIG. 10a, the top lumen 100 is configured to accommodate a balloon with two delivery channels adhered to its surface. The bottom lumen 102 is configured to accommodate an apposition balloon to be used for catheter stabilization. In FIG. 10b, the top left lumen 100 is configured to accommodate a balloon with two delivery channels adhered to its surface. The bottom lumen 102 is configured to accommodate an apposition balloon to be used for stabilization. The lumen on the right can accommodate a visualization mechanism such as a scope 104. In similar embodiments, a regularly shaped circular lumen can accommodate the balloon with two delivery channels, if the channels are adhered within the folds or pleats of the deflated balloon, as illustrated in FIGS. 9a-9b, for example.

FIGS. 11a-11f depict a system for fixing two leaflets 110, 111 together with two leaflet engaging elements 112, 113. These valves may be natural valves or autologously created valves. In the embodiment depicted these leaflet engaging elements 112, 113 have a proximal end and a distal end and both are comprised of an expandable member 114, 115. In the embodiment shown, the expansion member is a balloon, but in other embodiments it may be a shape memory material or an expanding cage. As shown in FIG. 11a, both leaflet engaging elements 112, 113 are advanced into a separate but opposite valve sinuses while in the deflated configuration. Each leaflet engaging element 112, 113 has a leaflet facing surface, which is positioned to face inward toward the leaflet of its respective valve sinus. The first leaflet engaging element 113 is also comprised of a deploying feature, configured to deploy a leaflet fixation element 116. The deploying feature is positioned some predefined distance away from the distal end of the leaflet engaging element. This distance being less than the total length of the leaflet. As depicted in FIG. 11b, this deploying feature 117 may be comprised of a curved exit port, attached to a lumen that runs proximally back to the proximal end of the catheter. In other embodiments, this may be a strait lumen with a side port near the distal end. Alternatively, any of the deploying features described in this invention disclosure may be used as the fixation deployment feature in this configuration. The second leaflet engaging element 112 is comprised of a receiving element 118 to receive a fixation element 116, located a some predefined distance away from the distal end of the second leaflet engaging element 112. This distance being less than the total length of the leaflet. With both leaflet engaging elements 112, 113 placed into opposite valve sinuses, the deploying element and the receiving element should be more or less located at the same longitudinal position with the vein. As shown in FIG. 11c, Both leaflet engaging elements 112, 113 can be inflated (or expanded) so that both leaflets 110, 111 come together within the lumen of the vein. As shown in FIG. 11d, a fixation element 116, depicted here as a shape memory coil, is advanced out of the deploying feature 117 with use of a push rod (not pictured). It is then forced to puncture through the first valve leaflet and the second valve leaflet, curving due to its predefined shape memory into the receiving element 118 of the second leaflet engaging element 112. The receiving member 118 guides the fixation element 116 to curve back around at which point it may puncture through the leaflets again (as shown in FIG. 11e). Finally, the leaflet engagement members 112, 113 are deflated and removed leaving the fixation element 116 attached to both leaflets 110, 111 as shown in FIG. 11f.

Figure 12B:
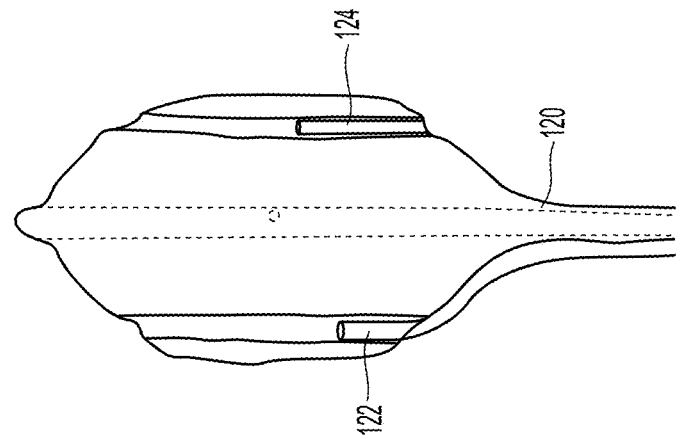
FIGS. 12a-12b illustrate another embodiment of a device and method for the fixation of bicuspid valve leaflets.
Figure 12A:
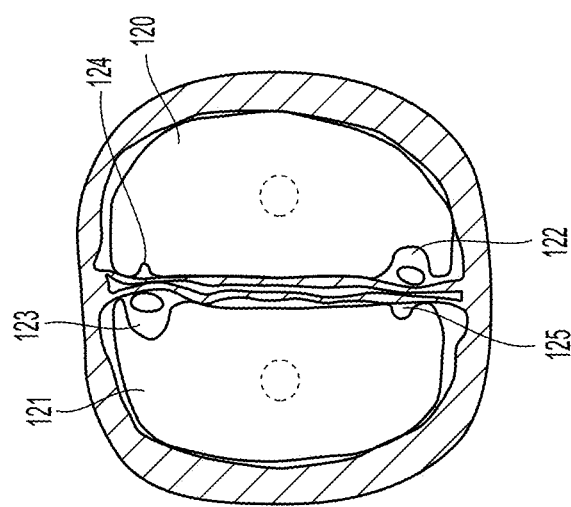

In a similar embodiment, two leaflet engaging members 120, 121 may be used, each with one deploying feature 122, 123 and one receiving feature 124, 125. As depicted in FIGS. 12a-12b, such an embodiment would allow for two fixation elements to be placed simultaneously or in series, yielding a valve geometry similar to that pictured in FIG. 2D. The deploying feature and the receiving feature can be spaced apart such that when the expandable element is expanded, the fixation elements are deployed near the valve commissures, as further described above. This embodiment can be used in a similar fashion to that described in the previous embodiment. Similarly, one leaflet engaging member can have two deploying features and the other leaflet engaging member can have two receiving features.

Use of Tissue Adhesive

In some embodiments, it is advantageous to deliver a tissue adhesive through the lumens of the described delivery channels. Cyanoacrylate has been shown to be useful at bonding internal surfaces of veins to each other, which is described in, for example, U.S. Pat. No. 8,475,492, which is herein incorporated by reference in its entirety. In general tissue adhesive can mean a glue of any kind that is biologically safe (e.g. cyanocrylate), a PEG polymer, or other sticky substances used for bonding two tissue surfaces.

Described are multiple embodiments of the geometry of the distal end of such delivery lumens configured to apply a tissue adhesive to a specific location in the anatomy. Most of these embodiments involve creating a small perforation in the intimal leaflet and potentially a small perforation partway or all the way through the vein wall or a second intimal leaflet. Then, a fixation agent is delivered through the delivery lumen and through the perforation in the intimal leaflet, to create adherence between two intimal leaflets (as shown in FIG. 2g) or between the side of the intimal leaflet not opposing the balloon, and the inside of the vessel wall (as was shown in FIG. 2a-2f).

In FIG. 13a, the distal most end of the delivery channel 130 is made from a hard material (such as SS or Peek), and includes a side port near the sharp edge of the distal face of the channel. Thus, when the balloon 132 is inflated, the distal edge 133 of the channel can puncture the intimal leaflet, and access to that perforation is gained through the sideways facing delivery lumen exit port 134. In a similar embodiment (not depicted), the distal exit port of the delivery lumen is at the distal face of the delivery channel and is oriented forward along the same axis as the channel itself. In FIG. 13b the distal most end of the delivery lumens have a sharp protrusion 135 directed away from the surface of the balloon 132. Once inflated, the point is directed nearly perpendicularly to the surface of the inflated balloon 132 so that it can puncture at least the intimal leaflet and potentially into or through the rest of the vein wall layer as well. For example, the sharp protrusion can have a length of between about 0.1 mm to 3.0 mm. In some embodiments, the sharp protrusion can have a length of about 0.5 mm-1.5 mm. In some embodiments, the protrusion can be angled between about 0 to 45 degrees from the normal axis. In the embodiment depicted, the internal lumen of the delivery lumen is directed throughout the sharp point, which can be perpendicular or angled. For example, in some embodiments, the exit port of the lumen is directed perpendicularly outward from the surface of the inflated balloon. In the embodiment depicted, the embodiment could be built by bending a very small needle about 90° or between about 60 to 120 degrees with a very small radius of curvature, very close to the distal point. FIG. 13c depicts a similar embodiment, except the internal lumen terminates out of a sideways facing port 136 near the distal end of the delivery channel 130, and a perpendicularly directed puncture element 137 is present at the distal end of the delivery channel (to puncture the intimal leaflet). In a similar embodiment, the exit port pay even be a forward facing exit port at the distal end of the delivery channel, and a separate puncture mechanism can be adhered to the balloon just distal to the exit port. In some embodiments, the protrusions or puncture elements can be covered by, for example, a sleeve before expansion of the balloon.

Figure 14C:
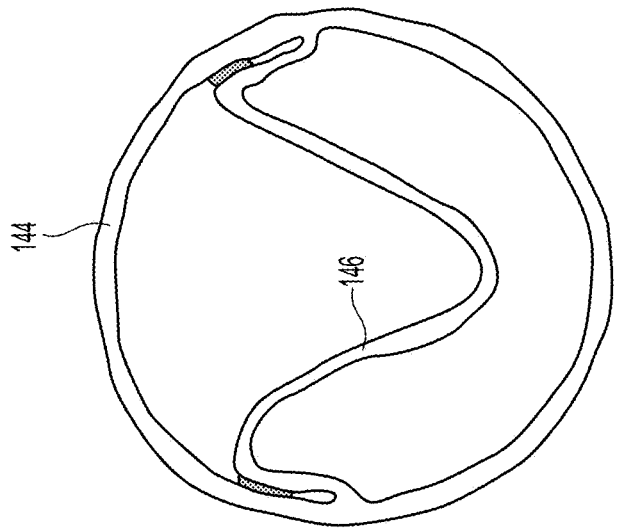
FIGS. 14a-14c depicts a view of how some of the puncture method embodiments would work with an inflating balloon to create a fixed monocuspid valve geometry.
Figure 14B:
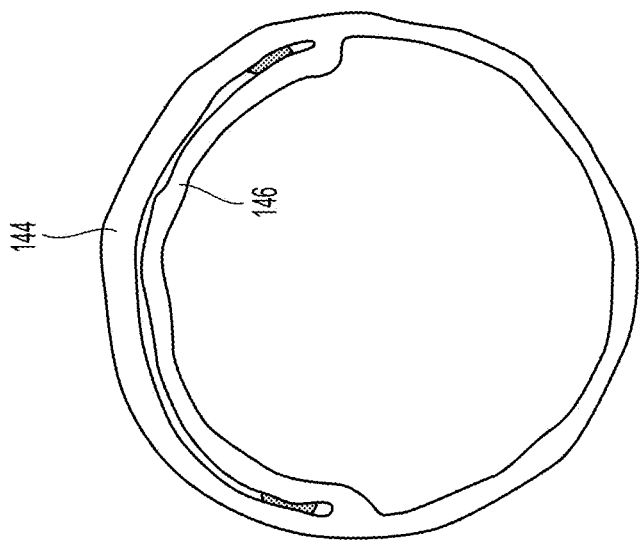
Figure 14A:
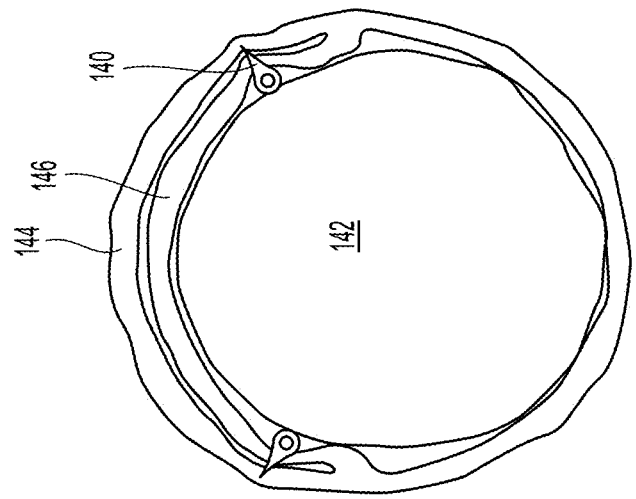

FIGS. 14a-14c depicts a view of how some of these puncture method embodiments would work with an inflating balloon to create a fixed monocuspid valve geometry. As shown in FIG. 14a (from above), once the balloon 142 is fully inflated, the puncture elements 140 have been pressed against the vessel 144 or leaflet wall 146 and have punctured through the full thickness of the intimal leaflet, and has entered into some (or all the way through) of the bordering vessel wall. Once this puncture track has been made, a fixation element such as a tissue glue, or adherent PEG is delivered through the delivery lumen within the delivery channels, leaving a thin layer of a sufficient amount of fixation agent between the intimal leaflet and the vessel wall. The balloon would be left inflated for between 10 seconds and 500 seconds, depending on the curing time of the fixation agent. FIG. 14b depicts the fixation geometry in the closed valve position, once the device is deflated and removed. FIG. 14c depicts the fixation geometry in the open valve position.

A similar device could be used to create a bicuspid fixation geometry. The only difference would be the balloon would be inflated as shown in a location in the vessel where two leaflets exist (FIG. 1B). Thus, the puncturing elements would puncture through one leaflet, and butt into and potentially penetrate the second leaflet. At this point, adhesive would be delivered through the first leaflet, and into the the space between the leaflets, while the balloon is inflated to hold contact between the leaflets during fixation. Alternatively, the device illustrated in FIGS. 14a-c can be used to fix a first leaflet as described above, and then deflated and rotated and used again to fix the second leaflet, or the device can be used to fix one side of each leaflet, and then rotated and be used to fix the other side of each leaflet. Alternatively, the device can have additional puncturing elements, for example four, so that the device can simultaneously be used to fix both leaflets.

FIG. 15 depicts a similar embodiment, except a puncture element 152 which is built to slide within the lumen of the delivery channel 150, can be advanced out of the distal end of the lumen and into or through the two opposing tissue layers. In one such embodiment, the puncture element 152 is itself a curved needle with a delivery lumen inside it (for delivery of a fixation agent during tissue puncture). In another embodiment, the puncture element is a curved needle with a distal exit port and/or one or more side-ports within the distal 1-5 mm of the needle. In another such embodiment, the puncture element is simply a curved cylindrical rod with sharpened distal end. In this embodiment, the fixation agent is coated along the outside of the puncture element, so that it can be left behind and within the tissue puncture track. The puncture element in these embodiments could be made from preformed SS, or a hard plastic such as peek, or shape-set nitinol. In some embodiments, the needle can include a stop to control the puncture depth.

In another embodiment, the distal end of the delivery lumen is sharp and designed to puncture through the intimal leaflet (as previously described), and a separate slidable inner member coated with a tissue adhesive is advanced through the exit port of the delivery lumen and through the hole in the intimal leaflet. It is then retracted, leaving tissue adhesive behind to adhere the two layers together.

Figure 16C:
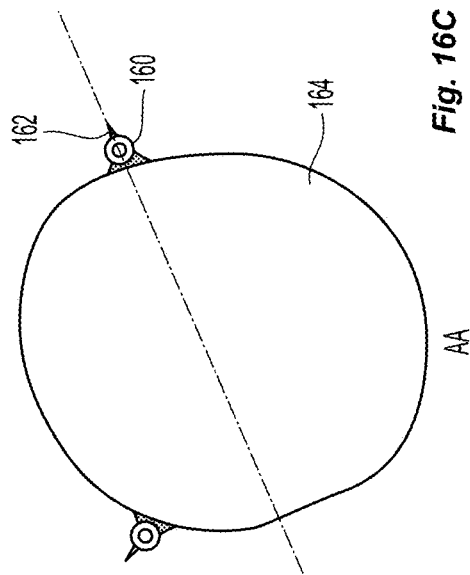
FIGS. 16a-16d illustrate an embodiment of a delivery channel with multiple puncturing elements.
Figure 16D:
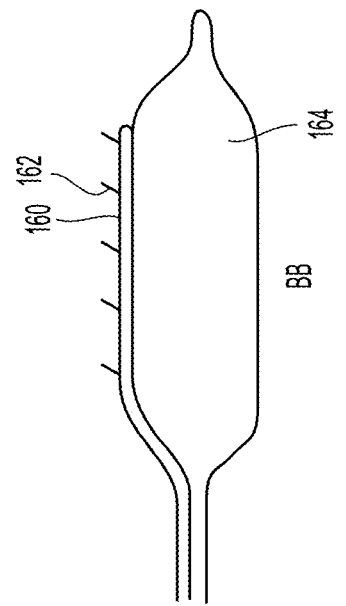
Figure 16A:
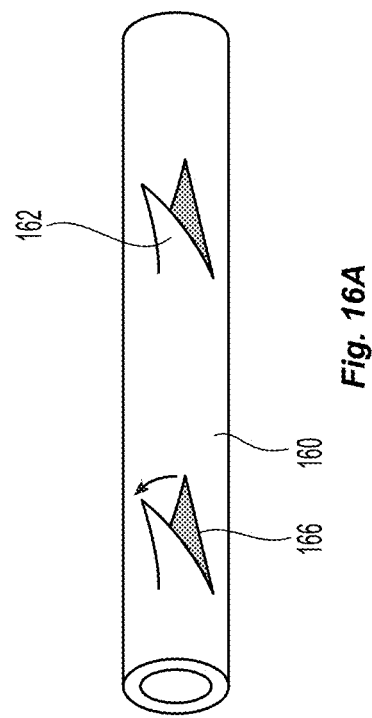
Figure 16B:
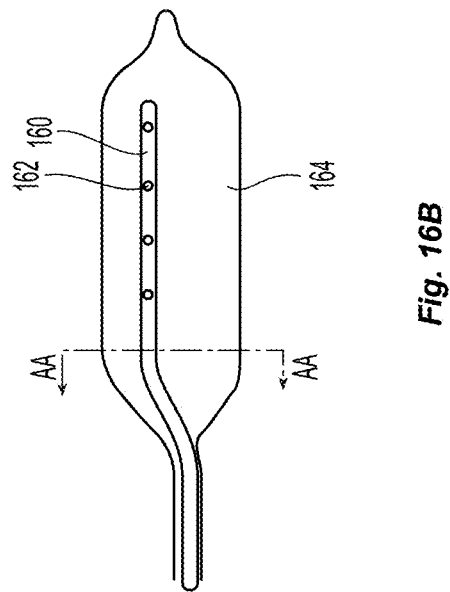

In some embodiments, as depicted in FIGS. 16a-16d, the delivery channels 160 are comprised of multiple puncturing elements 162 with near perpindicular orientation with respect to the lumen of the delivery channel 160. These puncture elements 162 are positioned along the length of the balloon 164 in a nearly strait line with respect to the axis of the balloon shaft. In another embodiment, the puncture elements are positioned along the length of the balloon along a curved geometry to distribute the adhesion points in different radial positions. These puncture elements 162 are accompanied by side ports 166 connecting to the inner lumen of the delivery channel. In one such embodiment depicted in FIG. 16a, these puncture elements 162 and side ports 166 are created by using metal delivery channels, and bending a triangular section of the delivery channel upward to near 90 degrees creating a side port 166 in the delivery channel 160 connecting to the inner lumen, and a puncture element 162. FIG. 16b depicts the balloon 164 from a side angle, looking straight down onto the puncture elements 162. FIG. 16c, depicts the cross-sectional plane AA called out in FIG. 16b, which shows the balloon surface, and two delivery channels 160 adhered to it. Puncture elements 162 are shown pointing outward from the delivery channels 160. FIG. 16d depicts the cross-sectional plane BB, referenced in FIG. 16c, in which the puncture elements 162 can be seen pointing outward from the surface of the balloon 164. This embodiment, and ones similar to it, can be used with the following method: once in the sub-intimal space, the balloon is inflated, which creates multiple punctures in the intimal leaflet. A tissue adhesive is then injected through the delivery channel such that some of that adhesive is fed through the newly created holes in the intimal leaflet, and into the space between the leaflet and the opposed vessel wall. Once cured, this leaflet is adhered along tissue bond lines (as depicted in FIGS. 2e-2f).

In other types of embodiments, a tissue adhesive is used that can permeate through the intimal leaflet layer of tissue and adhere the opposing side of the leaflet to the vessel wall. This can be done with the embodiment device depicted in FIGS. 7a-7b, in which such a tissue adhesive is simply supplied to the tissue through the delivery channel after inflation of the balloon. This method requires no puncture of the intimal leaflet.

Figure 17C:
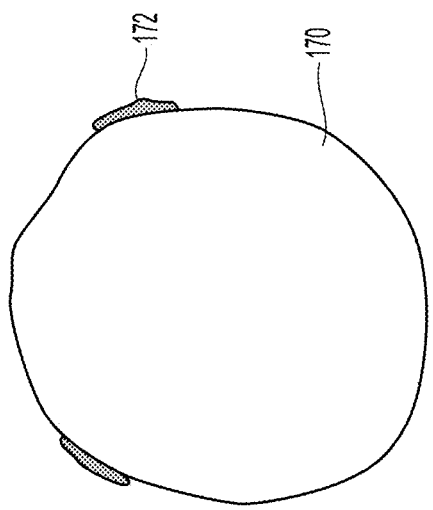
FIG. 17a-17d illustrate embodiments of a balloon coated with a tissue adhesive.
Figure 17D:
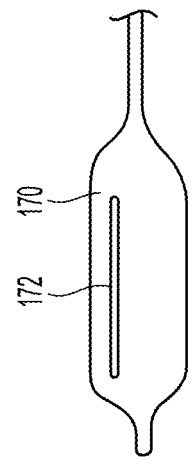
Figure 17A:
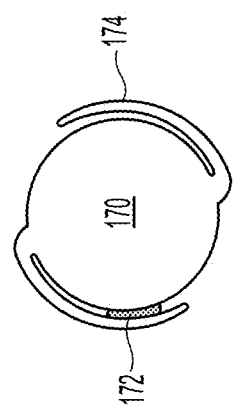
Figure 17B:
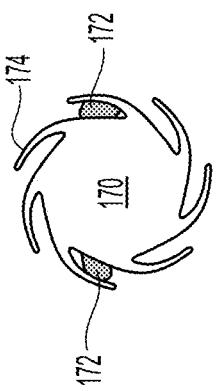

In a similar embodiment, as depicted in FIG. 17a-17d, the balloon 170 is pre-coated with a tissue adhesive 172 such as cyanoacrelate or PEG polymer in one (FIG. 17a), or more locations (FIG. 17b) such that pleats 174 of the balloon 170, which can be wrapped in a spiral configuration, hide the tissue adhesive from contacting other aspects of the catheter or the vasculature, until the balloon has been fully inflated. In such an embodiment, the balloon may be teflon coated or otherwise coated so that the adhesive agent does not stick to the surface of the balloon. After inflation, as depicted in FIG. 17c-17d, the balloon 170 has tissue adhesive 172 in two or more specific locations (either points or lines) exposing the adhesive to the inner surface of the intimal leaflet. The tissue adhesive is then able to permeate through the intimal leaflet layer and adheres the leaflet to the vessel wall.

Figure 18B:
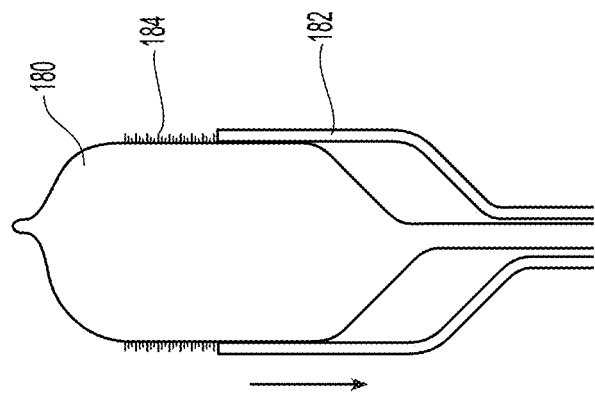
FIGS. 18a-18b illustrate an embodiment of a balloon with retractable delivery channels.
Figure 18A:
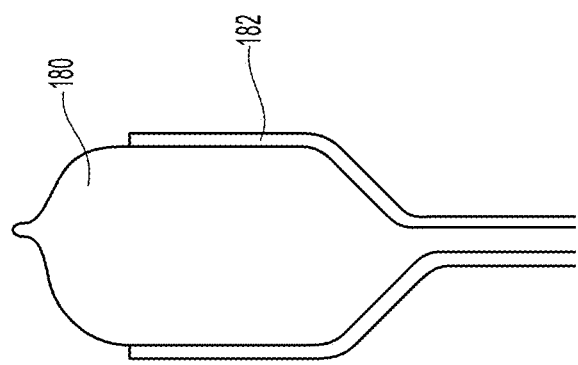

In another similar embodiment, as depicted in FIGS. 18a-18b, a balloon 180 with retractable delivery channels 182 is inflated to create an intimal leaflet. It is then deflated slightly, and a tissue adhesive 184 is injected onto the surface of the semi-inflated balloon as it is retracted to leave a line of adhesive on the surface of the balloon. It is then fully inflated within the pocket to deposit the adhesive on the tissue and create the desired tissue adhesion line.

Figure 19C:
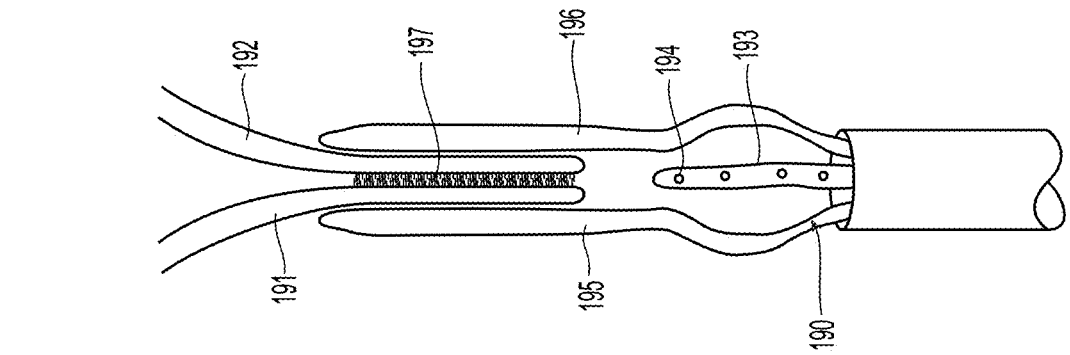
FIG. 19a-19c illustrate another embodiment of leaflet fixation using tissue adhesives.
Figure 19B:
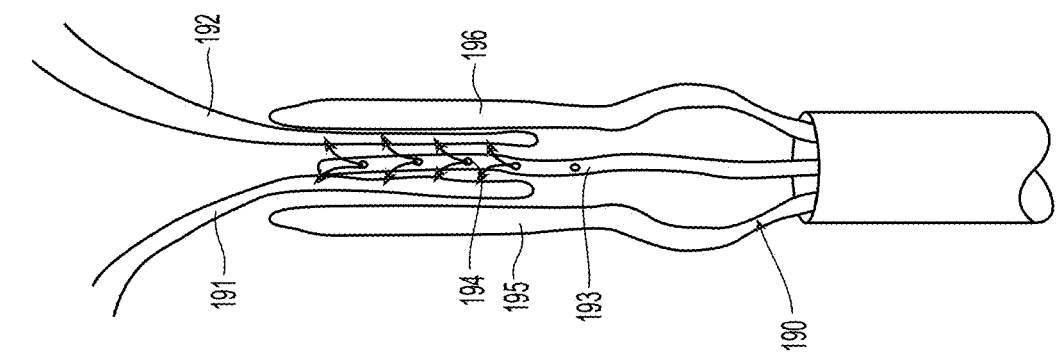
Figure 19A:
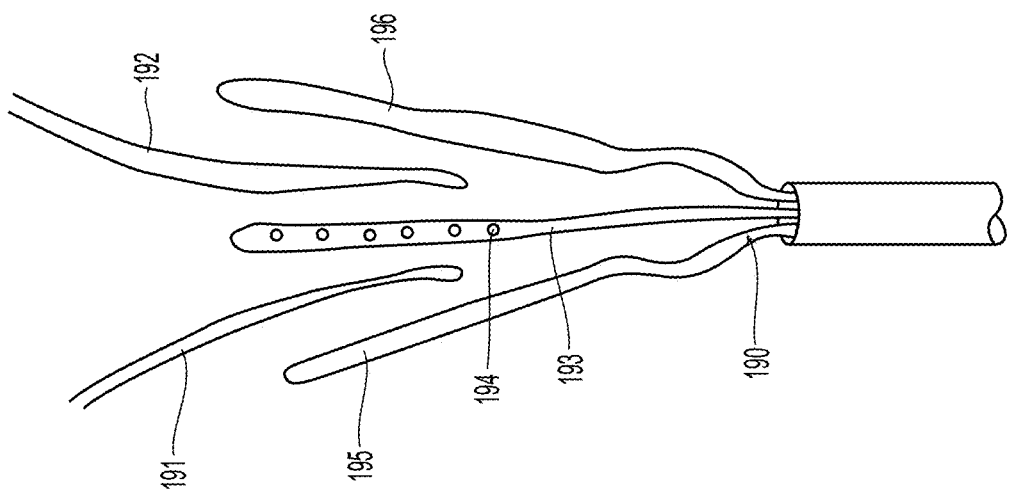

One method for affixing two autologous leaflets together with a tissue adhesive is depicted in FIGS. 19a-19c. In some embodiments, a clamping instrument 190 is used to capture the two opposing leaflets 191, 192 and bring them into contact with each other prior to or during the application of glue (FIG. 19a). Also comprised in this embodiment is a tissue adhesive application appendage 193, which is positioned between the two leaflets. As depicted this glue application appendage 193 has multiple exit ports 194, but could have just one, or one or more long narrow slits for glue application. After the clamping arms 195, 196 have captured the leaflets, a tissue adhesive 197 is ejected from the exit port(s) and is captured in the space between the two leaflets. FIG. 19c depicts retraction of the appendage 193 after injecting a tissue adhesive 197, while the clamping arms 195, 196 remain clamped on the tissue for a discrete amount of time to facilitate the curing of the bond. The clamps can be designed to ensure the tissue contact geometry can be made to be consistent, as well as the normal force experienced between the leaflets. The clamps can then be released, and the device can be removed from the vasculature. This clamping instrument can be delivered to the leaflets in all the same ways that were described for the tissue welding clamps.

Mechanical Means of Fixation

The same or similar configurations can be used to deliver mechanical means of fixing intimal leaflets against a vascular wall in specific locations. As previously described, a balloon can be used in combination with one or more delivery channels to gain access to specific locations in the tissue, as dictated by their relation to the surface of the inflated balloon.

Figure 20B:
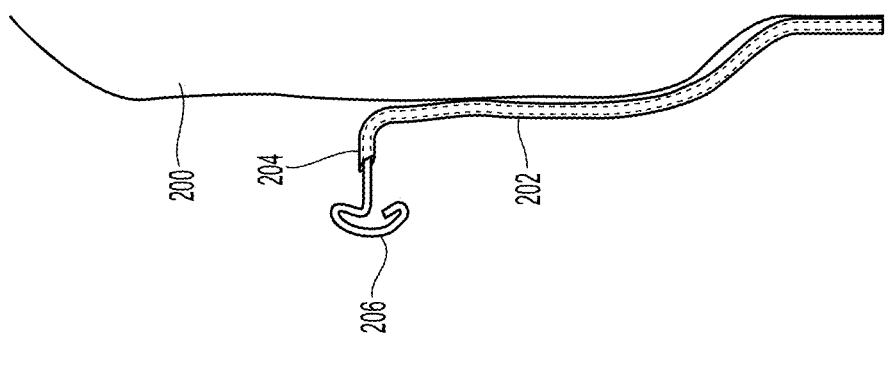
FIGS. 20a-21c illustrate an embodiment of leaflet fixation using a tissue anchor.
Figure 20A:
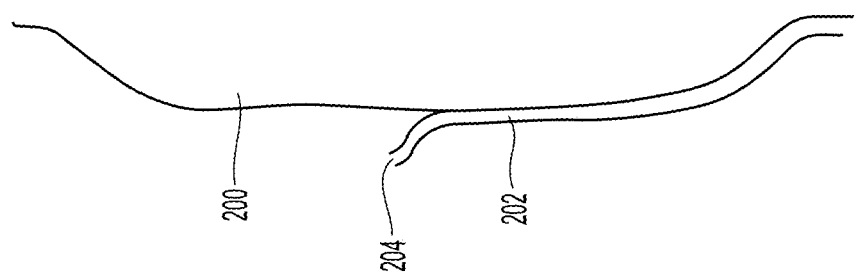

FIG. 20a depicts the surface of an inflated balloon with a delivery channel with a curved, sharp distal end 204. In this case, the puncture depth is sufficient to puncture through the intimal leaflet and the entire thickness of the vessel wall. This can be adhered to the surface of the balloon and configured with the rest of the catheter in the same ways as previously described. Within the lumen of the delivery channel 202, a shape memory tissue anchor 206 which can be implanted into the body is loaded. The anchor can have a deployed configuration of a proximal end, a distal end and body portion in between, where the proximal and distal ends are wider or have a greater transverse dimension than the body portion. In the delivery configuration, the anchor 206 can be linear, for example, for easy of delivery through a lumen. A push rod on the back end of the device, allows the anchor 206 to be pushed out of the distal bevel of the delivery channel, allowing it to take its shape (FIG. 20b).

Figure 21C:
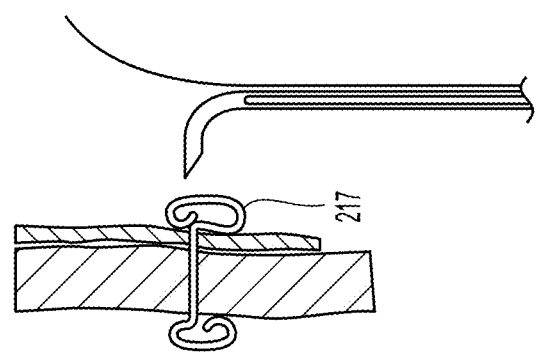
Figure 21B:
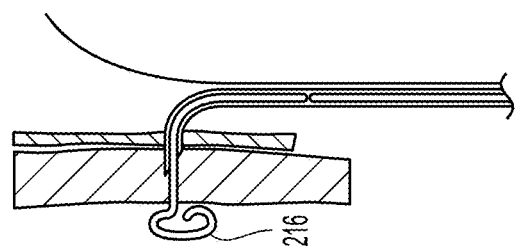
Figure 21A:
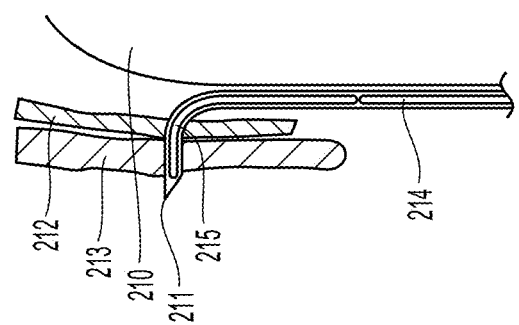
Figure 22A:
FIGS. 22a-22g illustrate various embodiments of tissue anchors.
Figure 22B:
Figure 22C:
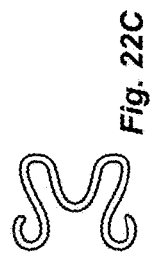
Figure 22D:
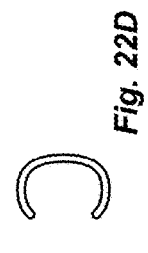
Figure 22E:
Figure 22F:
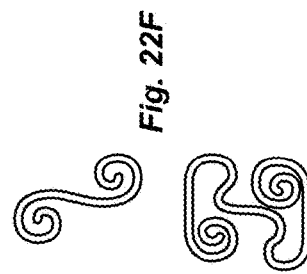
Figure 22G:
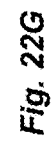

The mechanics of this method are described in FIGS. 21a-21c. FIG. 21a depicts the balloon 210 fully inflated, which pushes the puncture element 211 of the delivery channel through the leaflet 212 and the vessel wall 213. At this point, a pusher 214 would be advanced within the lumen of the delivery channel, which acts to push the distal end 215 of the tissue anchor out of the distal port of the delivery channel. Due to its self expanding and/or shape memory properties, it opens up into a predetermined shape 216, and takes up space outside of the vessel wall (not depicted). FIG. 21b depicts the beginning of balloon deflation, which pulls the puncture element out of the vessel wall, leaving behind the crossbeam of the tissue anchor. FIG. 21c depicts the balloon fully deflated, which has pulled the puncture element through the entire vessel wall and through the intimal leaflet. Once it is retract a certain distance from the wall, the back end of the tissue anchor is freed from the distal port of the delivery channel and takes shape 217 within the vessel lumen on the opposite side of the intimal leaflet. This can also be accomplished by advancing the push rod sufficiently to dislodge the tissue anchor. Once completed, the anchor forces the intimal leaflet to remain affixed to the corresponding location on the vessel wall. Alternatively, this method could be used with two opposing leaflets as opposed to one leaflet and a vessel wall. This would attach the two leaflets together.

FIGS. 22a-22g depict multiple geometries for shape memory tissue anchors 220, which can be used in much the same method as previously described. In general, all of these anchors are made from Nitinol or another shape memory material. Once deployed, they are designed to resist being straightened out, so that they can hold the two tissue layers in close proximity. The distance between the two ends of anchors (usually separated by a crossbeam) dictates how closely the two layers are held together.

Other embodiments include tissue anchors that function more like a screw, and are inserted into the wall from similar delivery lumens through a rotational advancement. For example, the anchor can have a coiled or spiral configuration. In some of these embodiments, the delivery channels have puncturing elements (as depicted in previous figures). In other embodiments, a side port is used, out of which a rotational anchor is deployed at an angle near perpendicular to the surface of a balloon or expandable member.

Bicuspid:

One method for affixing two autologous leaflets together near the commissures using a tissue clip is described. A small implantable clip that could hold two leaflets together with sufficiently small size to prevent a immunologic response or to be a embolic risk to the patient. The clip could be made from any metal not hazardous to humans. Most notably it be made from Stainless Steel (SS) or Nitinol.

In some embodiments a SS clip is used as a staple, in that it is deformed through the tissue to permanently yield in a position that holds the leaflets together appropriately.

In some embodiments a Nitinol clip is used that reverts to its natural shape with the removal of a retraining force (a sheath) once in the correct position in a way that grabs the tissue and holds the leaflets together sufficiently.

Figure 23A:
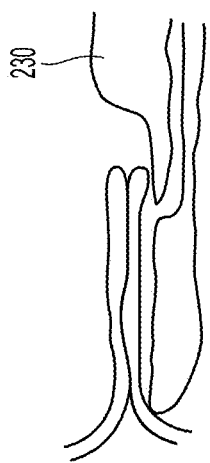
FIGS. 23a-23c illustrate an embodiment of bicuspid leaflet fixation using a clip.
Figure 23B:
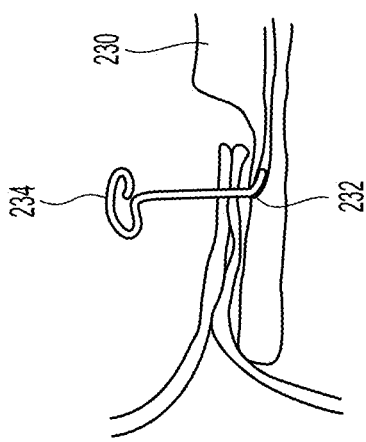
Figure 23C:
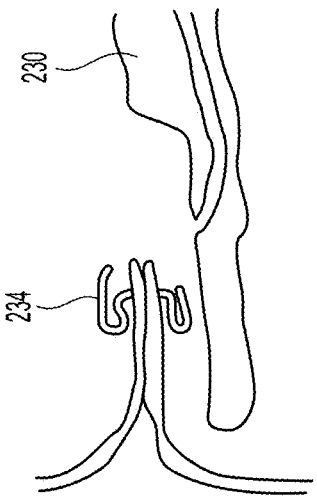

In one potential clip delivery embodiment (as shown in the FIGS. 23a-23c), a curved needle 232 is advanced through a lumen and out of a side port along the surface of the blunt distal end of the valve creation catheter 230, such that it penetrates both leaflets. A shape memory clip 234 can then be advanced through the hollow lumen of the needle. Then, when the needle is retracted, the shape memory clip 232 coils up to capture the two leaflets together.

Tissue Welding or Heating:

One method for fixing two autologous leaflets together near the commissures or a monocuspid leaflet to a vessel wall, is a tissue weld or heat manipulation. Tissue weld could be accomplished by delivering heat in the form of Bipolar RF energy, monopoloar RF energy, conductive heat transfer (cautery), steam, laser, non-laser light energy, or others. As energy is delivered to the tissue, a weld will occur via denaturing of proteins at a relatively low temperature (~37 degrees C.), as compared to the higher temperatures required for ablation or cutting. An advantage of this approach is that it does not require the implantation of any foreign material, which may hold better clinical outcomes.

Figure 24B:
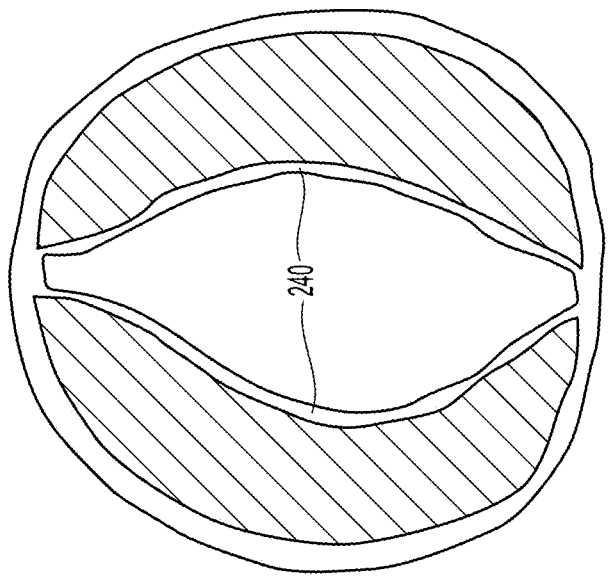
FIGS. 24a-24b illustrate an embodiment of heat shrinking valve leaflets.
Figure 24A:
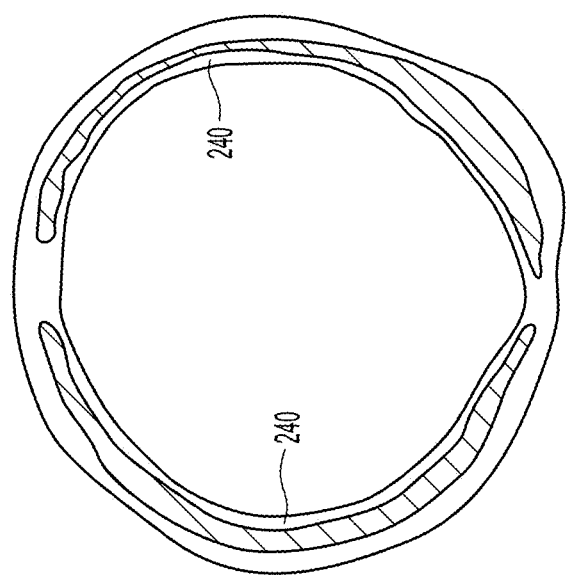

Similarly, a heat source such as RF energy can be used to shrink the leaflet tissue, as is known to happen (RF vein closure), in such a way to cause the leaflets to be fixed in a semi-open position. As can be seen in FIGS. 24a-24b, the length of the tip edge of the valve leaflets 240 is shrunk from nearly ½ vein circumference (FIGS. 24a) to 1-1.5 vein diameter (FIG. 24b). The belly of the leaflet(s) (lower down from the top edge of the valve) are not effected by the heat, and still have size and the mobility to fully occlude the vein in the closed position. In doing this, even though the leaflets 240 have not been welded together, they still achieve the criteria of a fixed valve as described in this application. The advantage of such an approach is that the durability of the valve does not rely on the durability of a weld, which could fail over time if not done with the correct parameters. Also, this approach does not require an implant. This could also be done with a monocuspid valve. In some embodiments, selected portions of the leaflet are heated or receive additional heat treatment to selectively shrink portions of the leaflet. For example, the central portion or the edges of the leaflets can be selectively heated and shrunk. In some embodiments, the entire leaflet is heated and shrunk.

In some embodiments, the RF energy or another type of heating is delivered to the tissue by the valve creation balloon catheter. In one particular embodiment shown in FIGS. 25a-25d, a valve creation balloon 250 is equipped with electrodes 252 on the surface of the balloon material. When in the deflated position (FIGS. 25a-25b), the RF electrodes 252 fold up in some efficient way into the material of the balloon 250. When in the inflated position (FIGS. 25c-25d), the electrodes 252 are mobilized to face outwardly toward the tissue in specific locations with respect to the catheter shaft. As is shown, the electrodes 252, which can be made from a stiff metallic material, can narrow so that they can take up very little space on the deflated balloon 250. Balloon electrodes may range from between 0.010" wide and 8 mm wide. In one utilization of this design, monopolar RF energy can be delivered from the electrodes on the balloon to heat the leaflet as needed.

If thicker electrodes are required to achieve the desired effect in the tissue, a compliant conductive material can be used which can expand with the inflation of the balloon.

Figure 26B:
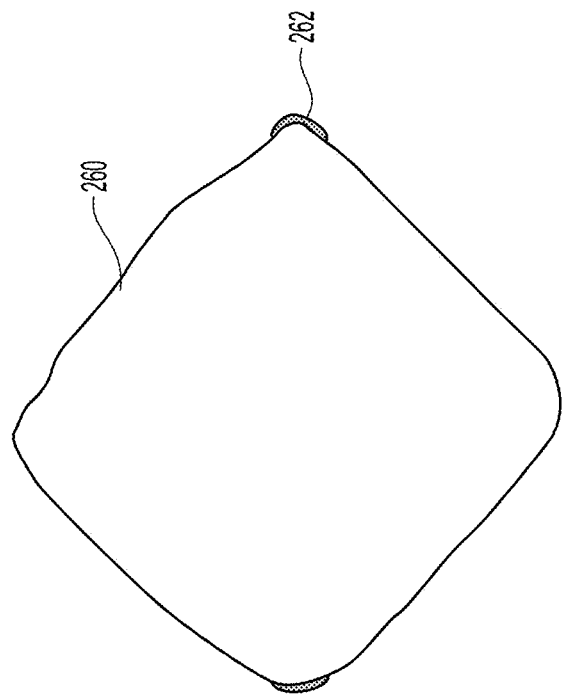
FIGS. 26a-26b illustrate embodiments of various balloon geometries.
Figure 26A:
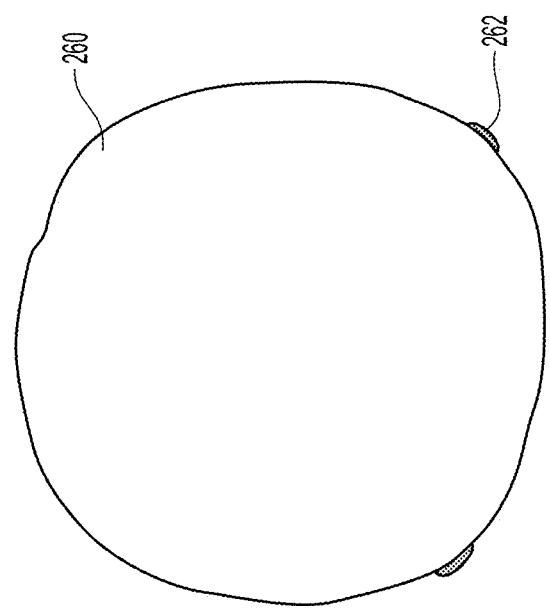

FIGS. 26a-26b show a few other balloon 260 shapes and electrode 262 configurations that can be used in a similar way. A circular balloon may allow for more efficient stretching of the leaflet during creation. A square shaped balloon may allow for self-orientation of the balloon during inflation, so that the electrodes are positioned in the commissures of the valves.

Figure 27B:
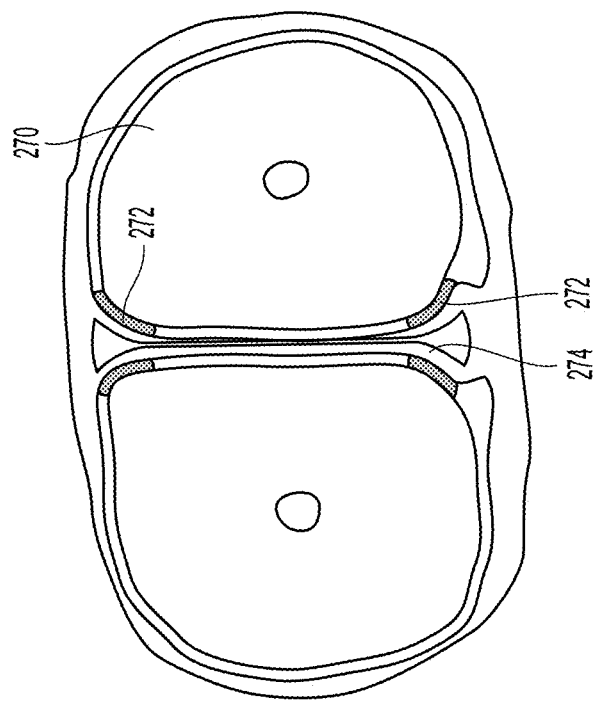
FIGS. 27a-27b illustrate the use of two energy delivery balloons to create bipolar energy delivery.
Figure 27A:
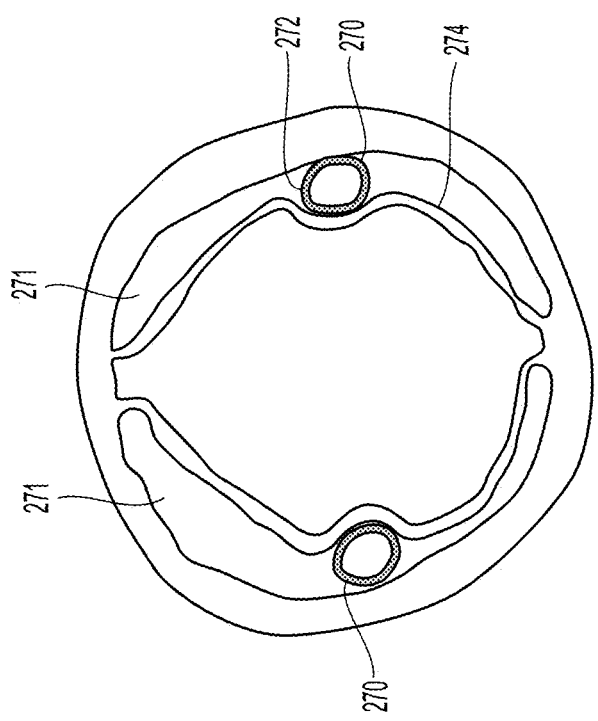

FIGS. 27a-27b depict the use of two such energy delivery balloons 270 to create bipolar energy delivery. As shown in FIG. 27a, two deflated balloons 270 are placed within the sinus 271 of two autologously created valves (or in the case of autologous valve creation with the same balloon, are placed within the vein wall about 180 degrees apart from each other). As is shown in the figure, the electrodes 272 on the surface of the balloons are directed to a specific location on the leaflets 274 upon inflation of the balloons 270, which can be inflated sequentially or simultaneously. The balloons may have a non-symmetric shape as shown to help direct the electrodes to the commissures during inflation. Once inflated (FIG. 27b), energy can be delivered between the electrodes 272 (which can each be connected to sources with opposite polarity), to create the desired fixation shown in FIGS. 2g and 24b.

Figure 28C:
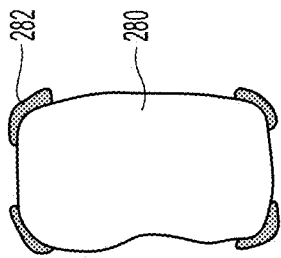
FIGS. 28a-28d illustrate various embodiments of balloons having electrodes.
Figure 28B:
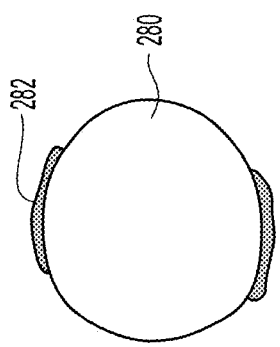
Figure 28A:
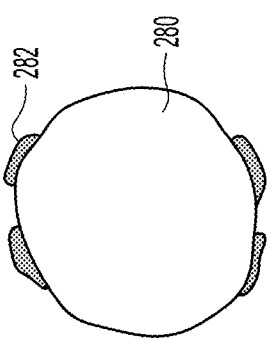
Figure 28D:
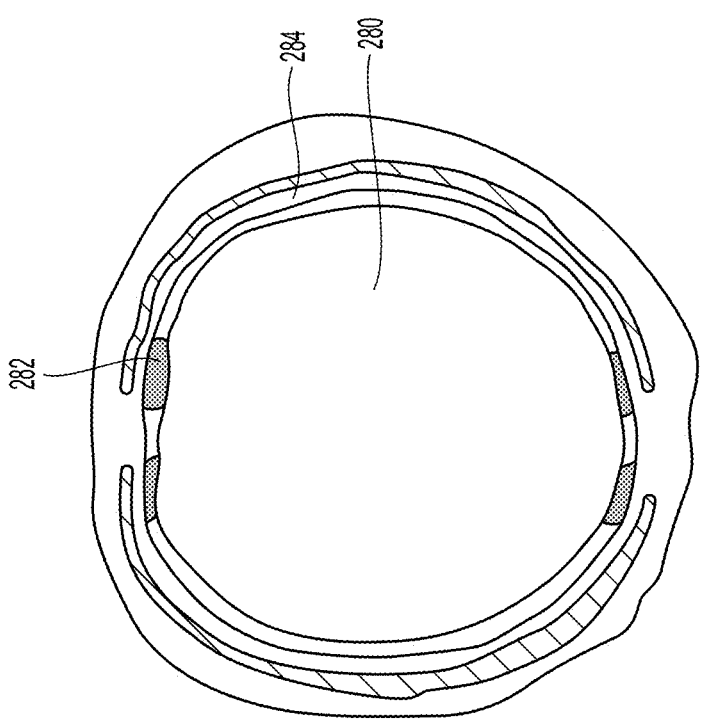

FIGS. 28a-28d depicts the use of a single balloon 280 placed in the true lumen of the vein as opposed to within the sinus of the newly create valve leaflets. Electrodes 282 shown on the different inflated balloon surfaces can be monopolar electrodes or other heating elements. FIG. 28a depicts one configuration, which delivers heat to each leaflet near both of its commissures. FIG. 28b depicts another embodiment in which two wider electrodes 282 are used to simplify the manufacturing process. FIG. 28c depicts the use of a rectangular shaped balloon 280, which will allow for self-orientation of the balloon between the leaflets. FIG. 28d, depicts the use of the configuration shown in FIG. 28a. In the inflated position, the balloon 280 directs heating elements 282 to specific locations on the leaflets 284. In this embodiment, depending on the type and amount of energy used, tissue welding may not be required, but rather a shrinking of the top edge of the leaflet to achieve fixation via shrinkage. Alternatively, with the correct settings, it may be beneficial to weld the leaflet to the vessel wall at the appropriate location to obtain a fixed geometry.

Alternatively, in some embodiments, a clamping instrument is used to capture two opposing leaflets and bring them into contact with each other prior to welding or heating. This approach has the advantage of ensuring the tissue contact geometry can be made to be consistent, as well as the normal force experienced between the leaflets can be very well controlled based on the clamping force. Additionally, this type of tool is versatile in that it can be used to fix natural valve leaflets or autologously created valve leaflets.

An example of this is shown in FIG. 29a-29d in which the two symmetric arms 291 have elbows 292 so that when the arms are retracted or extended with respect to their support shaft 293, they open and close. The arms 291 each have an electrical insulator 294 around them that extends their entire length up to just distal to the distal bend of the elbows 292. This insulator 294 can be made from FEP heat shrink or another type of polymer heat shrink, or an insulative coating, or any other thin electric insulator known in the art. This allows the non-insulated portions of the arms to function as electrodes and/or to deliver heat. The arms 291 may have flat cross section to prevent relative rotation despite articulation or rotation of the support shaft 293. FIG. 29b depicts a few different cross sectional shapes the arms 291 can have. The distal ends 295 of the arms 291 may have serrated teeth to increase surface contact and improve gripping ability. FIG. 29c depicts the distal end 295 of the arms 291 from the side, which may be flat or serrated. The distal end 295 of the arms 291 may come into contact with each other, or may remain a small distance apart to limit the force of contact with tissue. The support shaft 293 may be bilumen or trilumen as shown in FIG. 29d. The arms lumens 296 may have rectangular or elliptical shape to further help with alignment of the arms. A third central flush lumen 297 may be utilized for aspiration across the weld area to provide a known temperature and flow rate of fluid flow over the welding area during welding. The flush lumen 297 is in fluid communication with a fluid source on the proximal end which allows for control of volume and temperature of the fluid source (saline, heparanized saline, or whatever the physician deems a good fluid for this function). As shown, the arms can open and close on leaflets 298 to create a tissue weld in a very specific location as determined by where the arms 291 are clamped on the leaflets 298. In some embodiments, the arms can various geometries to create a variety of different types of welds. For example, the arms can be straight or curved, for example.

Another example shown in FIGS. 30a-30b includes two opposable clamp arms 300, 301 that are not symmetric. In this embodiment, one arm 300 is completely or generally straight and remains near parallel to the support shaft. The other arm 301 has a curved elbow 302, such that when it is retracted into the support shaft 303, the bent arm 301 moves laterally toward the straight arm 300 to create contact. The straight arm 300 may be advantageous for locating a particular side of a leaflet that may be held in contact with the catheter surface (with a scoop and separate motion).

In some embodiments, the clamping instrument contains or is entirely composed of electrodes, which act to deliver the energy used for tissue welding. In the case of bipolar RF energy delivery, two opposing clamps can be used as each of the two electrodes with opposite polarity. Also, a separate port for aspiration over the tissue to be welded can be used to ensure consistent flow over the surfaces. In the case of monopolar RF energy delivery, both opposing clamp arms can be used as electrodes with the same polarity.

In some embodiments, a single degree of articulation can be implemented in the clamping instrument to facilitate clamping the correct location on the autologous leaflets. If the clamping instrument is delivered through a tool port of a support catheter, the support catheter can be rotated in combination with 1 degree articulation by the clamping instrument to direct the clamps to any position in the vein lumen.

In one example a pull wire is included within the clamping instrument.

In another example, the distal end of the main shaft of the clamping mechanism is given a natural bend or bias in one direction. A relatively stiff sheath is placed around this main shaft, so that when advanced the entire clamping instrument takes a relatively strait orientation. When the outer sheath is retracted, the clamping mechanism will take a bend in a specific direction, to take its natural shape.

Figure 31C:
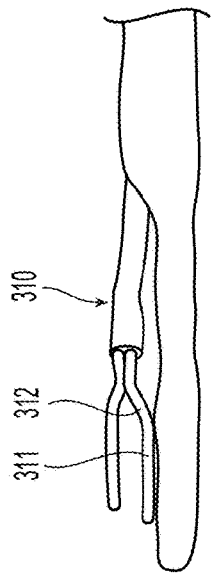
Figure 31D:
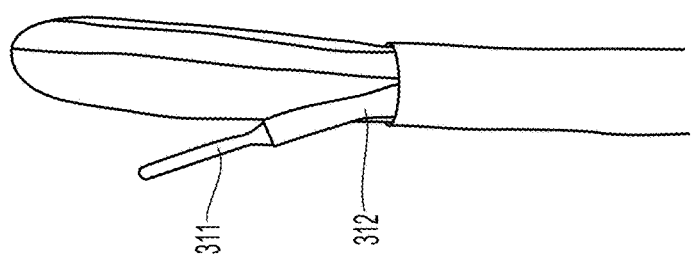
Figure 31A:
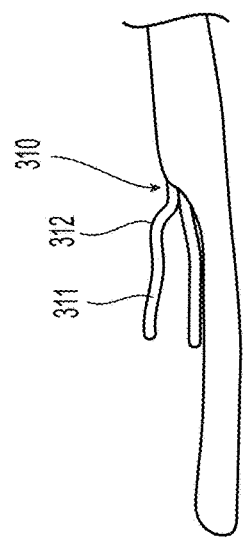
Figure 31B:
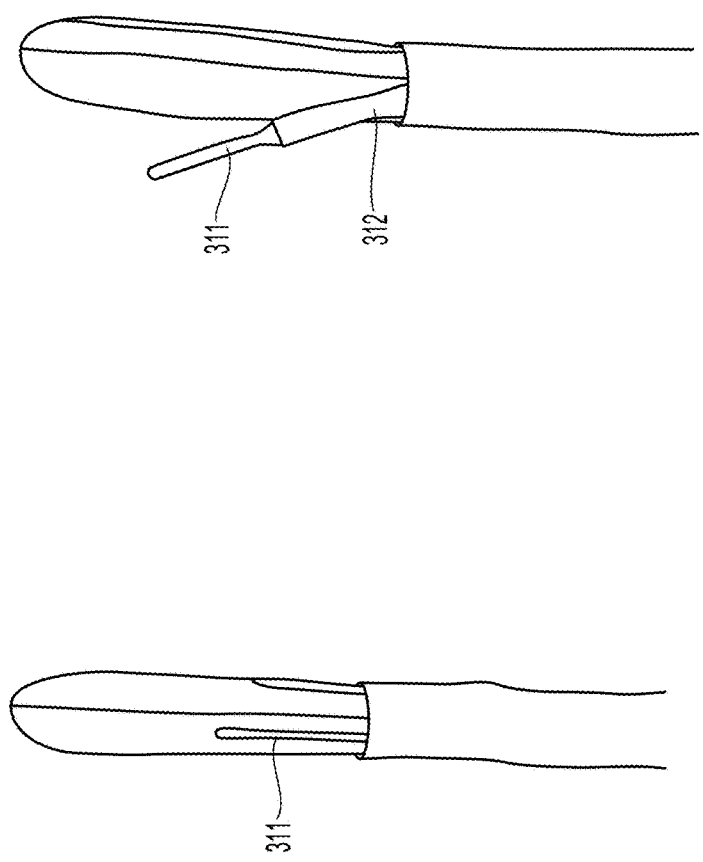

In another embodiment, shown in FIG. 31a-31d, the shaft of the clamping instrument 310 contains a preferential bend 312 beginning between 0 and 15 mm from the proximal portion of the clamping arms 311. Thus, when the clamping instrument 310 is only slightly advanced from the port of a delivery lumen (see tool port description below), the clamp arms 311 are directed nearly parallel to the axis of the support catheter (FIGS. 31a-31b). When the arms 311 are advanced further from the port of the support catheter, or if the support catheter is retracted proximally while the clamping instrument is held fixed in place longitudinally, the bend 312 in the shaft of the clamping instrument will be unrestrained, and will force the clamping arms 311 to move laterally with the bend 312 (FIGS. 31c-31d).

In another example, a sideways facing compliant balloon is attached to the shaft of the clamping instrument, so that on inflation, it is moved laterally opposite the direction of balloon inflation.

In another example, the valve creation catheter may include an apposition balloon, which can be used to direct the fixation tool if it is delivered through a tool port.

In some methods, as previously noted, such a clamping instrument can be delivered through the tool port of the autologous valve creation catheter, which may allow for use of other accessory tools or instruments to assist with the placement of the clamping instrument. In some such embodiments, the valve creation catheter may be comprised of one or more of the following: a tool port for delivery of the clamping instrument, a scope port or channel for visualization, one or more flush ports to mobilize the flaps from their native walls, a blunt manipulator—which may also be the distal tip of the valve creation catheter itself—for use in manipulating a leaflet to a particular position with respect to the tool port, and an apposition balloon for creating tension in the vein wall or to move the valve creation catheter about the cross-section of the vessel lumen.

Figure 32A:
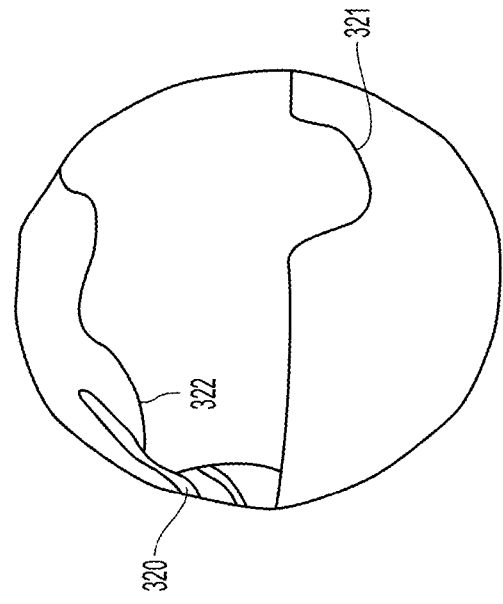
Figure 32B:
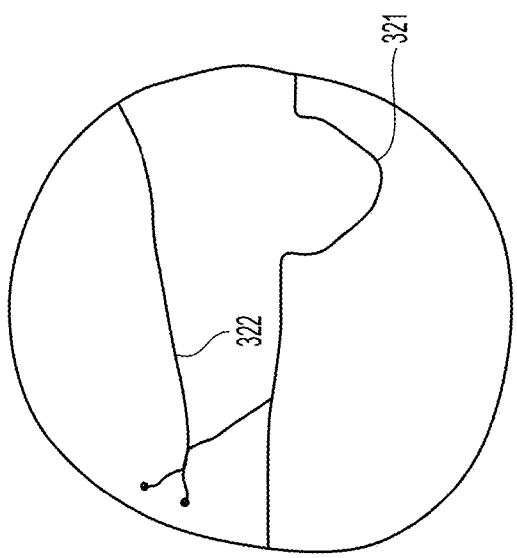
Figure 32C:
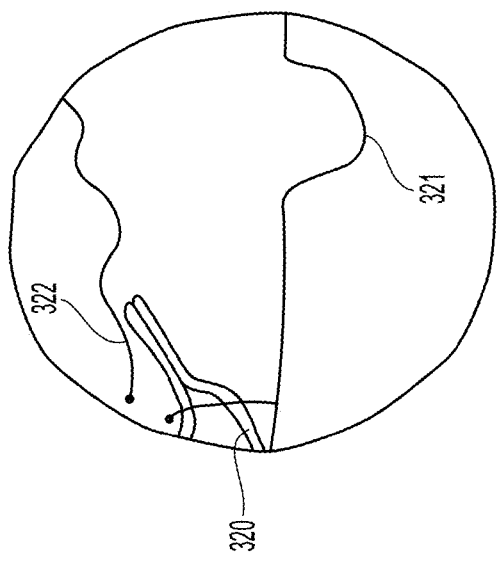
Figure 32D:
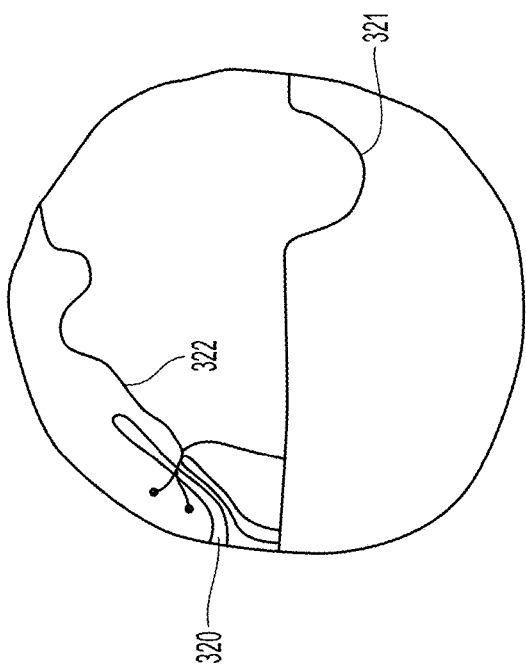

FIGS. 32a-32d depict use a clamping mechanism within a similar platform (autologous valve creation catheter) as described which has angioscopic assistance. A scope can be run in parallel to the clamping mechanism 320 through a trough 321 as shown. The images shown are depictions of the angioscopic view a user would get when using this configuration. The clamping mechanism 320 is shown on the left side of the visual field. FIG. 32a depicts the introduction of the clamp mechanism 320 through its port in the closed position. A commissure of two valve leaflets 322 is shown. FIG. 32b depicts the opening of the clamps 320 and then they are articulated (by using an articulating clamping mechanism, or by rotating or articulating the main catheter if needed and advanced until both leaflets are within its bite. FIG. 32c depicts closure of the clamps 320 around the tissue 322. In this configuration bipolar RF energy or other forms of heat energy are delivered to the tissue 322 through one or both of the clamps 320. FIG. 32d depicts the final state of the tissue 322 after applying heat. Notice a tissue weld, but also increased tautness in the valve leaflet 322. Additional catheter attributes, not depicted, can be used in conjunction. For example, flush ports can be used for better visualization.

Figure 33B:
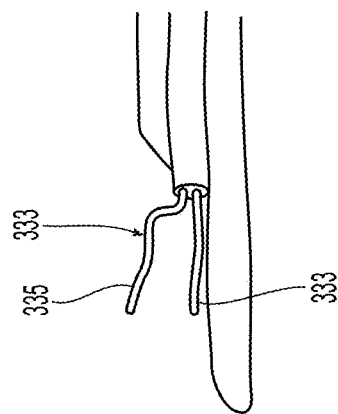
Figure 33A:
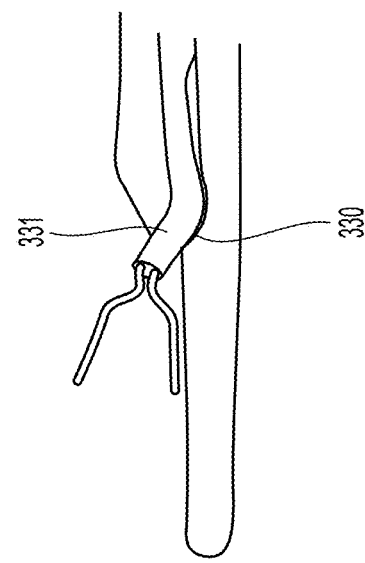

In a similar embodiment, as shown in FIG. 33a, a ramp 330 can be included leading out of the tool port exit. This forces the clamping mechanism shaft 331 to bend upward upon exiting the port. This allows the clamp arms to open wide without getting in the way of the catheter surface distal to the tool port.

As shown in FIG. 33b, no ramp is included at the tool port, but the laterally asymmetric opposing clamps 333 (with one strait arm 334 and one bent arm 335) are used. As can be seen the straight arm 334 can slide along the flat catheter surface distal to the tool port, and scoop under a leaflet that may be resting on the surface of the catheter due to the placement of the blunt distal tip of the catheter into the autologous valve pocket.

Figure 34A:
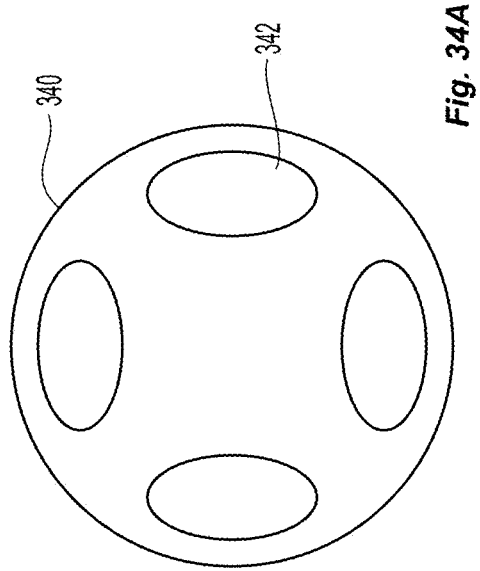
Figure 34B:
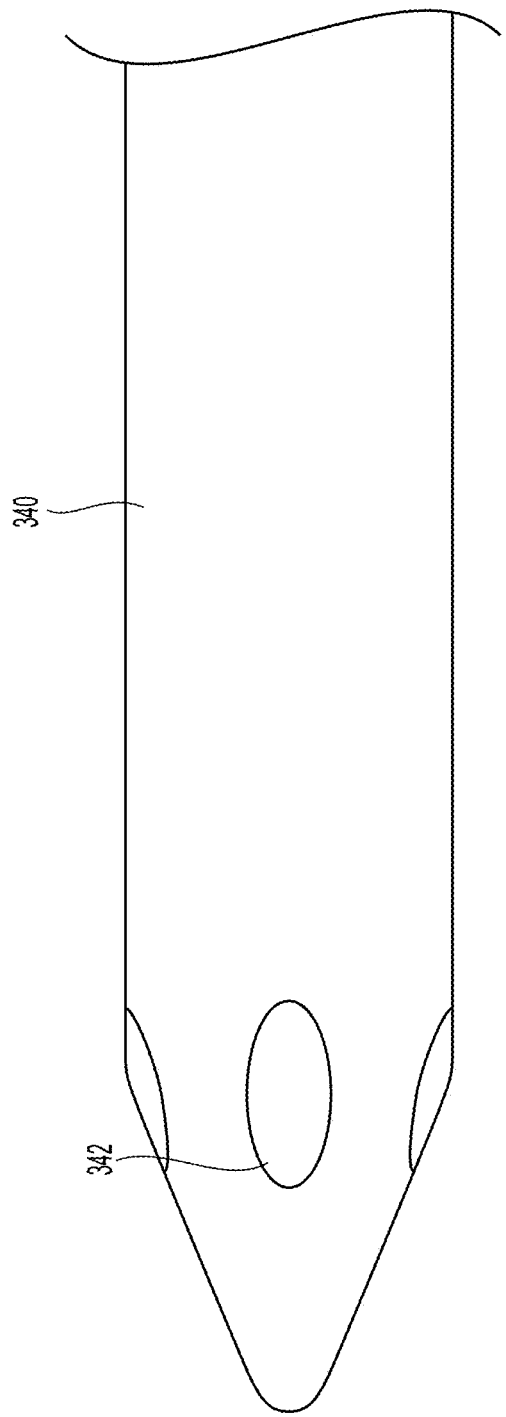

In some embodiments the clamping instrument can be introduced through a separate supporting catheter, which may include all or some of the aforementioned tools included in the valve creation catheter, but this catheter can be specifically designed for valve fixation. In one particular embodiment, the supporting catheter 340 has 4 ports 342 (FIG. 34a-34b). Two of them are opposing flush lumens with outward oriented distal ports to direct fluid into two valve pockets to open them up for fixation. The third port is used to direct an angioscope to the fixation site. The forth port acts as a tool port for delivery of the clamping instrument in a similar manner to what was previously described.

Lumen Obstruction Cutter

Figure 35A:
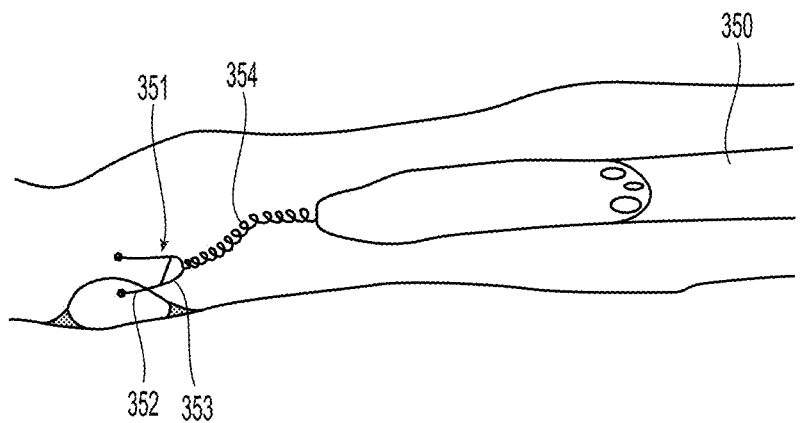
FIGS. 35a-35b illustrate various embodiments of an obstruction cutter.
Figure 35B:
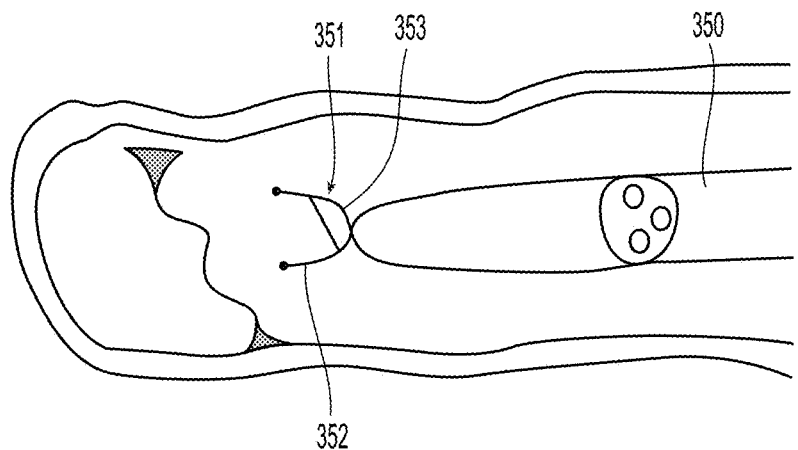

Diseased lumens can often present complex lesions, fibrosis, clots, leaflets, plaque, syneechia, false walls, or other pathological obstructive structures. These can make navigating a catheter through these lumens difficult. Specifically, in patients with chronic venous disease or post thrombotic syndrome, certain fibrotic lesions are known to be attached at more than one point to a vessel wall, in spider-web like fashion. FIGS. 35a and 35b depict two embodiments of a luminal obstruction cutter 351, to serve the purpose of facilitating navigation through an obstructed lumen with a catheter 350, and to eliminate flow obstructive lesions from the lumen.

FIG. 35a depicts an embodiment of a luminal obstruction cutter 351. In this embodiment, the cutter 351 is comprised of a flexible shaft 354, a "U" shaped jaw 352, and a hidden blade 353, which is mounted on the distal most section of a catheter 350. The flexible shaft is built to be non-traumatic and in some embodiments is actuatable. The U shaped jaw 352 allows the blade 353 to be hidden from cutting flat surfaces. The U shaped jaw 352 only allows certain pathological lesions to enter. As the catheter 350 is advanced the U shaped jaw 352 may capture multiple strands of cuttable material, funneling them to the blade 353 until the catheter has been pushed enough such that the lesion is under tension and is forced into the blade 353. At this point, the lesion is separated from itself, and the catheter can continue forward.

FIG. 35b depicts a similar embodiment without a flexible guide. In this embodiment, the U shaped jaw 352 and blade 353 are housed directly on the distal end of a catheter 350. In this way, there is a one-to-one correspondence between the cutter and the catheter.

Other shapes and forms of such a cutter exist as well (not pictured). For example a cutter could have a moving or vibrating blade like in a beard shaver. Such a moving blade may or may not be protected by a U shaped jaw. In other embodiments, the distal end of the cutter might be comprised of multiple jaws which may be as simple as tabs spaced evenly apart (like in a beard cutter).

Double Balloon Catheter

FIGS. 36a-38c depict a catheter embodiment useful in the creation of autologous valves in a bodily lumen. In some scenarios it may be advantageous to create two leaflets directly opposing one another (180 degrees apart), and located at the same longitudinal location. In order to ensure the leaflets are at the same longitudinal location, a clever mechanism can be used to prevent the need for retraction of the catheter after placement of a first balloon into a vessel wall.

Figure 36A:
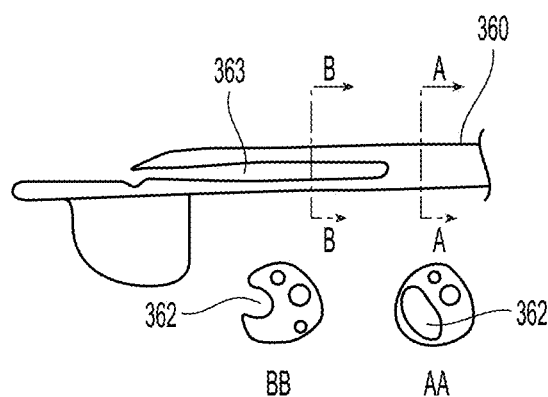

FIG. 36a-36d depict a catheter 360 having a double balloon exchange catheter mechanism. As can be seen in FIG. 36a, the proximal cross section (AA) depicts a multi-lumen extrusion. The top lumen is for flush, the right lumen is for visualization, the bottom lumen is for a wall apposition balloon or mechanism, and the forth oval-shaped lumen is to house the valve creation mechanisms 361, 361'. The oval shape allows it to carry two valve creation tools (one for each leaflet). This lumen does not have to be oval shaped, that is just an efficient way to house two tubular tools. The more distal cross section (BB) depicts the tool carrying lumen as shrunk down to a circle with one unsupported wall (formed by a longitudinal slot 363 as seen on the longitudinal view of the catheter). The transition of the tool carrying lumen 362 from an oval to a smaller circle contains a ramp of sufficient length so as to make the transition not too abrupt for a given tool. In one such embodiment the ramp and transition length is between 0 and 2 cm. In another such embodiment it is between 2 mm and 1.5 cm. In another embodiment it is between 3 mm and 8 mm. Additional description of the catheter and visualization tool can be found in International Publication No. WO 2013/119849 which is herein incorporated by reference in its entirety.

Figures 36B, 36C:
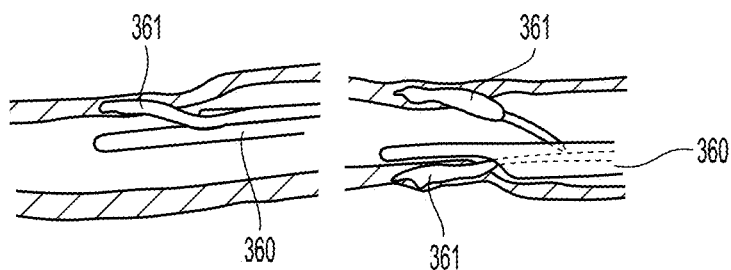
Figure 36D:
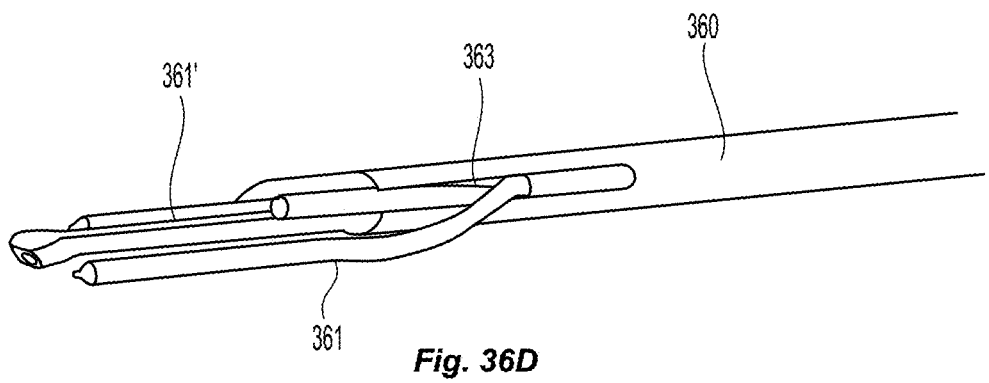

FIG. 36b depicts the valve creation catheter 360 after having placed the first leaflet creation tool 361 into but not through the vein wall. Once the first tool has been placed into the wall, and important step is needed. The balloon or leaflet creation tool needs to be ejected from the slot 363, so that the distal portion of the tool is outside the confines of the tool lumen from cross-sectional plane (BB) and distal to that. In other embodiments, the tool might need to be ejected for the entire distal segment leading all the way back to the most proximal edge of the slot.

Ejection can be performed simply by advancing a second leaflet creation tool 361' through the oval lumen shown in (AA) distally until it is forced up the ramp and into the shaft of the first tool. Due to the outward angle of the transition ramp (as can be discerned from the angular orientation of the oval lumen), this force directs the shaft of the first tool outward through the slot 363. In another embodiment a pusher rod can be used, which can then be removed so that a new tool can be inserted. In another embodiment, a spring mechanism can be used to eject the first tool. In another embodiment in which the first valve creation tool is a balloon or expanding object, the tool can be slightly inflated or expanded, which will force the tool to eject itself distally. In some embodiments, after the distal portion of the first tool has been ejected, a slidable sheath may be retracted along the shaft of the first tool, such that the distal most section of the tool shaft is made less stiff. In another such embodiment, a stiffening wire within the tool can be removed to make the distal portion of the first tool less stiff. In another embodiment the tool shaft is just made from a material that isn't very stiff, but is still able to be pushed through this lumen and into the wall.

It may be advantageous for the slot width to be somewhat constraining on the tool while it is within the tool lumen depicted in (BB). This constraint is needed for precise maneuvers required for placement of the tool into the wall (such as passing needles into the wall). In some such embodiments the slot width is between 80% and 120% the diameter of the leaflet creation tool. In other more constraining embodiments, the slot width is between 85% and 95% of the diameter of the tool diameter.

Once the first tool has been ejected, the catheter can be rotated 180 degrees. The minimization of stiffness of the shaft of the first tool is to minimize the drag on the wall when the catheter is rotated. As can be seen in FIG. 2C, the shaft of the first tool can take a corkscrew path and allow the catheter to be rotated 180 degrees without losing its place in the wall. This orientation can also be seen in FIG. 36d.

Figure 37A:
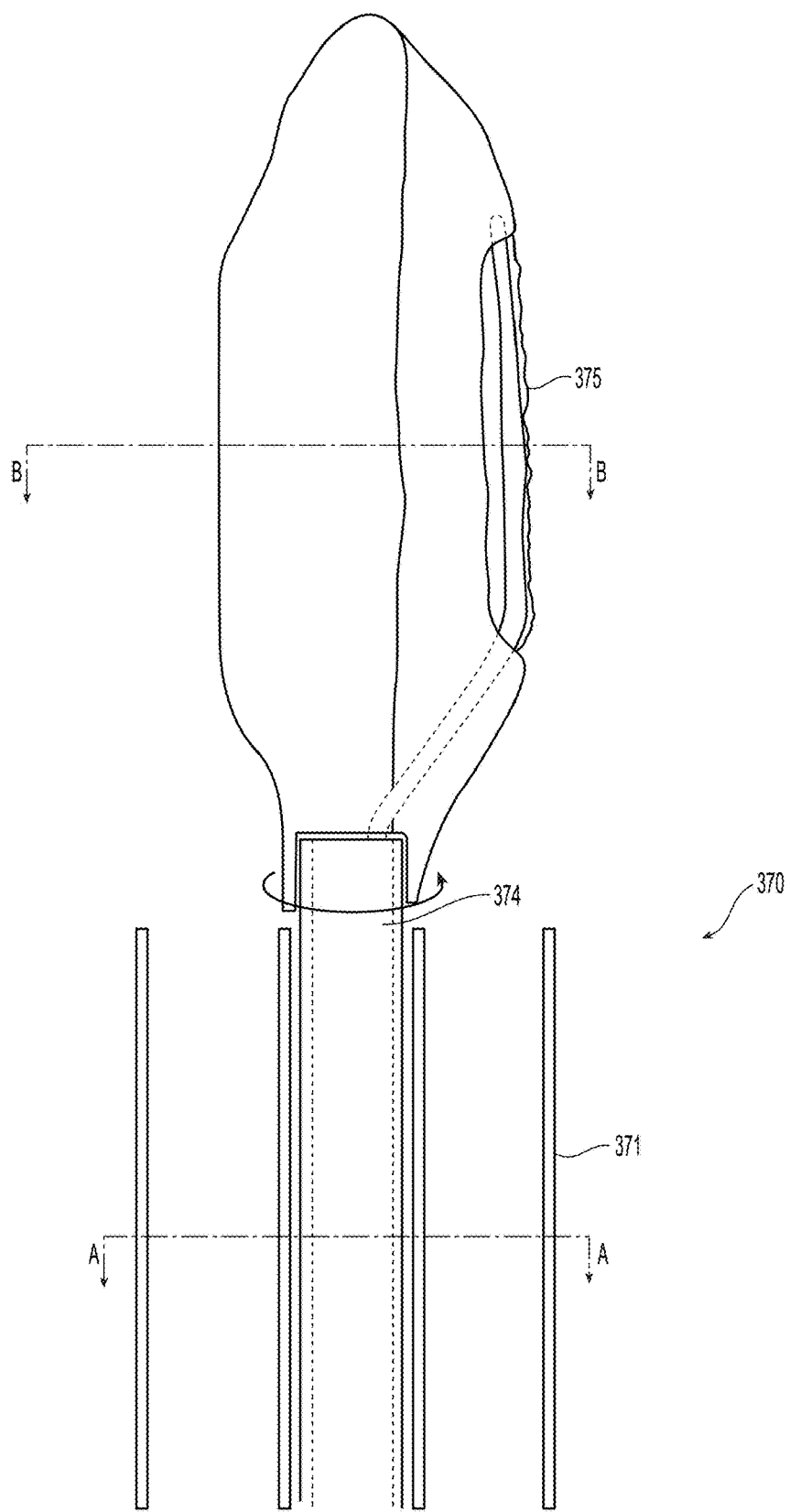
Figure 37B:
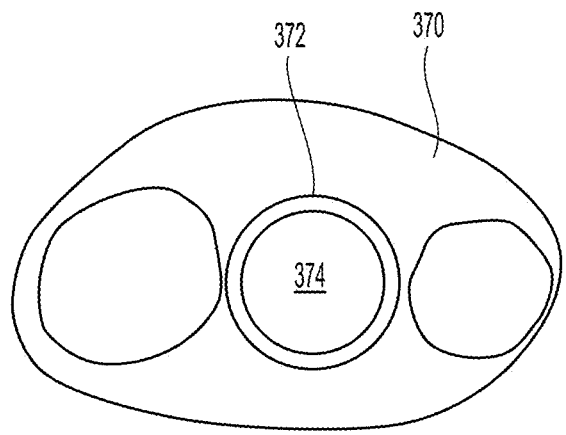
Figure 37C:
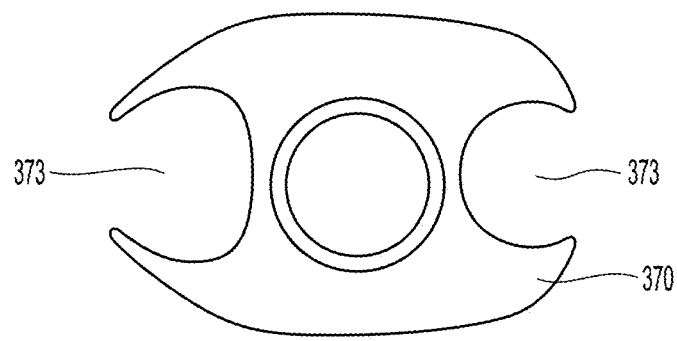
Figure 37D:
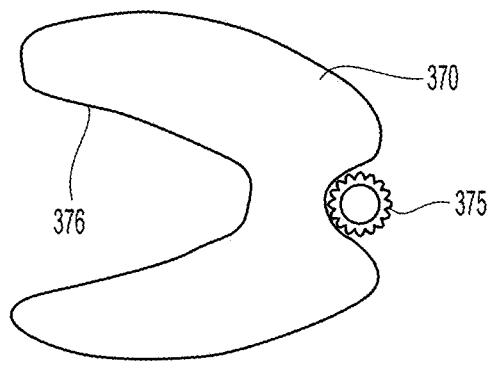

In a similar embodiment to that described in FIG. 36a-36d, FIGS. 37a-37l depict a configuration that also allows for placement of two valve creation tools into different sides of a vessel wall. In this embodiment, a catheter 370 with rotational distal end is used. FIG. 37a depicts a catheter 370 with proximal and distal end. The proximal end 371 is comprised of three major lumens 372. As seen in cross section A-A, these three lumens can be fully enclosed in an oval cross-section (as shown in FIG. 37b), or in a similar embodiment, the outermost lumens may interfere with the outer circumference of the catheter, creating two escape slots 373 (as shown in FIG. 37c). In alternate embodiments, these lumens may be encapsulated in a circular cross section. A rotation shaft 374 is disposed within the central lumen of the proximal section of the catheter 370, and is configured to rotate freely with respect to the proximal section of the catheter. This shaft 374 may be made from a stiff material such as stainless steel or a stiff plastic. This rotation shaft 374 extends distally past the proximal end and is rigidly connected or bonded to the distal end of the catheter such that when the rotation shaft is rotated (via actuation on the proximal most end of the catheter), the distal catheter section will rotate. Disposed within the hollow lumen of the rotation shaft 374 can be the inflation lumen to an apposition balloon 375. Additionally this space can be used to advance a guide wire or visualization catheter to or through the distal end of the catheter. As depicted in FIG. 37d, the distal end of the catheter is comprised of a "V" shaped surface 376, with the top of both sides being support rails used for vessel wall access support. The trough between the two support rails can be used for a visualization catheter, or to pass other interventional tools distally from the catheter such as a guide wire. On the opposite side of the catheter there is an apposition balloon 375 bonded within.

Figure 37E:
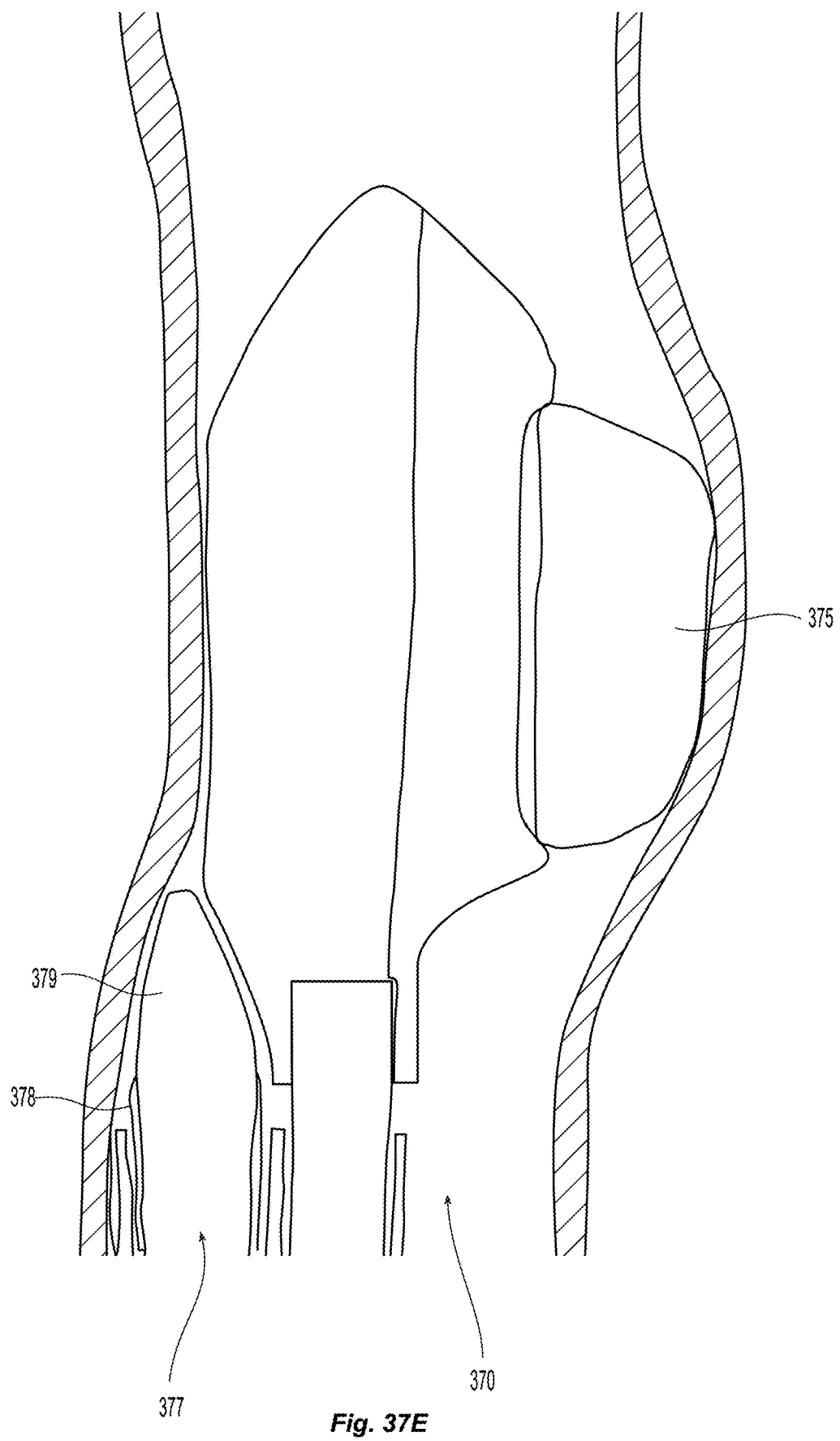

FIGS. 37e-l depict use of such a rotational catheter 370 for placement of tools into two sides of a vessel wall, with utilization of a 4-part dissection scheme. FIG. 37e depicts the first step in which the apposition balloon is inflated. A dissection assembly 377 is passed distally through the first proximal lumen on the catheter as depicted. This dissection assembly 377 contains for parts, two of which are visable in FIG. 37e. The outer most component is the access sheath 378, which is a thin walled tubular structure with some flexibility. This can be made form an extruded plastic and may be wire braided or coiled among other constructions. Within this is a dilator 379, sliably disposed within the access sheath 378, with tight tolorance between its outer diameter and the inner diameter of the access sheath. This dilator 379 contains a central lumen. The dissection assembly 377 is advanced distally to the point where the vessel wall conforms downward to the vessel wall access support surface due to the inflation of the apposition balloon 375.

Figure 37F:
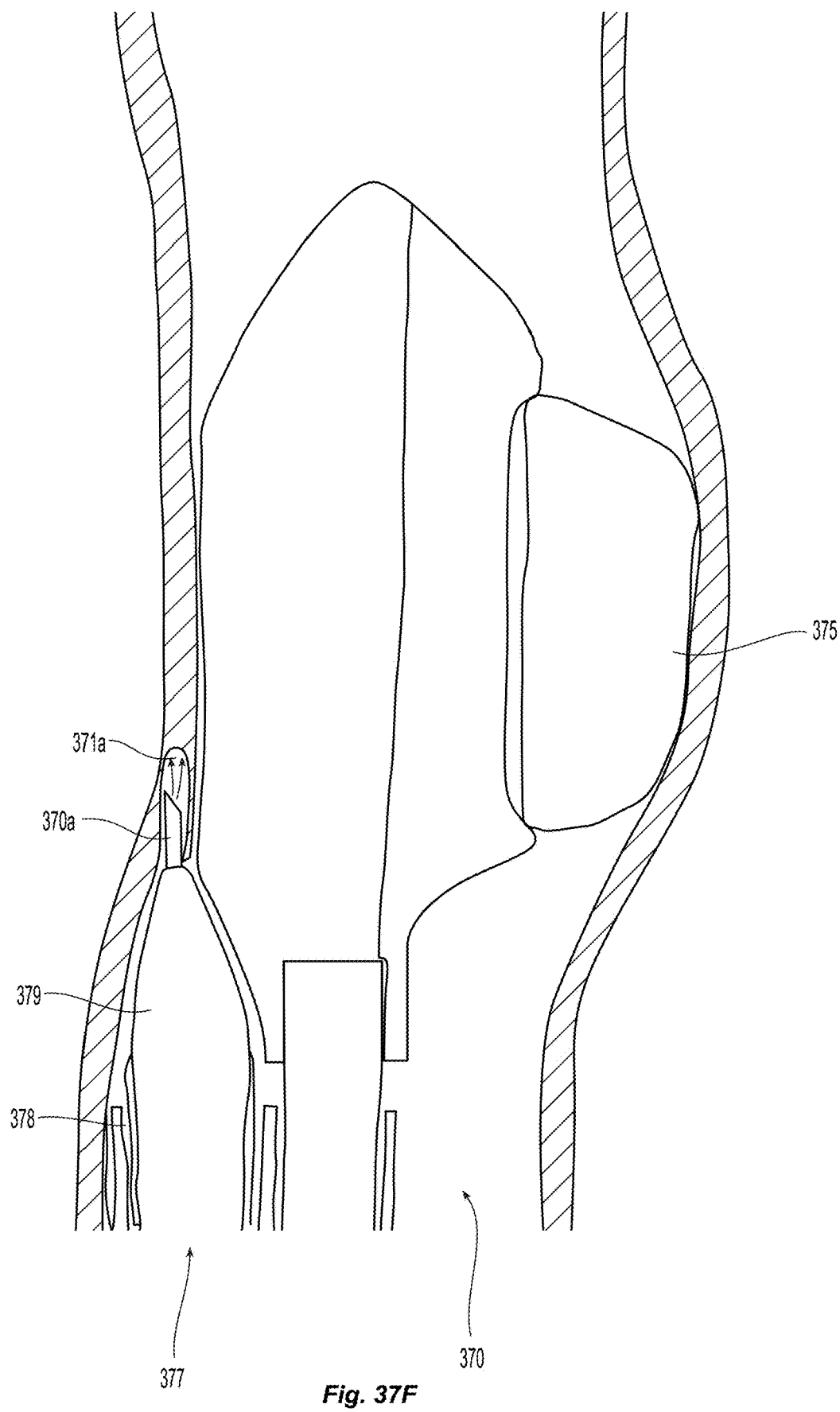

FIG. 37f depicts advancement of the inner most component of the dissection assembly 377, the puncture element 370a. This puncture element is itself hollow, and is fluidly connected to a source of pressurized hydrodissection fluid. The puncture element 370a is then advanced into the vessel wall while ejecting hydrodissection fluid until initial puncture is made, creating only the beginnings of a hydrodissection pouch 371a.

Figure 37G:
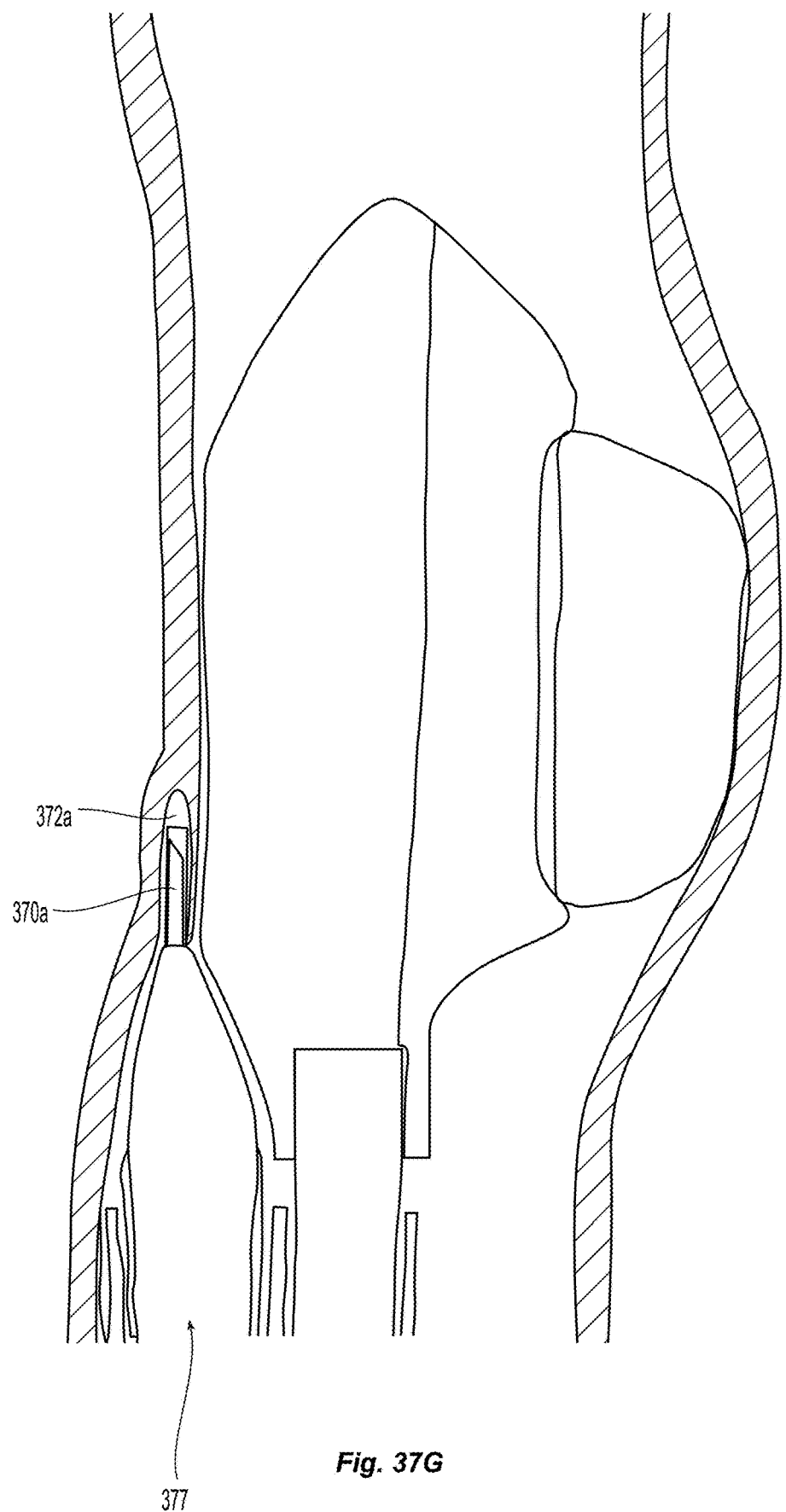

FIG. 37g depicts the advancement of the fourth component of the dissection assembly 377, the puncture element sheath 372a. This puncture element sheath 372a is a thin walled tubular structure with a square cut distal end. It is made from a semi-stiff material such as polyimide, stainless steel, or an extruded plastic with or without a wire braid or coil. This sheath is sliably disposed within the lumen of the dilator with tight dimensional tolerancing, and is slidably disposed over the puncture element 370a with tight dimensional tolerancing. This puncture element sheath 372a is advanced distally just past the bevel of the puncture element 370a, shielding it from the tissue of the vessel wall.

Figure 37H:
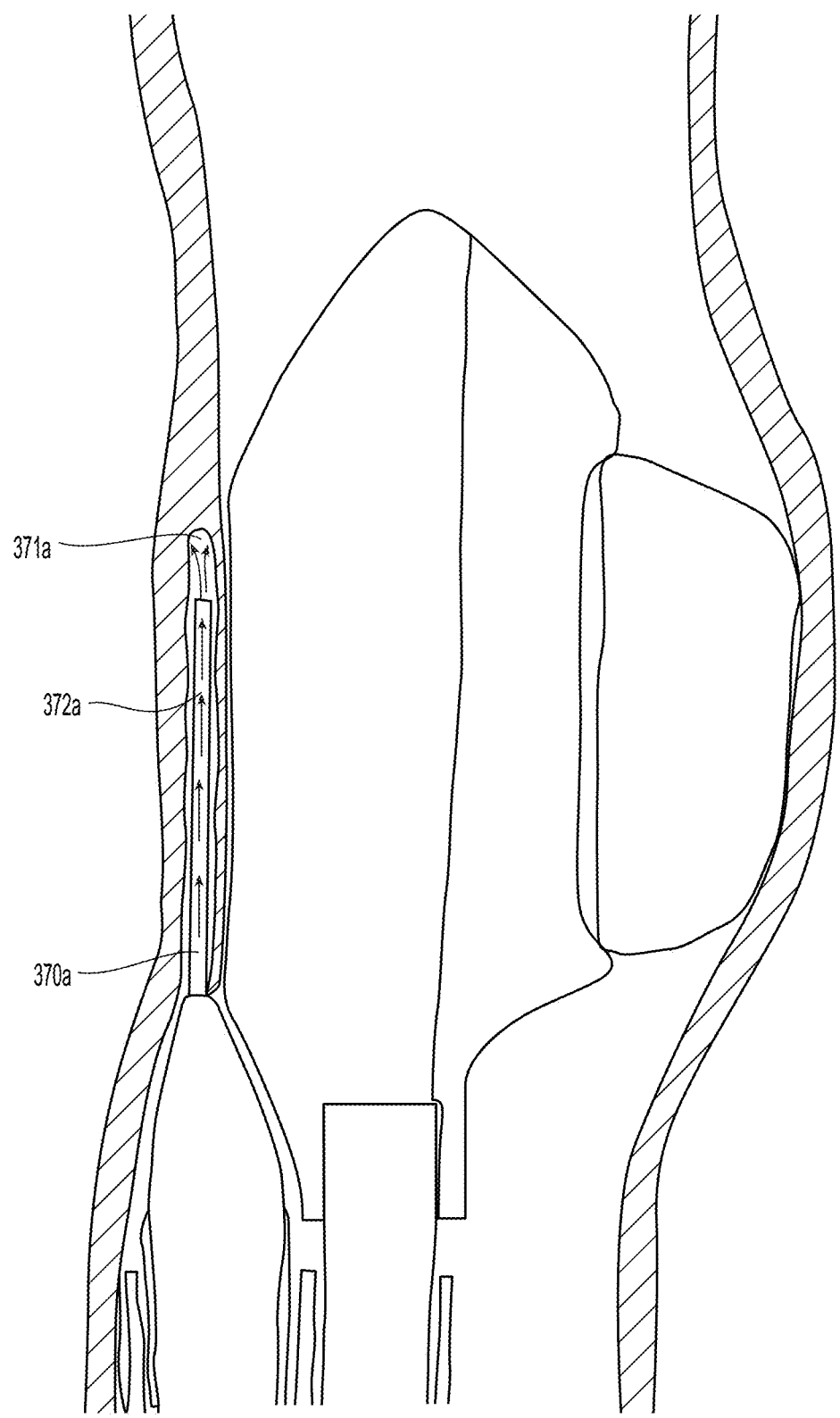

FIG. 37h depicts the advancement of the puncture element sheath 372a within the vessel wall. Hydrodissection fluid continues to pump through the puncture element sheath 372a and out the distal end of its hollow lumen as the puncture element sheath 372a is advanced, creating a longer and longer hydrodissection pouch 371a. It is advanced distally to the length of the desired vessel wall access depth. In an alternate embodiment, the puncture element 370a may be advanced along with the puncture element sheath so that the distal end of the puncture element always remains within the puncture element sheath.

Figure 37I:
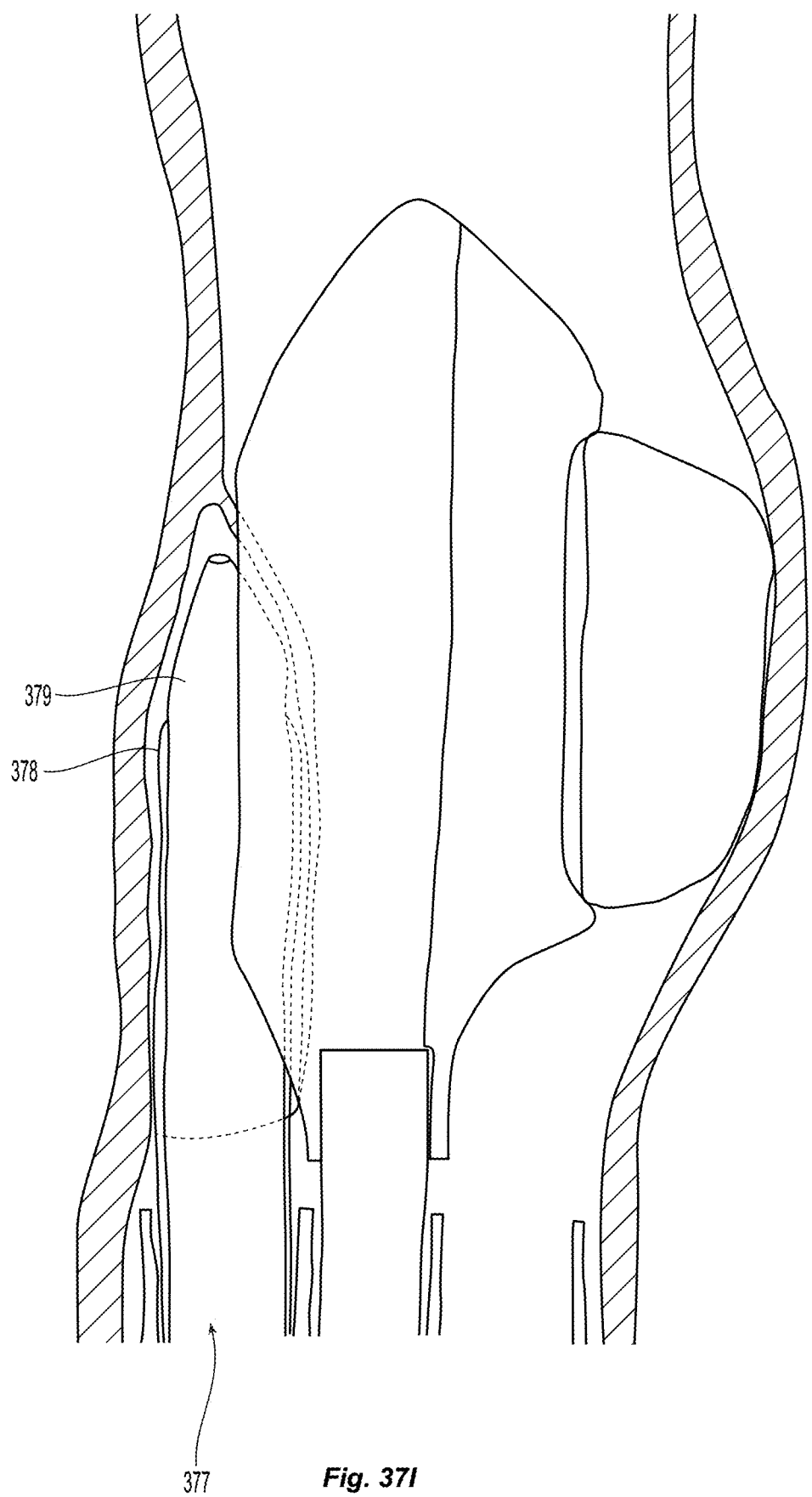

FIG. 37i depicts the advancement of the two outer components of the dissection assembly 377, the dilator 379 and the access sheath 378, over the puncture element sheath. These two components are advanced until the puncture element access sheath is disposed within the distal tip of the dilator, as shown. During this advancement, continuous hydrodissection may be used to help maintain the volume within the hydrodissection pocket, to facilite dilation and advancement.

Figure 37J:
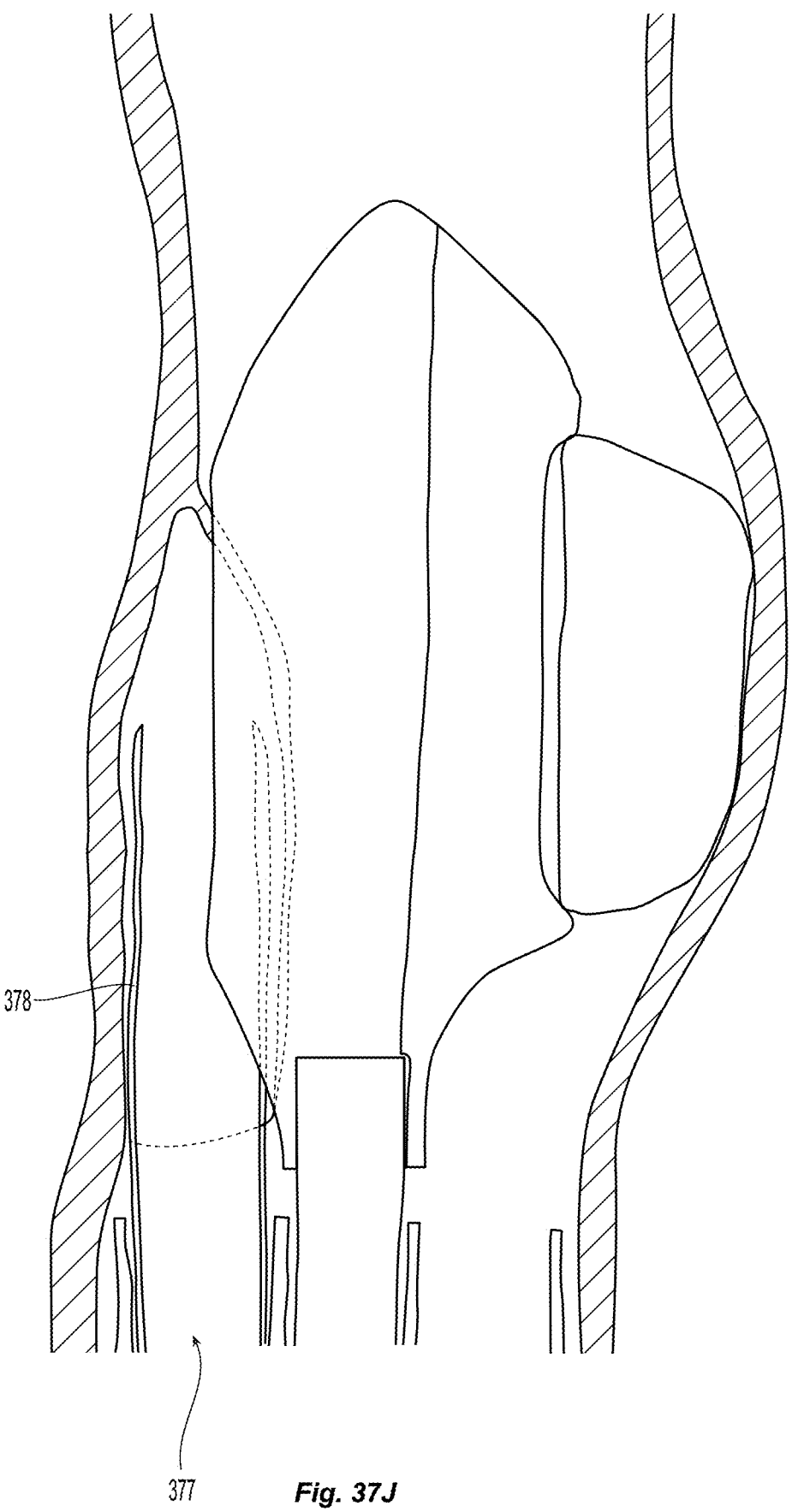

FIG. 37*j* depicts removal of the inner three components of the dissection assembly 377, leaving just the access sheath 378 within the vessel wall.

Figure 37K:
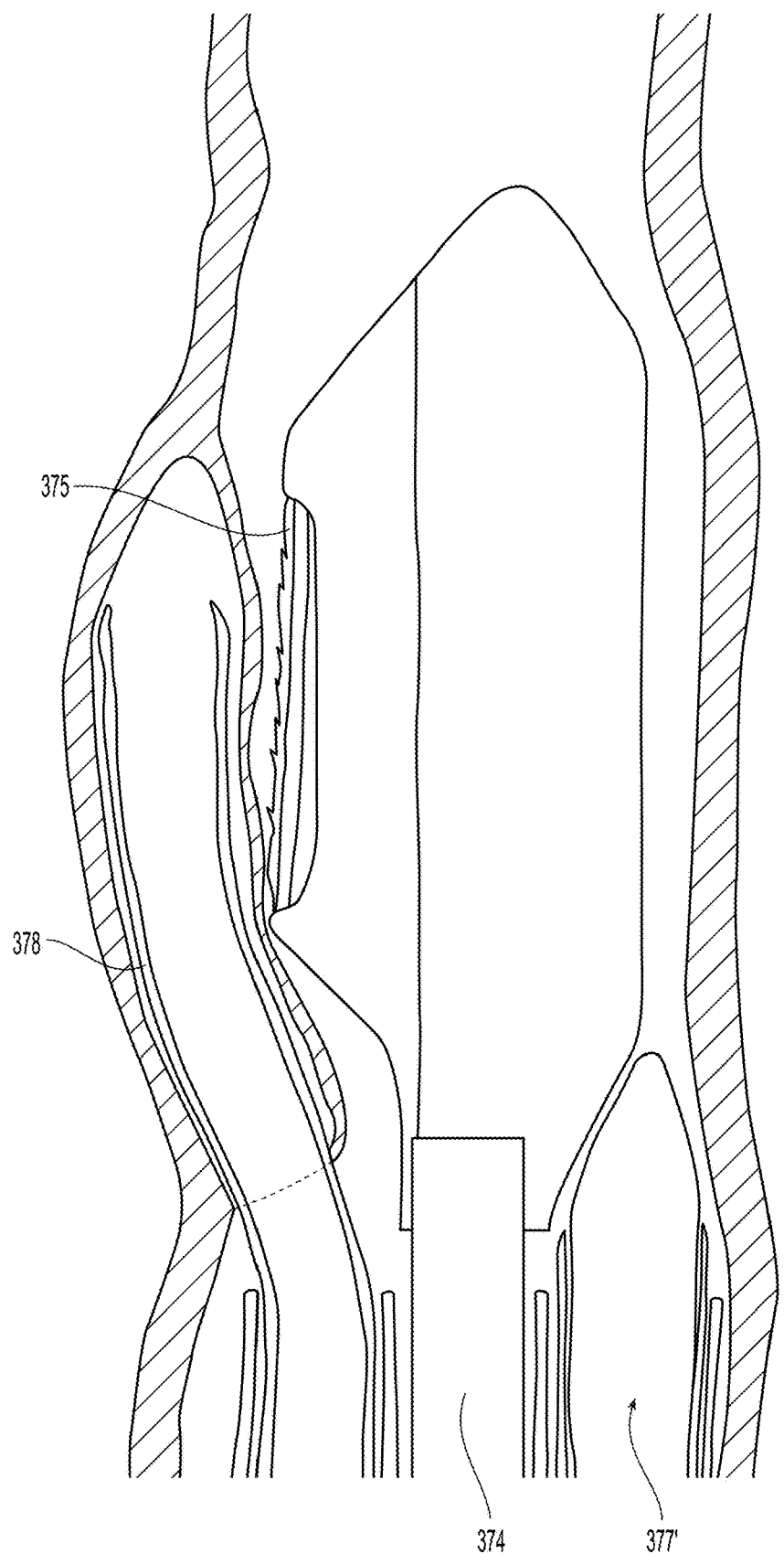

FIG. 37*k* depicts the rotation of the rotation shaft 374, so that the distal end of the catheter is rotated 180 degrees within the vessel. This rotation was carried out with the apposition balloon 375 deflated. After the rotation, the apposition balloon 375 faces the first access sheath 378 and the first dissection pocket 371*a*, while the vessel wall access support surface faces the opposite vessel wall. In this depiction, a second dissection assembly 377', similar to the first, is advanced to the distal location. From this position, the same process is used to advance the dissection assembly into the vessel wall on the second side.

Figure 37L:
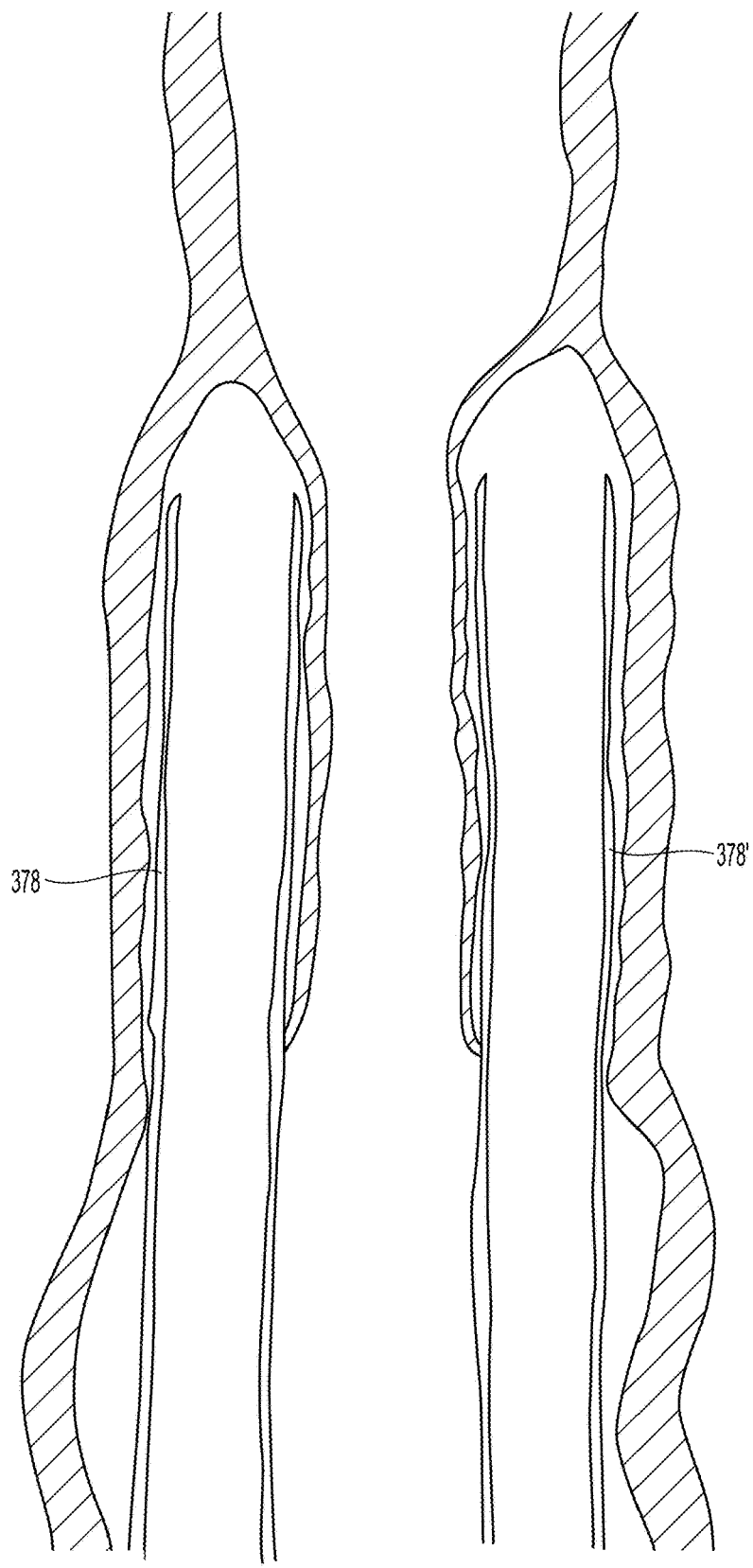

FIG. 37*l* depicts the final product of this procedure, in which two access sheaths 378, 378' are successfully inserted into opposite sides of a vessel wall. From this position, a variety of valve creation tools can be freely exchanged in and out of the dissection pockets created, so that a working bicuspid valve can be created.

Figure 38A:
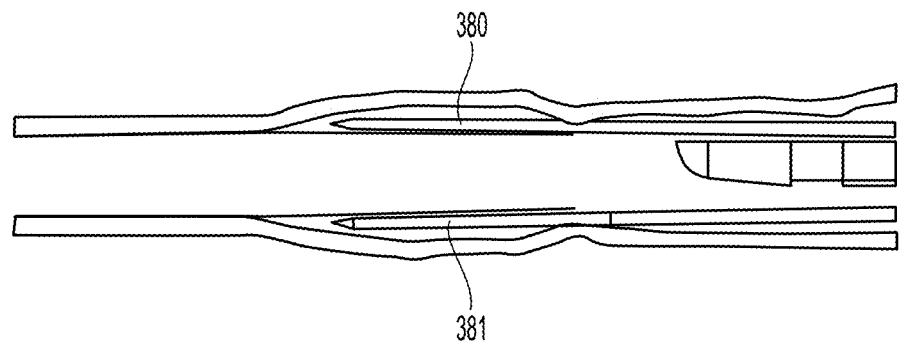
Figure 38B:
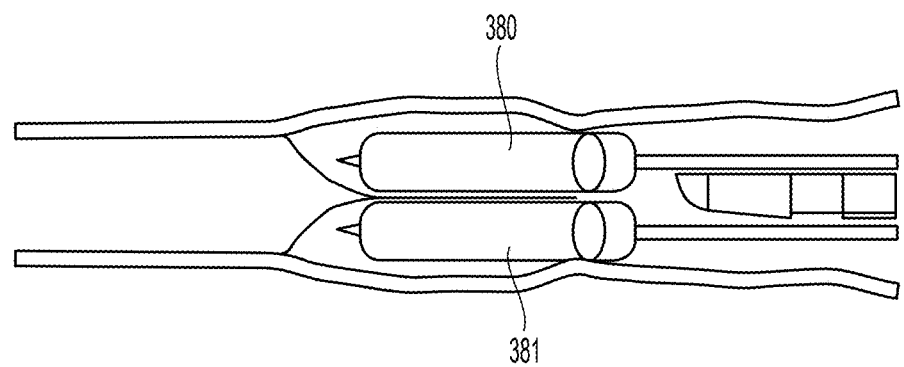

Valve Creation Tools:

FIG. 38*a* depicts two different valve creation tools 380, 381 (depicted here as balloons), which have been inserted into an intra-mural layer within a vessel wall, on both sides of the lumen. As can be seen both balloons 380, 381 are still in their deflated configuration, while both are in the wall. The user can now choose to inflate both balloons simultaneously, or one at a time, or an alternating pattern. FIG. 38*b* depicts both balloons 380, 381 being inflated simultaneously, which may help to form leaflets that have proper apposition to each other.

Figures 39A, 39B, 39C:
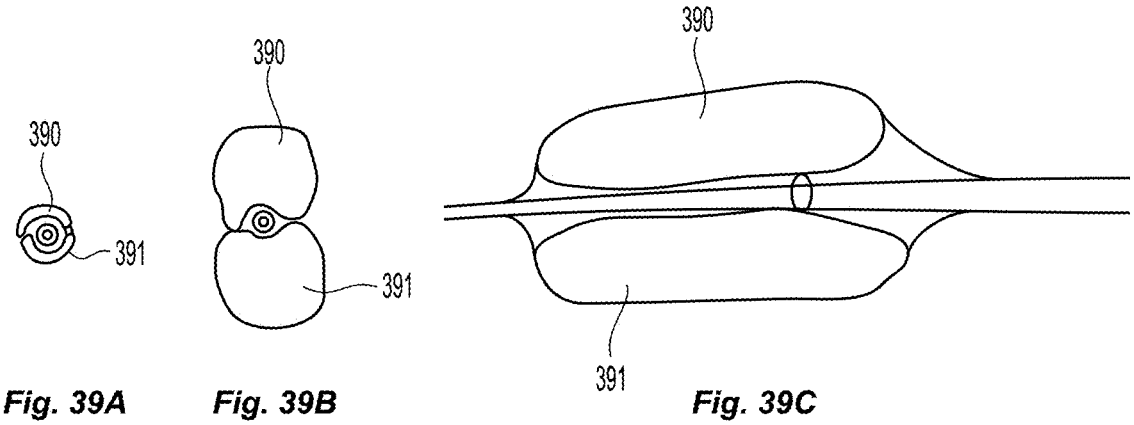
Figures 40A, 40B, 40C, 40D:
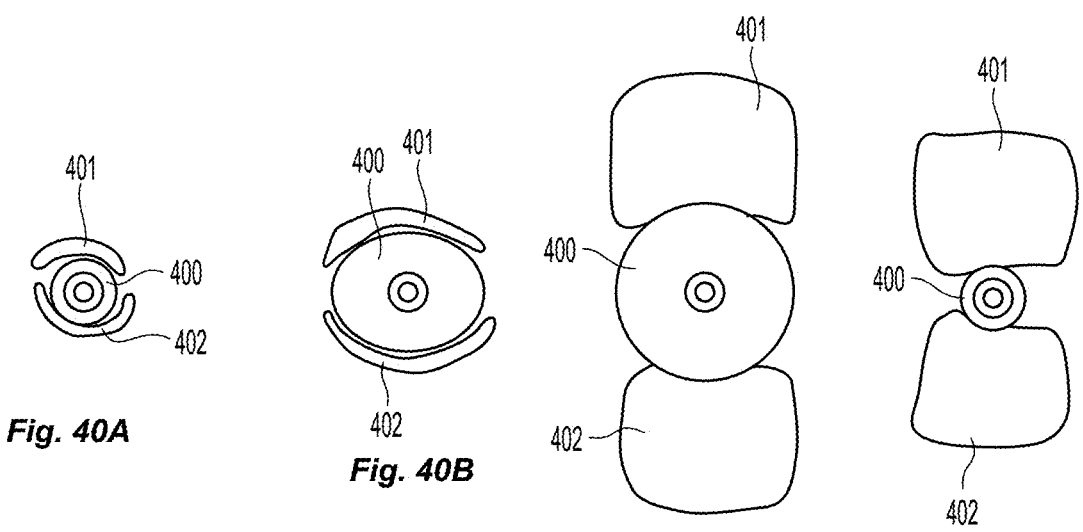
FIGS. 40a-40d illustrates an embodiment of a triple balloon device.

FIGS. 39*a*-39*c* depict the use of a custom made balloon configuration for autologous valve creation. In certain situations it may be advantageous to have an expansion geometry that is wider than it is tall such that valve width is maximized without over stretching the tissue. One such embodiment, depicted is the use of a double balloon. Two more or less circular balloons 390, 391 can be bonded together with a through lumen, such that when deflated (left) they assume a compressed, mostly tubular form. Then when inflated they form an oval shape in cross section (middle).

FIGS. 40*a*-40*d* depict a triple balloon configuration, with three more or less circular balloons 400, 401, 402 bonded to each other. In this embodiment one inflation lumen connects to the middle balloon 400, and another inflation lumen connects to the outer balloons 401, 402. This allows for inflation of the middle balloon without inflation of the outer balloons. It also allows for inflation of the middle balloons to begin dilation of a valve mouth, and then a subsequent inflation of the outer balloons to create the proper width needed. It also allows for the initial inflation of the outer balloons to get a valve mouth started, and then the use of the third middle balloon if needed to add additional width.

In other embodiments not shown this idea could be expanded to many balloons. As many as 100 micro balloon pockets could be used, so that selective inflation of different balloon pockets yield different inflation diameters or geometries, which could be which could be very well controlled based on amount of fluid used and which chambers were inflated. If pressure threshold one-way valves were connected between the balloon pockets, different inflation pressures would allow fluid to flow into more and more balloons, increasing the size controllably.

Figure 41B:
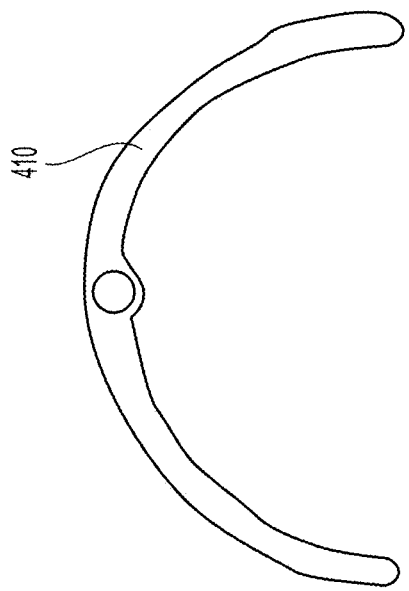
Figure 41A:
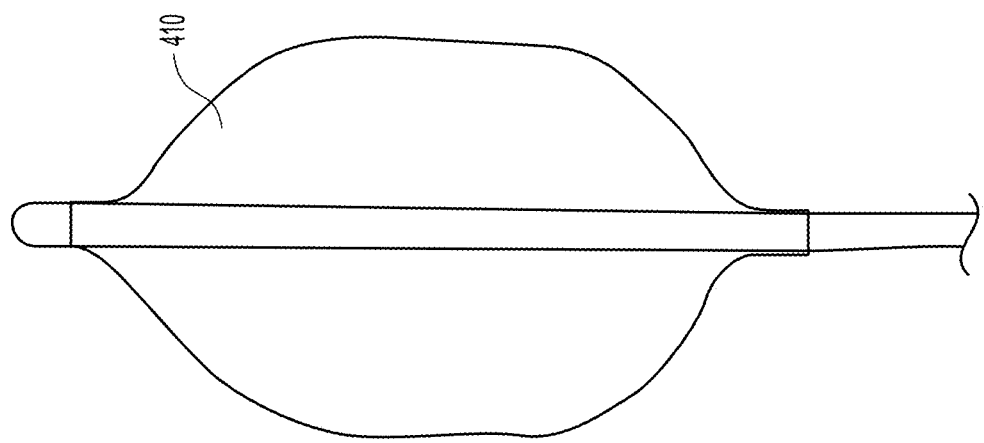

In a similar embodiment, FIGS. 41*a* and 41*b* depict a flat and curved balloon geometry in its inflated state. This geometry is designed specifically to create a wide dissection within a vessel wall, covering up to 180 degrees of the circumference of the vessel wall. The curvature of the balloon 410 helps it to follow the curvature of the vessel. Additionally, the flatness of the balloon 410 allows it to be inflated within a vessel wall to create a dissection without the need for removing other catheter materials from within the lumen of the vessel at the same longitudinal position. This is because the inflation of the balloon doesn't push the leaflet into the middle of the lumen and thus leaves the lumen space clear for other tools.

Figure 42B:
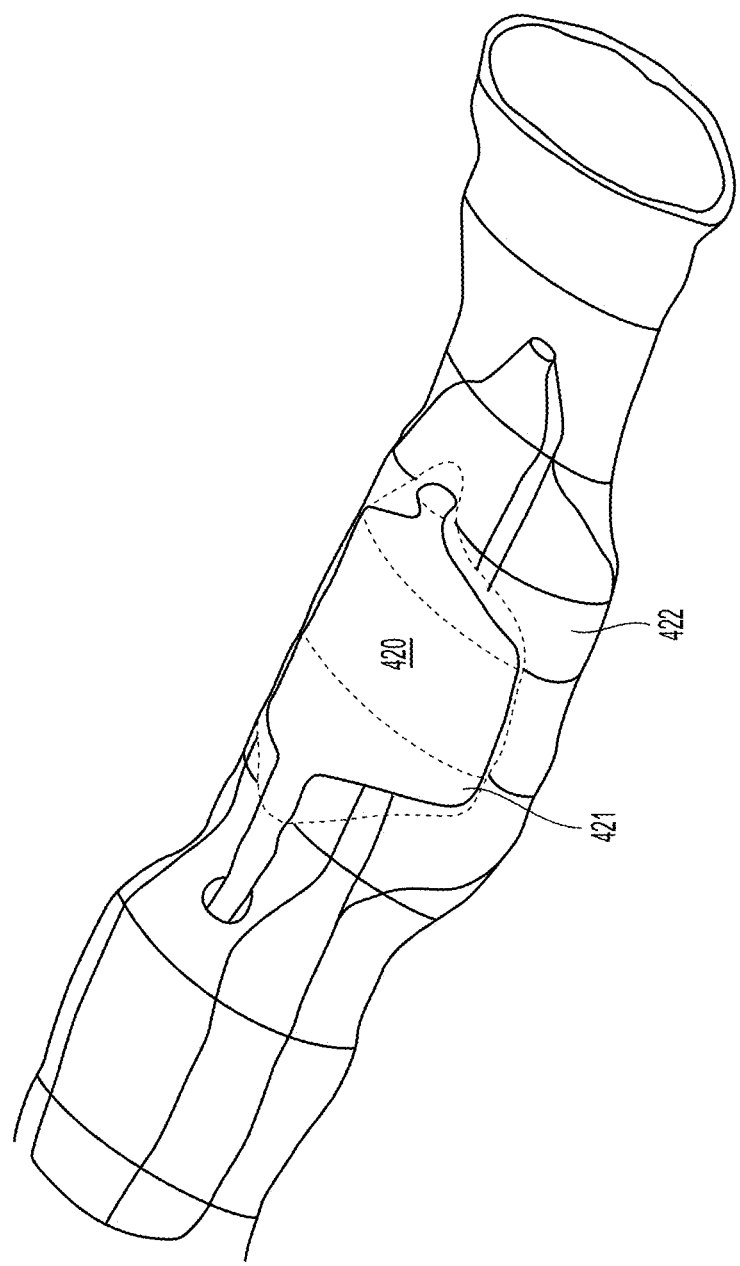

FIGS. 42*a*-42*b* depicts the use of the embodiment described in FIGS. 41*a*-41*b*. Utilizing a vessel wall access catheter, a deflated valve creation balloon 420 is placed into the vessel wall but not through it, as shown in FIG. 42*a*. Once within a sub-intimal space, and oriented such that the sideways inflating wings are oriented with the circumference of the vein wall, the balloon 420 is inflated. As it inflates, the flat balloon wings 421 expand laterally around half of the circumference of the vein, still within the vein wall, as depicted in FIG. 42*b*. This will create a 180 degree dissection within the vein wall. Note that the vessel wall access catheter is left in place within the vein lumen and the apposition balloon 422 is left inflated. This may help to ensure the flat, curved balloon inflates in the right direction, as a lateral dissection will be the path of least resistance.

In general, the majority of embodiments described depict bicuspid valve fixation. These embodiments could be used for monocuspid or tricuspid leaflet fixation as well with appropriate design changes that would be well within the abilities of a person with ordinary skill in the art, by for example forcing the leaflet into contact with the vessel wall, and applying the energy through the lumen side of the leaflet.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A system for fixing an intimal leaflet to a wall of a vessel, the system comprising:
    an expandable member, wherein the expandable member is configured to press the intimal leaflet towards the wall of the vessel as it expands;
    a first delivery element carried by the expandable member, the first delivery element comprising a first puncturing element positioned to puncture through a first edge of the intimal leaflet and at least partially through the wall of the vessel upon expansion of the expandable member;
    a second delivery element carried by the expandable member, the second delivery element comprising a second puncturing element positioned to puncture through a second edge of the intimal leaflet opposite the first edge and at least partially through the wall of the vessel as the expandable member expands; and an anchor slidably positionable in the first delivery element, wherein the anchor is configured to attach a first portion of the intimal leaflet to the vessel wall, wall of the vessel as the expandable member expands.

2. The system of claim 1, further comprising:
a catheter having a proximal end and a distal end opposite the proximal end, wherein the expandable member is carried by the distal end,
wherein—
the first delivery element further comprises a first lumen extending from the first puncture element towards the proximal end of the catheter and a first lumen port positioned within the first puncture element; and
the second delivery element further comprises a second lumen extending from the second puncture element towards the proximal end of the catheter and a second lumen port positioned within the second first puncture element.

3. The system of claim 1 wherein the first delivery element is configured to deliver a first clip between the first edge of the intimal leaflet and the vessel wall when it punctures the first edge of the intimal leaflet, and wherein the second delivery element is configured to deliver a second clip between the second edge of the intimal leaflet and the vessel wall when it punctures the second edge of the intimal leaflet.

4. The system of claim 1 wherein the expandable member is an inflatable balloon.

5. The system of claim 1 wherein the first and second puncturing elements have a length between 0.5 mm and 1.5 mm.

6. The system of claim 1 wherein the intimal leaflet is a first intimal leaflet, wherein the vessel further includes a second intimal leaflet opposite the first intimal leaflet on the vessel wall, and wherein the expandable member can be rotated within the vessel to position the first and second delivery elements to puncture first and second edges of the second intimal leaflet.

7. The system of claim 1 wherein the intimal leaflet is a first intimal leaflet, wherein the vessel further includes a second intimal leaflet opposite the first intimal leaflet on the vessel wall, and wherein the system further comprises:
a third delivery element carried by the expandable member, the third delivery element including a third puncturing element and positioned to puncture through a first edge of the second intimal leaflet and at least partially through the wall of the vessel as the expandable member expands; and
a fourth delivery element carried by the expandable member, the fourth delivery element including a fourth puncturing element positioned to puncture through a second edge of the second intimal leaflet opposite the first edge of the second intimal leaflet and at least partially through the wall of the vessel as the expandable member expands.

8. The system of claim 1, further comprising:
a pusher slidably positionable in the first delivery element proximal to the anchor, wherein the pusher is configured to deploy the anchor out of the first delivery element.

9. The system of claim 1 wherein:
the anchor has a distal end portion, a proximal end portion, and a body portion between the distal end portion and the distal end portion; and
when the anchor is pushed out of the first delivery element, the distal end portion and the proximal end portion have a larger transverse dimension than the body portion.

10. The system of claim 1, wherein the anchor is configured to transition from a linear configuration within the first delivery element to a deployed configuration outside of the first delivery element.

11. A system for fixing an intimal leaflet to a wall of a vessel, the device comprising:
an expandable component positionable within a lumen of the vessel adjacent to the intimal leaflet and movable between a collapsed state and an expanded state to press the intimal leaflet toward the wall;
a first delivery channel carried by the expandable component, the first delivery channel comprising a lumen and a first puncture element positioned to puncture through the intimal leaflet and at least a portion of the wall adjacent to a first lateral edge of the intimal leaflet as the expandable component moves to the expanded state; and
a second delivery channel carried by the expandable component, the second delivery channel comprising a second puncture element positioned to puncture through the intimal leaflet and at least a portion of the wall adjacent to a second lateral edge of the intimal leaflet as the expandable component moves to the expanded state; and
a fixation element configured to be movably positioned within the lumen.

12. The system of claim 11 wherein the second puncture element is radially offset from the first puncture element by between 120 degrees and 240 degrees.

13. The system of claim 11 wherein the first puncture element is configured to be positioned within 45 degrees of the first lateral edge.

14. The system of claim 11 wherein the expandable component is positionable to cause the first and second puncture elements to puncture the intimal leaflet in a top quarter of the leaflet.

15. The system of claim 11 wherein the fixation element comprises a shape-memory device configured to move between a linear configuration within the lumen and a predetermined shape outside of the lumen.

16. The system of claim 11, further comprising a deploying member movably positioned within the lumen proximal to the fixation element, wherein the deploying member is configured to push the fixation element out of the lumen after the first puncture element punctures through the intimal leaflet and the at least a portion of the wall adjacent to the first lateral edge.

17. The system of claim 11 wherein the intimal leaflet is a first intimal leaflet, wherein the vessel further includes a second intimal leaflet on the vessel wall, and wherein the expandable component can be moved within the vessel to position the first and second delivery channels to puncture first and second lateral edges of the second intimal leaflet.

* * * * *